United States Patent [19]

Bindra

[11] 4,143,139

[45] Mar. 6, 1979

[54] 9-HYDROXYDIBENZO[B,D]PYRANS AND INTERMEDIATES

[75] Inventor: Jasjit S. Bindra, Groton, Conn.

[73] Assignee: Pfizer Inc., New York, N.Y.

[21] Appl. No.: 819,471

[22] Filed: Jul. 27, 1977

Related U.S. Application Data

[63] Continuation of Ser. No. 730,672, Oct. 7, 1976, abandoned, which is a continuation-in-part of Ser. No. 628,210, Nov. 3, 1975, abandoned.

[51] Int. Cl.[2] .................... A61K 31/35; C07D 493/12

[52] U.S. Cl. ............................ 424/248.55; 424/250; 424/263; 424/274; 424/284; 544/150; 260/326.5 CA; 260/326.34; 546/196; 546/269; 546/187; 260/345.3; 546/194; 544/364; 544/375

[58] Field of Search ........... 260/296 T, 345.3, 268 H; 424/248, 250, 284; 544/150

[56] References Cited

U.S. PATENT DOCUMENTS

| | | | |
|---|---|---|---|
| 3,901,926 | 8/1975 | Winn et al. | 260/297 R X |
| 3,929,835 | 12/1975 | Winn et al. | 260/345.3 |
| 3,968,125 | 7/1976 | Archer | 260/345.3 |

*Primary Examiner*—John D. Randolph
*Attorney, Agent, or Firm*—Connolly and Hutz

[57] ABSTRACT

9-Hydroxydibenzo[b,d]pyrans useful as analgesics, hypotensives, immunosuppressants, tranquilizers; as anti-secretory and anti-anxiety drugs; intermediates therefor and derivatives thereof having the formulae

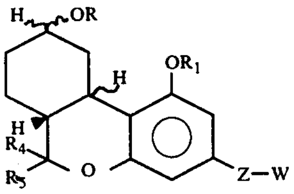

I

-continued

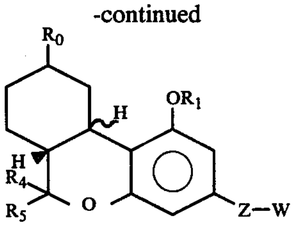

II and

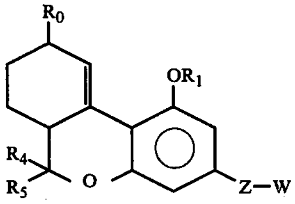

III wherein R is hydrogen or alkanoyl having from one to five carbon atoms;

$R_1$ is hydrogen, alkanoyl having from one to five carbon atoms or —CO—$(CH_2)_p$—$NR_2R_3$ wherein p is 0 or an integer from 1 to 4; each of $R_2$ and $R_3$ when taken individually is hydrogen or alkyl having from one to four carbon atoms; $R_2$ and $R_3$ when taken together with the nitrogen to which they are attached form a 5- or 6-membered heterocyclic ring selected from piperidino, pyrrolo, pyrrolidino, morpholino and N-alkylpiperazino having from one to four carbon atoms in the alkyl group;

each of $R_4$ and $R_5$ is hydrogen, methyl or ethyl;

$R_0$ is oxo or alkylenedioxy having from two to four carbon atoms;

Z is
(a) alkylene having from one to nine carbon atoms;
(b) —$(alk_1)_m$—X—$(alk_2)_n$—wherein each of $(alk_1)$ and $(alk_2)$ has from 1 to 9 carbon atoms, with the proviso that the summation of carbon atoms in $(alk_1)$ plus $(alk_2)$ is not greater than 9;
each of m and n is 0 or 1;
X is O, S, SO or $SO_2$; and
W is methyl, phenyl, p-chlorophenyl, p-fluorophenyl, pyridyl, piperidyl, cycloalkyl having from 3 to 7 carbon atoms, or monosubstituted cycloalkyl wherein the substituent is phenyl, p-chlorophenyl or p-fluorophenyl;

with the proviso that when W is methyl, Z is

—$(alk_1.)_m$—X—$(alk_2)_n$—.

21 Claims, No Drawings

9-HYDROXYDIBENZO[b,d]PYRANS AND INTERMEDIATES

CROSS-REFERENCE TO RELATED APPLICATION

This application is a continuation of application Ser. No. 730,672 filed Oct. 7, 1976 and now abandoned which in turn is a continuation-in-part of application Ser. No. 628,210, filed Nov. 3, 1975 and now abandoned.

BACKGROUND OF THE INVENTION

1. Field of the Invention

This invention relates to novel dibenzopyrans and more particularly to 1,9-dihydroxy-hexahydrodibenzopyrans having in the 3-position (1) an aryl or cycloalkyl group (W) linked to said position by an alkylene group; or (2) a methyl, aryl or cycloalkyl group linked to said position via (a) O, S, SO or $SO_2$ groups; or (b) an alkylene group interrupted by an O, S, SO or $SO_2$ group; or (c) an alkylene group attached to said 3-position or to said methyl, aryl or cycloalkyl groups by O, S, SO or $SO_2$; to intermediates therefor and derivatives thereof; and to the use of such dibenzopyrans and derivatives thereof as analgesic, hypotensive, antisecretory and anti-anxiety agents, as immunosuppressants and tranquilizers in mammals, including man.

2. Description of the Prior Art

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesic agents such as d-propoxyphene, codeine, and morphine, posess addictive liability. The need for improved and potent analgesic agents is, therefore, evident.

The analgesic properties of 9-nor-9β-hydroxyhexahydrocannabinol and of other cannabinoid structures, such as $\Delta^8$-tetrahydrocannabinol ($\Delta^8$-THC) and its primary metabolite, 11-hydroxy-$\Delta^8$-THC have been reported by Wilson and May, *Absts, Papers, Am. Chem. Soc.*, 168 Meet., MEDI 11(1974), and *J. Med. Chem.*, 17, 475–476 (1974).

U.S. Pat. No. 3,507,885 and 3,636,058, issued Apr. 21, 1970 and Jan. 18, 1972, respectively, describe various 1-hydroxy-3-alkyl-6H-dibenzo[b,d]pyrans having at the 9-position substituents such as: oxo, hydrocarbyl and hydroxy or chloro, hydrocarbylidene, and intermediates therefor.

U.S. Pat. No. 3,649,650, issued Mar. 14, 1972, discloses a series of tetrahydro-6,6,9-trialkyl-6H-dibenzo[b,d]pyran derivatives having at the 1-position an ω-dialkylaminoalkoxy group active as psychotherapeutic agents.

German Specification No. 2,451,934, published May 7, 1975, describes 1,9-dihydroxy-hexahydrodibenzo[b,d]pyrans and certain 1-acyl derivatives thereof having at the 3-position an alkyl or alkenyl group, as hypotensive, psychotropic, sedative and analgesic agents. The precursor hexahydro-9H-dibenzo[b,d]pyran-9-ones used in their preparation, and which are reported to have the same utility as the corresponding 9-hydroxy compounds, are described in German Specification No. 2,451,932, published May. 7, 1975.

German Specification No. 2,415,697, published Oct. 17, 1974, describes 1-hydroxy-6,6,9-trimethyl-hexahydrodibenzo[b,d]pyran derivatives,and intermediates therefor, having at the 3-position an aralkyl, (substituted aralkyl) or pyridylalkyl group. They are useful as analgesic agents and as mild tranquilizers.

U.S. Pat. No. 3,856,821, issued Dec. 24, 1974, describes a series of 3-alkoxy substituted dibenzo[b,d]pyrans having antiarthritic, antiinflammatory and central nervous system activity.

A stereospecific synthesis of (-)trans-6a,7,8,10a-tetrahydro-3-pentyl-6,6,9-trimethyl-6H-dibenzo[b,d]pyran-1-ol, more commonly known as (-)-$\Delta^1$-tetrahydrocannabinol, has been reported by Razdan et al. (*J. Am. Chem. Soc.*, 96, 5860—5, 1974). The process, a one-step synthesis, comprises the reaction of cis/trans-(+)-p-mentha-2,8-dien-1-ol with olivetol in the presence of 1% boron trifluoride etherate and anhydrous magnesium sulfate in methylene chloride at 0° C. The tetrahydro compound thus produced is converted to the corresponding 9-keto hexahydro compound by the procedure of Wildes et al., *J. Org. Chem.*, 36, 721-3 (1971). The procedure involves methylation of the 1-hydroxy-tetrahydro compound to its methyl ether and thence to the hydrogen chloride adduct by reaction with zinc chloride and HCl at 0° C. in chloroform. The adduct is then dehydrohalogenated by reaction with potassium tricyclopentylcarbinolate to give the corresponding 6a,7,8,9,10,10a-hexahydro-3-pentyl-6,6-dimethyl-9-methylene-6H-dibenzo[b,d]pyran-1-ol methyl ether. Oxidation of the 9-methylene group with potassium permanganate-periodate affords the 9-ketone. Demethylation of the methyl ether with pyridinium chloride or other acid reagent affords the alcohol.

Bergel et al., *J. Chem. Soc.*, 286–7 (1943) investigated the replacement of the pentyl group at the 3-position of 7,8,9,10-tetrahydro-3-pentyl-6,6,9-trimethyl-6H-dibenzo[b,d]pyran-1-ol by alkoxy (butoxy, pentoxy, hexoxy and octoxy) and found that it led to biological inactivity. The hexoxy derivative was reported to exhibit feeble hashish activity at 10 to 20 mg./kg. The remaining ethers showed no activity in doses up to 20 mg./kg.

In a more recent study, Loev et al., *J. Med. Chem.*, 16, 1200–6 (1973) report a comparison of 7,8,9,10-tetrahydro-3-substituted-6,6,9- trimethyl-6H dibenzo[b,d]pyran-1-ols in which the 3-substituent is $—OCH(CH_3)C_5H_{11}$: $—CH_2CH(CH_3)C_5H_{11}$ or $CH(CH_3)C_5H_{11}$. The ether side chain containing compound was 50% less active in central nervous system activity than the corresponding compound in which the alkyl side chain is directly attached to the aromatic ring, rather than through an intervening oxygen atom; and 5 times as active as the compound in which oxygen is replaced by methylene.

SUMMARY OF THE INVENTION

There has now been found a class of compound effective as analgesic, hypotensive, anti-secretory and anti-anxiety agents and an immunosuppressants and tranquilizers; namely, 1.9-dihydroxydibenzo[b,d]pyrans (formula I) which are non-narcotic and free of addition liability. Further, valuable intermediates (formulae II and III) for the preparation of said compounds and derivatives of said compounds useful as dosage forms (formula I, R ≠ hydrogen) have also been found. The compounds have the formulae

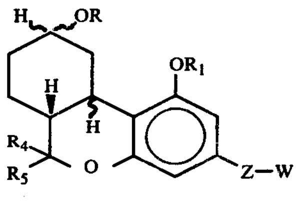

I

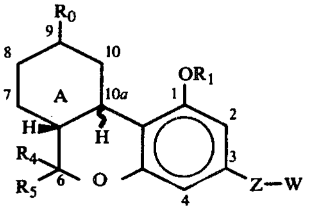

II and

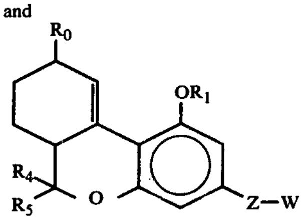

III wherein R is selected from the group consisting of hydrogen and alkanoyl having from one to five carbon atoms;

$R_1$ is selected from the group consisting of hydrogen, alkanoyl having from one to five carbon atoms and $—CO—(CH_2)_p—NR_2R_3$ wherein p is 0 or an integer from 1 to 4; each of $R_2$ and $R_3$ when taken individually is selected from the group consisting of hydrogen and alkyl having from one to four carbon atoms; $R_2$ and $R_3$ when taken together with the nitrogen to which they are attached form a 5- or 6-membered heterocyclic ring selected from the group consisting of piperidino, pyrrolo, pyrrolidino, morpholino, and N-alkylpiperazino having from one to four carbon atoms in the alkyl group;

each of $R_4$ and $R_5$ is selected from the group consisting of hydrogen, methyl and ethyl;

$R_0$ is selected from the group consisting of oxo and alkylenedioxy having from two to four carbon atoms;

Z is selected from the group consisting of (a) alkylene having from one to nine carbon atoms;

(b) $-(alk_1)_m-X-(alk_2)_n-$wherein each of $(alk_1)$ and $(alk_2)$ has from 1 to 9 carbon atoms, with the proviso that the summation of carbon atoms in $(alk_1)$ plus $(alk_2)$ is not greater than 9;

each of m and n is 0 or 1;

X is selected from the group consisting of O, S, SO and $SO_2$; and

W is selected from the group consisting of methyl, pyridyl, piperidyl,

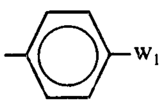

wherein $W_1$ is selected from the group consisting of hydrogen, fluoro and chloro; and

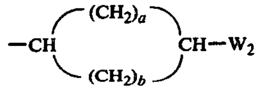

wherein $W_2$ is selected from the group consisting of hydrogen and

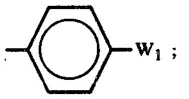

a is a integer from 1 to 5 and b is 0 or an integer from 1 to 5, with the proviso that the sum of a and b is not greater than 5;

with the proviso that when W is methyl, Z is $—(alk_1)_m—X—(alk_2)_n—$.

Compounds having the above formula contain asymmetric centers at the 6a- and/or 10a-positions. There may be additional asymmetric centers in the 3-position substituent (—Z—W), the 6-position and the 9-position. Diastereomers with the 9β-configuration are generally favored over the 9α-isomers because of greater (quantitatively) biological activity. Similarly, the trans (6,10a) diastereomers are favored over the cis (6a, 10a) diastereomers.

In the above formulae, the wavey lines are intended to depict the diastereomers at the 9- and the 6a,10a-positions.

In general, the optically active enantiomers containing the same absolute configuration at both the 6a- and 10a-positions as the natural cannabinols are favored because of greater (quantitatively) biological activity. The racemic modifications of these compounds can be used as such because they contain 50% of the more active enantiomer. The utility of the racemic mixtures, the diastereomeric mixtures as well as of the pure enantiomers and diastereomers is determined by the biological evaluations described below.

Although compounds of formula II are described herein as intermediates for compounds of formula I, many, particularly those wherein the C-9 substituent is oxo (=O), also exhibit analgesic and tranquilizer activity.

The preferred compounds of formula I are those wherein the OR group at the C-9 position has the β-configuration. Such compounds are of greater potency and efficady than are the corresponding α-compounds.

of special interest are compounds of formula I wherein the several variables have the significance shown below in Table A:

TABLE A

| OR | $OR_1$ | Z | m | n | W |
|---|---|---|---|---|---|
| β-OH | OH | alkylene having 1 to 6 carbon atoms | — | — | phenyl, pyridyl |
| β-OH | OH | $-(alk_1)_m-X-(alk_2)_n-$ | 1 | 1 | phenyl, pyridyl |
| β-OH | OH | $-(alk_1)_m-X-$ | 1 | — | phenyl, pyridyl |
| β-OH | OH | $-X-(alk_2)_n-$ | — | 1 | phenyl, pyridyl |

Particularly favored because of their potency are those compounds of formula I, Table A, wherein Z-W, the C-3 substituent, has the values shown in Table B below:

TABLE B:

| | |
|---|---|
| (a) | $-(CH_2)_q-C_6H_5$ |
| (b) | $-CH(CH_3)-(CH_2)_t-C_6H_5$ |
| (c) | $-[(CH_2)_q]_m-O-[(CH_2)_t]_n-C_6H_5$ |
| (d) | $-[CH(CH_3)-(CH_2)_q]_m-O-[CH(CH_3)-(CH_2)_t]_n-C_6H_5$ |
| (e) | $-[(CH_2)_q]_m-O-[(CH_2)_t]_n-CH_3$ |
| (f) | $-[CH(CH_3)-(CH_2)_q]_m-O-[CH(CH_3)-(CH_2)_t]_n-CH_3$ |

In the above table, each of q and t is an integer from 1 to 4and each of m and n is 0 or 1; with the proviso that only one of m and n is 0. Additionally, the intermediates for the above-mentioned compounds of interest (Tables A and B) and, in particular, the 6a,7-dihydro-6H-dibenzo[b,d]pyran-9(8H)-ones and the 6a,7,10,10a-tetrahydro-6H-dibenzo[b,d]pyran-9(8H)-ones of formula II and III are the preferred classes of intermediates by reason of their precursor relationship to the compounds of Tables A and B above.

DETAILED DESCRIPTION OF THE INVENTION

The compounds of this invention of formula III are readily prepared by ring annelation of the appropriate 5-$OR_1$-3-hydroxymethylene-2-$R_4R_5$-7-(Z-W)-4-chromanone with methyl vinyl ketone in the presence of a base; for example, an alkali metal hydroxide or alkoxide or a tertiary organic base such as triethylamine, to effect Michael addition, followed by treatment with a base, e.g., an alkali metal hydroxide or alkoxide (sodium or potassium hydroxide, ethoxide or methoxide) to complete aldol cyclization.

The resulting 6a,7-dihydro-1-$OR_1$-6,6-$R_4$,$R_5$-3-(Z-W)-6H-dibenzo[b,d]-pyran-9(8H)-one is then converted via Birch reduction to the corresponding 6aβ7,10,10aα-tetrahydro compound (formula II, $R_0$ = oxo). The reduction is conveniently carried out using lithium as the metal. Sodium or potassium can also be used. The reaction is conducted at a temperature of from about −35° C. to −80° C. The Birch reduction is favored because it offers stereoselectivity resulting in formulation of the desired trans-ketone of formula II.

Treatment of the compounds of formulae II and III wherein $R_0$ is oxo with the appropriate alkylene glycol having from two to four carbon atoms in the presence of a dehydrating agent such as p-toluenesulfonic acid, or other acid usd in ketalization (oxalic, adipic), affords the corresponding ketals.

Reduction of the 9-oxo groups of formulae II and III compounds ($R_0$ = oxo) via metal hydride reduction affords compounds of formula I (R = H). Representative of the metal hydrides useful for such conversion are lithium aluminum hydride, lithium borohydride and sodium borohydride. Sodium borohydride is favored as reducing agent in this step since it not only affords satisfactory yields of desired product, but reacts slowly enough with hydroxylic solvents (methanol, ethanol, water) to permit their use as solvents. A temperature of from about 0° C. to 30° C. is generally used. Lower temperatures, even down to about −70° C., can be used to increase selectivity of the reduction. Higher temperatures cause reaction of the sodium borohydride with the hydroxylic solvent. If higher temperatures are desired or required for a given reduction, isopropyl alcohol or the dimethyl ether of diethylene glycol are used as solvents Agents such as lithium borohydride or lithium aluminum hydride require anhydrous conditions and non-hydroxylic solvents (1,2-dimethoxyethane, tetrahydrofuran, ether, dimethyl ether of diethylene glycol).

The isomeric 9α- and 9β-hydroxy compounds are produced in this step. The above-described reaction sequence is summarized below.

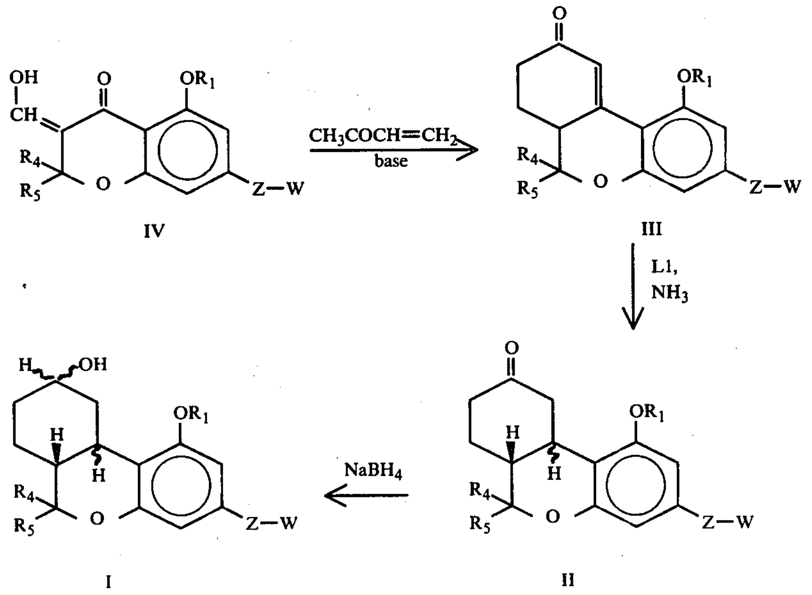

IV III II I (+ cis isomer)

The required 5-$OR_1$-3-hydroxymethylene-2-$R_4R_5$-7-(Z-W)-4-chromanones (IV) are prepared from 3,5-dihydroxybenzoic acid by the following abbreviated sequence:

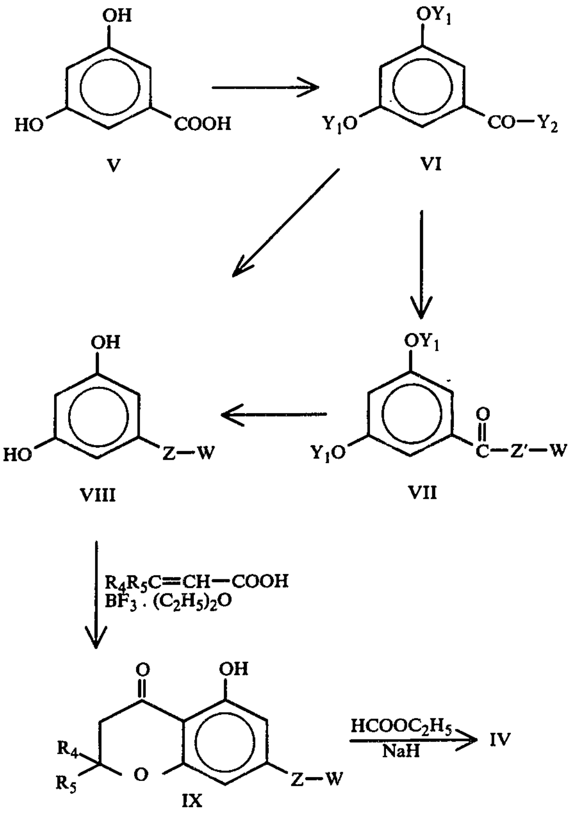

The starting material, 3,5-dihydroxybenzoic acid (V) is converted to a compound of formula (VI) wherein $Y_2$ represents an alkoxy group, desirably methoxy or ethoxy for ease of preparation, or an amino group; and $Y_1$ is a hydroxy protecting group, by methods described in the literature.

When Z is alkylene, $Y_1$ is desirably alkyl having from one to four carbon atoms or benzyl. The function of group $Y_1$ is to protect the hydroxy groups during subsequent reactions. It is its ability to perform a specific function; i.e., protection of the hydroxy groups, rather than its structure which is important. The selection and identification of appropriate protecting groups can easily and readily be made by one skilled in the art. The suitability and effectiveness of a group as a hydroxy protecting group are determined by employing such a group in the above-illustrated reaction sequence. It should, therefore, be a group which is easily removed to permit restoration of the hydroxy groups. Methyl is favored as a protecting alkyl group since it is easily removed by treatment with pyridine hydrochloride. The benzyl group, if used as a protecting group, is removed by catalytic hydrogenolysis or acid hydrolysis.

When Z is $-(alk_1)_m-X-(alk_2)_n-$, $Y_1$ is preferably benzyl or a substituted benzyl group since it can subsequently be removed without detriment to the Z group.

The diprotected benzoic acid derivative (VI) is then converted to a compound of formula VIII by known technology. In one procedure VI is hydrolyzed to the corresponding acid ($Y_2$ = OH), or lithium salt, and reacted with the appropriate alkyl lithium to produce an alkyl disubstituted phenyl ketone ($Y_2$ = alkyl). When methyl lithium is used, the resulting acetophenone derivative is treated with a Grignard Reagent (W—Z'—MgBr). The intermediate adduct is hydrolyzed to the corresponding alcohol which is then hydrogenolyzed to replace the hydroxy group with hydrogen. This procedure is especially useful for those compounds wherein Z is alkylene.

The ether groups are deblocked by suitable means: treatment with pyridine hydrochloride ($Y_1$ = methyl) or catalytic hydrogenolysis ($Y_1$ = benzyl), or by treatment with an acid such as trifluoroacetic acid, hydrochloric, hydrobromic or sulfuric acids, or pyridine hydrochloride. Acid debenzylation is, of course, used when the group -Z-W contains sulfur.

A further method for converting compounds of formula VI to those of formula VIII comprises reaction of a ketone of formula VI ($Y_2$ = alkyl) with the appropriate triphenyl phosphonium bromide derivative $[(C_6H_5)_3P^+\text{-Z-W}]Br^-$ in the presence of a base (e.g., sodium hydride). The reaction proceeds via an alkene which is subsequently catalytically hydrogenated to the corresponding alkane (Z-W) and deblocked to the dihydroxy compound (VIII). Of course, when —Z— is $(alk_1)_m-X-(alk_2)_n$ and $Y_1$ is benzyl, the catalytic hydrogenation also results in cleavage of the benzyl ethers.

Alternatively, conversion of structure VI compounds to those of structure VIII can be achieved by the sequence VI → VII → VIII. In this sequence, the diprotected benzamide (VI, $Y_2 = NH_2$) is converted to the ketone (VII, Z' = Z less one $CH_2$ group) by reaction with the appropriate Grignard reagent (BrMg-Z'-W) followed by reaction with methyl- or ethyl-magnesium halide to form the corresponding carbinol. Dehydration of the carbinol, e.g. with p-toluenesulfonic acid, affords the corresponding alkene which is then catalytically hydrogenated (Pd/C) to the alkane (VIII). The ether groups are deblocked (converted to hydroxy) as described above.

The conversion of VIII to the 4-chromanone (IX) is achieved by the reaction of VIII with crotonic acid or an acid of the formula $R_4R_5-C{=}CH-COOH$ in the presence of boron trifluoride etherate at from about 20° to about 125° C. In addition to structure IX products, a second product, isomeric to IX (7-hydroxy-2,2-$R_4R_5$-5-Z-W-4-chromanone), is also produced.

The 4-chromanones of formula IX are then converted to hydroxymethylene derivatives of formula IV by reaction with ethyl formate and sodium hydride.

Compounds of formula VIII wherein —Z—W is -alkylene-W or $-(alk_1)-X'-(alk_2)_n-W$ wherein $(alk_1)$, $(alk_2)$, W and n are as defined above and X' is O or S, are obtained by the following sequence:

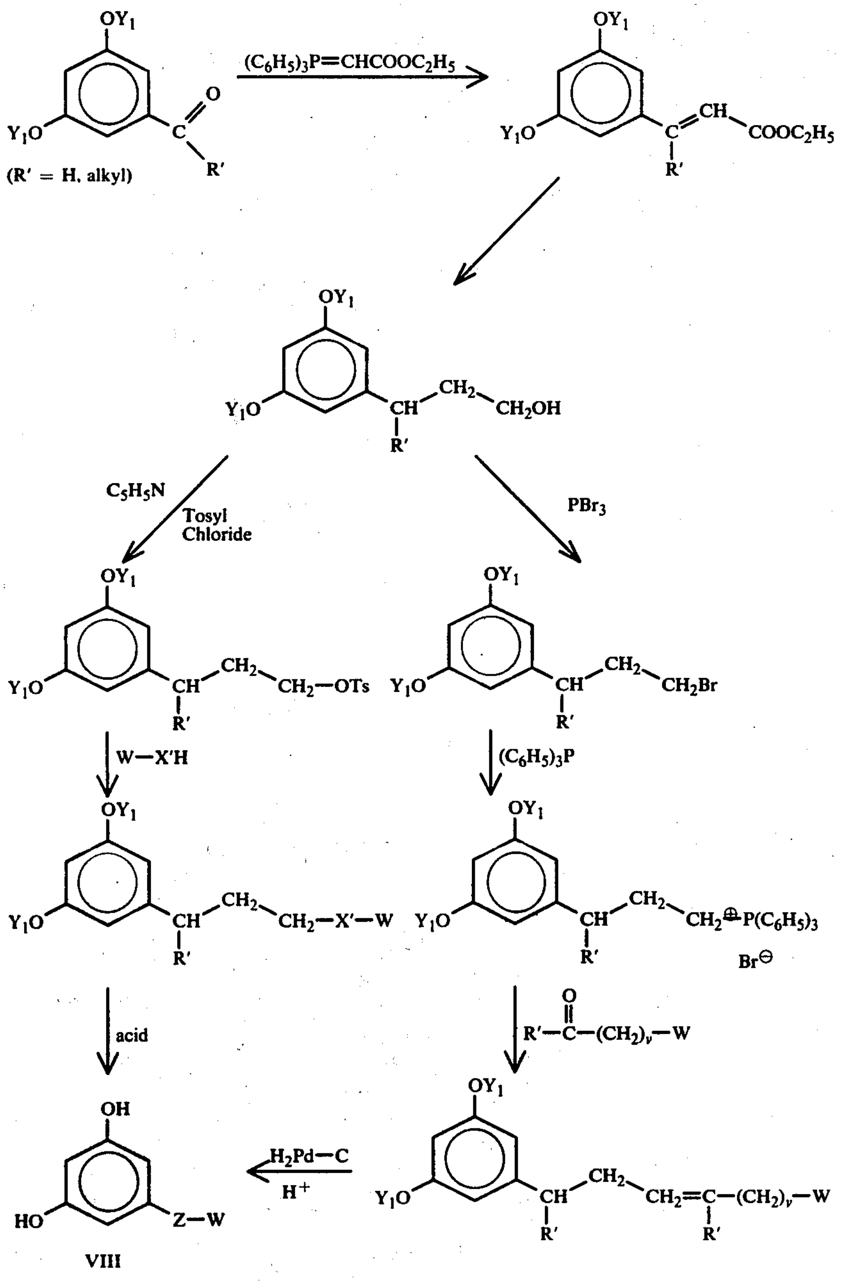

VIII

The first step in the above sequence (the Wittig reaction) provides opportunity, by choice of appropriate reactants, to produce compounds having straight or branched alkylene groups. In the given illustration, the value of R' as methyl or ethyl permits formation of a compound having alkyl substitution on the carbon atom (α) adjacent to the phenyl group. Substitution of a methyl or ethyl group at other sites, e.g., the β-carbon atom of the alkylene group, is achieved by choice of the appropriate carboalkoxy alkylidene triphenylphosphorane, e.g., $(C_6H_5)_3P{=}C(R')—COOC_2H_5$. The unsaturated ester thus produced is reduced to the corresponding saturated alcohol by reaction with lithium aluminum hydride, generally in the presence of a small amount of aluminum chloride. Alternatively, when $Y_1$ is other than benzyl (e.g. methyl), the alcohol is produced by catalytic reduction of the unsaturated ester using palladium-carbon, followed by treatment of the saturated ester thus produced with lithium aluminum hydride. Conversion of the alcohol to the corresponding tosylate or mesylate followed by alkylation of the tosylate or mesylate with an alkali metal salt of the appropriate HX'—(alk$_2$)-W reactant, and finally removal of the protecting groups ($Y_1$) affords the desired resorcinol. When X' is sulfur, the protecting group is methyl.

A variation of the above sequence comprises bromination of the alcohol rather than converting it to a tosylate or mesylate. Phosphorous tribromide is a convenient brominating agent. The bromo derivative is then reacted with the appropriate HX'—(alk$_2$)—W in the presence of a suitable base (Williamson reaction).

The bromo compounds also serve as valuable intermediates for increasing the chain length of the alkylene moiety in the above sequence to give compounds wherein Z is -alkylene-W. The process comprises treating the bromo derivative with triphenyl phosphine to produce the corresponding triphenylphosphonium bromide. Reaction of the triphenylphosphonium bromide with the appropriate aldehyde or ketone in the presence of a base such as sodium hydride or n-butyl lithium affords an unsaturated derivative which is then catalytically hydrogenated to the corresponding saturated compound.

In this variation, the value of the protecting group ($Y_1$) selected depends upon the particular sequence followed. When the vertical sequence on the right is used, benzyl is the preferred protecting group by reason of the catalytic hydrogenation step. Methyl is the preferred protecting group when the left vertical sequence is followed, since it is conveniently removed by treatment with acid as described herein.

Compounds of formula II wherein —Z—W is $—(alk_1)_m—X—(alk_2)_n—W$ and X is —SO— or $—SO_2—$ are obtained by oxidation of corresponding compounds in which X is —S—. Hydrogen peroxide is a convenient agent for oxidation of the thio ethers to sulfoxides. Oxidation of the thio ethers to corresponding sulfones is conveniently accomplished by means of a peracid such as perbenzoic, perphthalic or m-chloroperbenzoic acid. This latter peracid is especially useful since the by-product m-chlorobenzoic acid is easily removed.

Alternatively, the compounds of this invention can be prepared according to the procedure described by Fahrenholtz, et al., *J. Am. Chem. Soc.*, 89, 5934–5941 (1967). This process comprises Von Pechmann condensation of the appropriate —Z—W substituted 3,5-dihydroxybenzene with diethyl-α-acetoglutarate in the presence of phosphorous oxychloride. The ethyl-5-hydroxy-4-methyl-7-(Z-W)-coumarin-3-propionate thus produced is then cyclized to 7,10-dihydro-1-hydroxy-3-(Z-W)-6H-dibenzo[b,d]pyran-6,9(8H)-dione by reaction with sodium hydride in dimethylsulfoxide. The dibenzo[b,d]-pyran thus produced is converted to the corresponding 9-ketal derivative by reaction with ethylene glycol and p-toluenesulfonic acid. Treatment of the ketal with the appropriate alkyl magnesium iodide followed by acid hydrolysis affords dl-6a,7-dihydro-1-hydroxy-6,6-dialkyl-3-(Z-W)-6H-dibenzo[b,d]pyran-9(8H)-one. Birch reduction of the thus-produced dihydro compound provides the corresponding tetrahydro compound, which is converted to the 1,9-dihydroxy having formula I by reduction with sodium borohydride as described above.

A further method for making compounds of formula VIII wherein Z—W is $(alk_1)—X—(alk_2)—W$ comprises reaction of the appropriate 3,5-(di-protected hydroxy)styrene oxide with an alcohol or thio alcohol $(HX—(alk_2)—W)$ as its alkali metal (preferably sodium or potassium) salt. Methyl is a favored protecting group for the 3,5-dihydroxy styrene oxides because of its ease of removal. The resulting 3,5-(di-protected hydroxy)phenyl hydroxyalkyl ether compound (formula VIII-A) is converted to the corresponding alkyl ether (formula VIII-B) by treatment with phosphorous oxychloride followed by dehalogenation of the thus produced chloro derivative by means of hydrogen over palladium. Removal of the protecting groups as described above affords the desired compound. The reaction sequence is presented below ($Y_1$ = benzyl, alkyl having one to four carbon atoms; X' is O, S; R' = H, $CH_3$, $C_2H_5$ and may be alike or different).

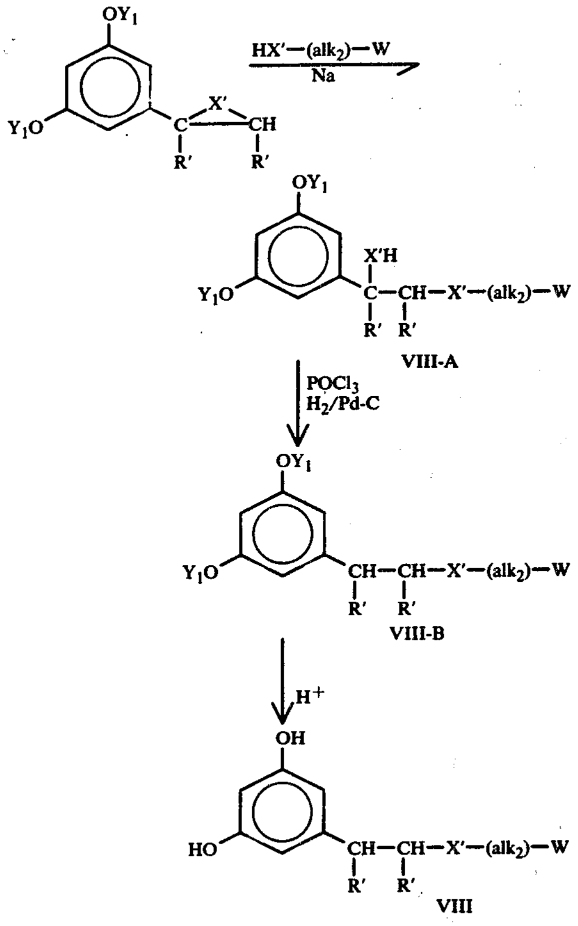

VIII-A

VIII-B

VIII

Esters of compounds of formulae II and III wherein $R_1$ is alkanoyl or $—CO—(CH_2)_p—NR_2R_3$ are readily prepared by reacting formula II or III compounds with the appropriate alkanoic acid or acid of formula $HOOC—(CH_2)_p—NR_2R_3$ in the presence of a condensing agent such as dicyclohexylcarbodiimide. Alternatively, they are prepared by reaction of a formula II or III compound with the appropriate alkanoic acid chloride or anhydride, e.g., acetyl chloride or acetic anhydride, in the presence of a base such as pyridine.

Esters of formula I compounds in which each of the R and $R_1$ groups is esterified are prepared by acylation according to the above-described procedures. Compounds in which only the 9-hydroxy group is acylated are obtained by mild hydrolysis of the corresponding 1,9-diacyl derivative, advantage being taken of the greater ease of hydrolysis of the phenolic acyl group. Formula I compounds in which only the 1-hydroxy group is esterified are obtained by borohydride reduction of the corresponding formula II ketone esterified at the 1-position. The thus-produced formula I compounds bearing 1-acyl-9-hydroxy substitution or 1-hydroxy-9-acyl substitution can then be acylated further with a different acylating agent to produce a diesterified compound of formula I in which the ester group at the 1- and the 9-positions are different.

The analgesic properties of the compounds of this invention are determined by tests using nociceptive stimuli.

TESTS USING THERMAL NOCICEPTIVE STIMULI

(a) Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a ⅛" thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6 ½" diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an $MPE_{50}$= 4–5.6 mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941), using controlled high intensity heat applied to the tail. Each mouse is placed in a snug-fitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure

The method is a modification of the receptacle procedure developed by Benbasset, et al., *Arch. int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

TEST USING CHEMICAL NOCICEPTIVE STIMULI

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or 50 minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drug pretreatments in blocking writhing are ascertained.

TESTS USING PRESSURE NOCICEPTIVE STIMULI

Effect on the Haffner Tail Pinch Procedure

A modification of the procedure of Haffner, *Experimentelle Prufung Schmerzstillender. Mittel Deutch Med. Wschr.*, 55, 731–732 (1929) is used to ascertain the effects of the test compound on aggressive attacking responses elicited by a stimulus pinching the tail. Male albino rats (50–60b.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg. (i.p.).

TESTS USING ELECTRICAL NOCICEPTIVE STIMULI

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensitis are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% \text{ MPE} = \frac{\text{test time} - \text{control time}}{\text{cutoff time} - \text{control time}} \times 100$$

The compounds of the present invention are active analgesics via oral and parenteral administration and are conveniently administered in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, solutions, emulsions, syrups and elixirs which may contain flavoring and coloring agents. For oral administration of the therapeutic agents of this invention, tablets or capsules containing from about 0.01 to 100 mg. are suitable for most applications.

The physician will determine the dosage which will be most suitable for an individual patient and it will vary with the age, weight and response of the particular patient and the route of administration. Generally, however, the initial analgesic dosage in adults may range from 0.01 to 500 mg. per day in single or divided doses. In many instances, it is not necessary to exceed 100 mg. daily. The favored oral dosage range is from about 0.01 to about 300 mg./day; the preferred range is from about 0.10 to about 50 mg./day. The favored parenteral dose is from about 0.01 to about 100 mg./day; the preferred range from about 0.01 to about 20 mg./day.

By means of the above procedures, the analgesic activity of several compounds of this invention and of certain prior art compounds are determined. The data are reported in terms of maximum possible effect.

The following abbreviations are used in tables:

PBQ = phenylbenzoquinone-induced writhing; TF = tail flick; HP = hot plate; RTC = rat tail clamp; FJ = flinch jump; and TI = tail immersion assays.

TABLE I.

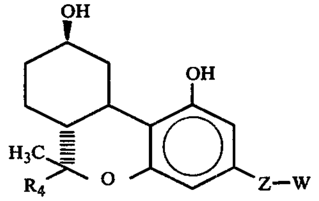

| ANALGESIC ACTIVITY ($ED_{50}$- mg./kg.) | | | | | RTC | FJ | TI |
|---|---|---|---|---|---|---|---|
| $R_4$ | $-Z-W$ | PBQ | TF | HP | 1 hour | 2 hours | ½ hour |
| $CH_3$ | $-(CH_2)_2-C_6H_5$ | | | | N.T. | N.T. | N.T. |
| $CH_3$ | $-CH(CH_3)-(CH_2)_2-C_6H_5$ | 5.0 | >10 | >10 | N.T. | N.T. | N.T. |
| $CH_3$ | $-CH(CH_3)-(CH_2)_3-C_6H_5$ | 0.062 | 0.32 | 0.75 | 1.8 | 0.11 | 0.30 |
| $CH_3$ | $-CH(CH_3)-(CH_2)_4-C_6H_5$ | 1.33 | 2.8 | 3.9 | <3.2 | 0.42 | 3.5 |
| H | $-CH(CH_3)-(CH_2)_3-C_6H_5$[a] | 0.94 | 1.6 | 5.6 | N.T. | N.T. | N.T. |
| H | $-CH(CH_3)-(CH_2)_3-C_6H_5$[b] | | | | | | |
| $CH_3$ | $-O-CH(CH_3)-(CH_2)_2-C_6H_5$ | 0.21 | 1.3 | ~3.2 | N.T. | N.T. | N.T. |
| $CH_3$ | $-O-CH(CH_3)-(CH_2)_3-C_6H_5$ | 0.11 | 0.33 | 0.76 | 1.9 | 0.44 | 0.40 |
| $CH_3$ | $-CH(CH_3)-(CH_2)_3-O-C_6H_5$ | 0.39 | 1.2 | ~10 | N.T. | N.T. | N.T. |
| $CH_3$ | $-O-CH(CH_3)-C_5H_{11}$ | 0.16 | 0.46 | 1.2 | 0.34 | 0.30 | 0.70 |
| $CH_3$ | $-O-C_6H_{11}$ | 5.3 | >10 | >10 | N.T. | N.T. | N.T. |
| $CH_3$ | $-C_5H_{11}$ | 0.68 | 3.2 | ≧17.8 | 58 | 8 | 13 |
| $CH_3$ | $-CH(CH_3)-CH(CH_3)-C_5H_{11}$ | 0.10 | 0.35 | 1.1 | 0.44 | 0.11 | 0.38 |
| $CH_3$ | $-CH(CH_3)-(CH_2)_2-O-C_6H_5$ | 0.1-1.0 | | | | | |
| $CH_3$ | $-CH_2(CH_3)-(CH_2)_3-$4-pyridyl | 0.17 | | | | | |
| morphine | | 0.8 | 3.8 | 4.7 | 2.9 (½ hr.) | N.T. | 4.0 |

[a]Component A of Example 5, 5th compound
[b]Component B of Example 5, 5th compound

TABLE II.

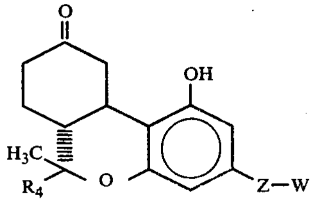

| ANALGESIC ACTIVITY ($ED_{50}$- mg./kg.) | | | | | | | |
|---|---|---|---|---|---|---|---|
| $R_4$ | $-Z-W$ | PBQ | TF | HP | RTC | FJ | TI |
| $CH_3$ | $-(CH_2)_2-C_6H_5$ | | | | | | |
| $CH_3$ | $-CH(CH_3)-(CH_2)_2-C_6H_5$ | | N.T. | N.T. | N.T. | N.T. | N.T. |
| $CH_3$ | $-CH(CH_3)-(CH_2)_3-C_6H_5$ | 6.0 | 5.6-10 | >10 | N.T. | N.T. | N.T. |
| $CH_3$ | $-CH(CH_3)-(CH_2)_4-C_6H_5$ | | 10 | >10 | N.T. | N.T. | N.T. |
| H | $-CH(CH_3)-(CH_2)_3-C_6H_5$[b] | 3.0 | 7.5-10 | 10-32 | N.T. | N.T. | N.T. |
| $CH_3$ | $-O-CH(CH_3)-(CH_2)_2-C_6H_5$ | | >10 | >10 | N.T. | N.T. | N.T. |
| $CH_3$ | $-O-CH(CH_3)-(CH_2)_3-C_6H_5$ | 1.3 | 3.6 | >10 | N.T. | N.T. | N.T. |
| $CH_3$ | $-CH(CH_3)-(CH_2)_3-O-C_6H_5$ | 10-15 | >10 | >10 | N.T. | N.T. | N.T. |
| $CH_3$ | $-O-CH(CH_3)-C_5H_{11}$ | 2.6 | N.T. | N.T. | N.T. | N.T. | N.T. |
| $CH_3$ | $-O-C_6H_{11}$ | | | | | | |
| $CH_3$ | $-CH(CH_3)-(CH_2)_3-(4-C_5H_4N)$ | 0.86 | 1-3.2 | >5.6 | N.T. | N.T. | N.T. |
| $CH_3$ | $-C_5H_{11}$ | >56 | >56 | | | | |
| $CH_3$ | $-CH(CH_3)-CH(CH_3)-C_5H_{11}$ | 0.24 | 1.25 | 5.6 | 3.2 | 0.66 | 3.2 |

TABLE II.-continued

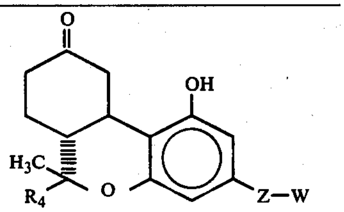

| ANALGESIC ACTIVITY ($ED_{50}$- mg./kg.) | | | | | | | |
|---|---|---|---|---|---|---|---|
| $R_4$ | —Z—W | PBQ | TF | HP | RTC | FJ | TI |
| $CH_3$ | $—CH(CH_3)—(CH_2)_2—O—C_6H_5$ | 5-10 | | | | | |

[(b)]a mixture of 2 diasteriomers

Their antihypertensive utility is determined by their ability to lower the blood pressure of conscious hypertensive rats and dogs a statistically significant degree when administered orally to said hosts at the above-mentioned dosages.

Their tranquilizer activity is demonstrated by oral administration to rats at doses of from about 0.01 to 50 mg./kg. with subsequent decreases in spontaneous motor activity. The daily dosage range in mammals is from about 0.1 to about 100 mg.

In addition to their analgesic, hypotensive and tranquilizer activities, compounds of formula I are also useful as immunosuppressants and antisecretory agents.

Their gastric antisecretory effect in pouch dogs (Heidenhain) is determined by the following procedure.

Gastric antisecretory activity is studied in overnight fasted, conscious Heidenhain pouch dogs using pentagastrin, histamine or food to stimulate acid output. Pentagastrin or histamine is administered as a continuous infusion into a superficial leg vein at doses earlier determined to stimulate near maximal acid output from the gastric pouch. Food stimulus consists of one-half can of Ken-L-Ration (approx. 220 g.) per dog; dogs weighing 9–12.5 kg. are used. Gastric juice is collected at 30 minute intervals following the start of a histamine or pentagastrin infusion or the ingestion of a standard food meal. A total of ten collections are made for each dog during an experiment. Drug is administered orally at levels of from 0.01 to 50 mg./kg. after the third gastric juice collection. All sample volumes are recorded and acid concentration is determined by titrating sample aliquots (1.0 ml.) to pH 7.4 with 0.1N NaOH using a pH meter (Radiometer) and autoburette. The drug is given orally afer placing it in gelatin capsules.

Immunosuppressant activity is evaluated by means of a mixed lymphocyte culture assay procedure. This assay measures the effects of the test compounds on antigen-stimulated lymphocyte proliferation. Spleen lymphoid cells from BALB/C and C57BL/6 mice, $8 \times 10^6$ cells from each strain, are suspended in 2.0 ml. of a serum-free medium containing the test compound and incubated at 37° C. in a 10% carbon dioxide atmosphere. The culture conditions and technique are described by R. W. Dutton in *J. Exp. Med.*, 122, 759 (1965) and the cellular medium is described by W. T. Weber in *J. Retic. Soc.*, 8, 37 (1970) Half of the medium, 1 ml., is replaced with fresh medium every 24 hours. $^3$H-TdR incorporation (24 hour pulse) into desoxyribonucleic acid is then determined by trichloroacetic acid precipitation of desoxyribonucleic acid and assessment of radioactivity in a liquid scintillation counter. The percent inhibition is determined by comparing each test compound-treated mixed culture with the control mixed culture.

EXAMPLE 1 dl-5-Hydroxy-2,2-dimethyl-7-(1-methyl-4-phenylbutyl)-4-chromanone

A mixture of 2-(3,5-dihydroxyphenyl)-5-phenylpentane (9.6 g.) and 3-methylcrotonic acid (4.5 g.) is heated to 125° C. under nitrogen, and boron trifluoride etherate (8.7 ml.) is added. After refluxng for 1 hour, the reaction is cooled and water (10 ml.) is added followed by 6N sodium hydroxide (40ml.). The reaction mixture is heated for 5 minutes on a steam bath, cooled and acidified with 6N hydrochloric acid. The aqueous layer is extracted with ether ($3 \times 100$ ml.) and the combined ether extracts washed with 10% sodium bicarbonate ($1 \times 25$ ml.) and water ($1 \times 25$ ml.). The organic phase is dried over sodium sulfate and concentrated under vacuum to afford 12.7 g. of a crude oil which is purified by silica gel chromatography to yield 5.0 g. of dl-5-hydroxy-2,2-dimethyl-7-(1-methyl-4-phenylbutyl)-4-chromanone as a colorless oil.

IR: ($CHCl_3$) C=O 1635 $cm^{-1}$.

NMR: $\delta_{CDCl_3}^{TMS}$ 1-1.7 (M,7,α-methyl, ethylene), 1.5 (S, 6,gem dimethyl), 2.3–2.9 (M,3,benzylic-methylene, methinyl), 2.65 (S,2,α-methylene), 6.1–6.35 (M,2,aromatic), 6.9 -7.4 (M,5,aromatic), 11.53, 11.63 (d,l, hydroxyl).

Similarly, 2-(3,5-dihydroxyphenyl)-6-phenylhexane is converted to dl-5-hydroxy-2,2-dimethyl-7-(1-methyl-5-phenylphenyl)-4-chromanone (an oil):

NMR: $\delta_{CDCl_3}^{TMS}$ 1.2 (d,3,α-methyl, J = 7 cps), 1.4 (S,6gem dimethyl), 1.0–1.9 [M,6,Φ—$CH_2$—$(CH_2)_3$—C($CH_3$)—Ar], 2.3–2.8 (M,3,benzylic-methylene, methinyl), 2.7 (S,2,α-methylene), 6.2–6.4 (M,2,aromatic), 7.1–7.3 (M,5,aromatic), 11.6 (S,1,hydroxyl); 1-(3,5-Dihydroxyphenyl)-2-phenylethane is converted to 5-hydroxy-2,2-dimethyl-7-(2-phenylethyl)-4-chromanone (an oil):

IR: ($CHCl_3$) C=O 1645 $cm^{-1}$

NMR: $\delta_{CDCl_3}^{TMS}$ 1.45 (S,6,gem dimethyl), 2.65 (S, 2,α-methylene), 2.85 (S,4,ethylene), 6.25, 6.3 (2s,2,aromatic), 7.2 (S,5,aromatic), 11.6 (S,1,hydroxyl-$D_2O$ overlay).

MS : (mol.ion) 296

2-(3,5-Dihydroxyphenyl)-4-phenylbutane is converted to dl-5-hydroxy-2,2-dimethyl-7-(1-methyl-3-phenylpropyl)-4-chromanone (an oil):

NMR: $\delta_{CDCl_3}^{TMS}$ 1.3 (d,3,methyl), 1.45 (S,6,gem dimethyl), 1.55–2.1 (M,2,methylene), 2.25-2.75 (M,3,benzylic-methylene, methinyl),6.15 (d,2,aromatic), 7.1 (S,5,aromatic), 11.6 (S,1,hydroxyl-$D_2O$ overlay).

MS: (mol.ion) 324

2-(3,5-dihydroxyphenyl)-5-phenylpentane (5.27 g.) is converted by reaction with boron trifluoride etherate (4.81 ml.) and crotonic acid (2.08 g. of freshly distilled) in place of 3-methylcrotonic acid to dl-5-hydroxy-2-methyl-7-(1-methyl-4-phenylbutyl)-4-chromanone:

NMR: $\delta_{CDCl_3}^{TMS}$ 1.1 (D,3,α-methyl, J = 7 Hz), 1.4 (D,3.2-methyl, J = 7 Hz), 1.3–1.8 (M,4-ethylene), 2.2–2.9 (M,5,α-methylene, benzylic-methylene, methinyl), 4.5 (M,1,methinyl ether), 6.1, 6.2 (2D,2,aromatic, J = 1 Hz), 6.9–7.4 (M,5,aromatic), 11.7 (S,1,phenolic OH).

4-(3,5-dihydroxyphenyl)-1-phenoxypentane is converted to dl-5-hydroxy-2,2-dimethyl-7(1-methyl-4-phenoxybutyl)-4-chromanone, a light yellow oil:

MS: (mol.ion) 354

$R_f$ = 0.61 (silica gel, 18-benzene:1-ethyl acetate)

Analysis: Calc'd for $C_{22}H_{26}O_4$: C, 74.55; H, 7.39%. Found: C, 74.56; H, 7.36%.

4-(3,5-dihydroxyphenyl)-1-(4-pyridyl)pentane is converted to dl-5-hydroxy-2,2-dimethyl-7-[1-methyl-4-(4-pyridyl)butyl]-4-chromanone, an oil:

$R_f$ = 0.39 (silica gel, 1-benzene:1-ethyl acetate)

NMR: $\delta_{CDCl_3}^{TMS}$ 1-1.90 (M,13-H,methylene,methyl doublet at 1.20,J = 7 Hz, and gem dimethyl singlet at 1.5); 2.43–2.86 (M,5-H,methylene, methinyl, including singlet (two C-3 H's at 2.71); 6.26 (b.d.S,1-H,aromatic); 6.33 (b.d.S,1-H,aromatic); 7.00–7.20 (b.d.D,2-H,pyridine aromatic); 7.25 (b.d.S,1-H,hydroxyl); 8.41–8.61 (b.d.D,2-H,pyridine aromatic).

dl-5-hydroxy-2,2-dimethyl-7-(1-methyl-3-phenoxypropyl)-4-chromanone is prepared from 3-(3,5-dihydroxyphenyl)-1-phenoxybutane as an oil.

$R_f$ = 0.7 (silica gel, 18-benzene:1-ethyl acetate)

MS: (mol.ion) 340

Analysis: calc'd for $C_{21}H_{24}O_4$: C, 74,09; H, 7.11%. Found: C, 74.04; H, 7.19%.

dl-2-(3,5-Dihydroxyphenyl)-1-(2-phenylethoxy)propane is converted to dl-2,2-dimethyl-5-hydroxy-7-[1-methyl-2-(2-phenylethoxy)ethyl]-4-chromanone (an oil).

NMR: $\delta_{CDCl_3}^{TMS}$ 1.21 (d, J=7Hz, methyl), 1.48 (s, gem dimethyl), 2.73 (s, C-3 methylene), 2.86 (+, J=7Hz, $CH_2Ph$), 2.9 (m, methine), 3.50 (d, J=7Hz, $—CH_2O—$), 3.65 (t, J=7Hz, $—OCH_2—$), 6.31 (d, J=1Hz, ArH), 6.38 (d, J=1 Hz, ArH), 7.26 (s, Ph) and 13.33 (s, phenol).

EXAMPLE 2 dl-5-Hydroxy-3-hydroxymethylene-2,2-dimethyl-7-(1-methyl-4-phenylbutyl)-4-chromanone To sodium hydride obtained by washing 50% sodium hydride in mineral oil dispersion (6.67 g.) with pentane is added dropwise, over a 30-minute period, a solution of dl-5-hydroxy-2,2-dimethyl-7-(1-methyl-4-phenylbutyl)-4-chromanone (4.7 g.) and ethyl formate (23.1 g.). The reaction mixture is then cooled to room temperature and ether (350 ml.) added. The resulting mixture is refluxed for 18 hours, cooled to room temperature and acidified with 1N hydrochloric acid. The ether layer is separated and the water layer extracted with ether (3 × 100 ml.). The combined ether extracts are dried over sodium sulfate and concentrated under vacuum to yield 5.7 g. of dl-5-hydroxy-3-hydroxymethylene-2,2-dimethyl-7-(1-methyl-4-phenylbutyl)-4-chromanone as an oil.

NMR: $\delta_{CDCl_3}^{TMS}$ 1.05–1.8 (M,13,gem dimethyl, α-methyl, ethylene), 2.45 (M,3,benzylic-methylene, methinyl), 6.2–6.5 (M2,aromatic), 7.0–7.6 (M,6,aromatic, methinyl ether), 11.3, 11.36 (2bd.S, 1,phenolic hydroxyl), 13.3, 13.5 (2bd. S, 1,hydroxyl).

IR: ($CHCl_3$) C=O 1625 $cm^{-1}$

In like manner, the products of Example 1 are converted to:

dl-5-hydroxy-3-hydroxymethylene-2,2-dimethyl-7-(1-methyl-5-phenylpentyl)-4-chromanone:

NMR: $\delta_{CDCl_3}^{TMS}$ 1.2 (D,3,α-methyl,J = 7 cps), 1.6 (S,6,gem dimethyl), 1.0–2.0 [M,6,$\Phi CH_2—(CH_2)_3—CH(CH_3)Ar$], 2.3–2.8 (M,3,benzylic-methylene, methinyl), 6.2–6.4 (M,2,aromatic), 7.1–7.4 (M,6,-aromatic, vinylic), 11.4 (bd.S,1 phenolic hydroxyl);

5-hydroxy-3-hydroxymethylene-2,2-dimethyl-7-(2-phenylethyl)-4-chromanone (an oil):

IR: ($CHCl_3$) C=O 1625 $cm^{-1}$

NMR: $\delta_{CDCl_3}^{TMS}$ 1.5(S,6,gem dimethyl), 2.85 (S,4,ethylene), 6.2, 6.3 (d,2,aromatic), 7.0–7.5(M,-6,aromatic, methinyl), 11.35 (S,1,hydroxyl-$D_2O$ overlay), 13.4, 13.6 (d,1,hydroxyl-$D_2O$ overlay).

MS: (mol.ion) 324 dl-5-hydroxy-3-hydroxymethylene-2,2-dimethyl-7-(1-methyl-3-phenylpropyl)-4-chromanone (an oil):

NMR: $\delta_{CDCl_3}^{TMS}$ 1.15 (d,3,methyl), 1.5 (S,6,gem dimethyl), 1.65–2.1 (M,2,methylene), 2.25–2.75 (M,3,benzylic-methylene, methinyl), 6.15, 6.3 (2d, 2,aromatic), 7.1 (M,6,aromatic, olefinic proton), 11.3 (S,1,hydroxyl-$D_2O$ overlay), 1.3., 13.8 (d,1,hydroxyl-$D_2O$ overlay).

MS: (mol.ion) 352 dl-5-hydroxy-3-hydroxymethylene-2-methyl-7-(1-methyl-4-phenylbutyul)-4-chromanone:

NMR: $\delta_{CDCl_3}^{TMS}$ 1.1 (D,3,α-methyl, J = 7 Hz), 1.5 (D,3,2-methyl, J = 7 Hz), 1.3–1.8 (M,4-ethylene), 2.3–2.9 (M,3,benzylic), 4.9 (M,1,methinyl ether, J = 5 Hz), 6.2, 6.3 (2D,2,aromatic, J = 1 Hz), 6.9–7.4 (M,6,aromatic, vinylic), 11.2 (bc.S, 1,phenolic OH).

dl-5-hydroxy-2,2-dimethyl-7-(1-methyl-4-phenoxybutyl)-4-chromanone is converted to d,1-5-hydroxy-3-hydroxymethylene-2,2-dimethyl-7-(1-methyl-4-phenoxybutyl)-4-chromanone: $R_f$ = 0.44 [silica gel, 18-benzene:1-ethyl acetate]

MS: (mol.ion) 382 dl-5-hydroxy-2,2-dimethyl-7-[1-methyl-4-(4-pyridyl)-butyl]-4-chromanone is converted to d,1-5-hydroxy-3-hydroxymethylene-2,2-dimethyl-7-7-[1-methyl-4-(4-pyridyl)butyl]-4-chromanone, a viscous oil:

$R_f$ = 0.15 (silica gel, 1-benzene:1-ethyl acetate)

dl2,2-Dimethyl-5-hydroxy-7-[1-methyl-2-(2-phenylethoxy)ethyl]-4-chromanone is converted to dl-2,2-dimethyl-3-hydroxymethylene-5-hydroxy-7-[1-methyl-2-(2-phenylethoxy)ethyl]-4-chromanone (an oil).

$R_f$ = 0.35 (slica gel, 1:1 pentane:ether).

EXAMPLE 3 dl-6a,7-Dihydro-1-hydroxy-6,6-dimethyl-3-(1-methyl-4-phenylbutyl)-6H-dibenzo-[b,d]pyran-9(8H)-one To a solution of 5-hydroxy-3-hydroxymethylene-2,2-dimethyl-7-(1-methyl-4-phenylbutyl)-4-chromanone (0.916 g.) in methanol (4 ml.) and methyl vinyl ketone (0.037 ml.) is added triethylamine (0.09 ml.). The reaction is stirred for 16 hours at room temperature and then diluted with ether (50 ml.). The resulting ether solution is extracted with 10% sodium carbonate solution (4 × 5 ml.), dried over sodium sulfate and concentrated under vacuum to yield 1.09 g. of an oil. The residue is refluxed with ethanol (7.3 ml.) and 2N potassium hydroxide (7.3 ml.) for 16 hours. Thereafter, the reaction solution is cooled, acidified with 6N hydrochloric acid and extracted with dichloromethane (3 × 20 ml.). The organic phase is dried over sodium sulfate and evaporated to yield 0.99 g. of an oil which crystallizes from ether:hexane (1:1) to yield 0.49 g. of dl-6a,7-dihydro-1-hydroxy-6,6-dimethyl-3-(1-methyl-4-phenylbutyl)-6H-dibenzo[b,d]pyran-9(8H)-one, m.p. 145°-148° C. after crystallization from isopropyl ether.

NMR: $\delta_{CDCl_3}^{TMS}$ 1-2.35 (M,10,α-methylene, ethylene, remaining protons), 1.55 (S,6,gem dimethyl), 2.35-3.0 (M,5,α-methylene, benzylic-methylene, methinyl), 6.1-6.7 (M,2,aromatic), 7-7.35 (M,5-aromatic), 7.9-8.2 (bd.S,1,olefinic proton), 10.8 (S,1,phenolic OH).

IR: ($CHCl_3$) C=O 1600 $cm^{-1}$

Analysis: Calc'd for $C_{26}H_{30}O_3$: C, 79.97; H, 7.74%. Found: C, 79.91; H, 7.78%.

MS: (mol.ion) 390

Similarly, dl-6a,7-dihydro-1-hydroxy-6,6-dimethyl-3-(1-methyl-5-phenylpentyl)-6H-dibenzo[b,d]pyran-9(8H)-one is prepared from 5-hydroxy-3-hydroxymethylene-2,2-dimethyl-7-(1-methyl-5-phenylpentyl)-4-chromanone, m.p. 204°-208° C.

NMR: $\delta_{CECl_e}^{TMS}$ 1.1, 1.5 (2S,6,gem dimethyl), 1.0-3.0 [M,17,α-methyl, $\Phi CH_2(CH_2)_3$—$CH(CH_3)$—Ar, benzylic, remaining protons], 6.2, 6.5 (2D,2,aromatic protons, J = 2 cps), 7.0-7.4 (M,5,aromatic), 8.05 (D.1.vinylic, J = 2 cps), 10.8 (S,1,phenolic hydroxyl).

IR: (KBr) C=O 1613 $cm^{-1}$

Analysis: Calc'd for $C_{27}H_{32}O_3$: C, 80.16; H, 7.97%. Found: C, 80.00; H, 8.29%.

dl-6a,7-Dihydro-1-hydroxy-6,6-dimethyl-3-(2-pheylethyl)-6H-dibenzo[b,d]pyran-9(8H)-one is prepared from 5-hydroxy-3-hydroxymethylene-2,2-dimethyl-7-(2-phenylethyl)-4-chromanone, m.p. 233°-235° C.

NMR: $\delta_{CDCl_3}^{TMS}$ 1.0-1.4 (M,3,6a-methinyl, 7-methylene), 1.5 (S,6,gem dimethyl), 2.35-2.85 (M,2,8-α-methylene), 2.9 (S,4,ethylene), 6.3, 6.55 (2d,2,aromatic), 7.3 (S,5,aromatic), 7.95 (d,1,10-olefinic proton), 10.5 (S,1,hydroxyl-$D_2O$ overlay).

MS: (mol.ion) 348 and dl-6a,7-dihydro-1-hydroxy-6,6-dimethyl-3-(1-methyl-3-phenylpropyl)-6H-dibenzo[b,d]pyran-9(8H)-one from 5-hydroxy-3-hydroxymethylene-2,2-dimethyl-7-(1-methyl-3-phenylpropyl)-4-chromanone, m.p. 181° C.

NMR: $\delta_{CDCl_3}^{TMS}$ 1.2, 1.3 (d,2,methyl), 1.55(S,6,gem dimethyl), 1.6-3.1 (M,8,remaining protons), 6.3, 6.55 (2d,2,aromatic), 7.2, 7.25 (2S,6, aromatic, hydroxyl-$D_2O$ overlay, 8.05 (d,1,olefinic proton).

MS: (mol.ion) 376 dl-6aα-7-dihydro-1-hydroxy-6α-methyl-3-(1-methyl-4-phenylbutyl)-6H-dibenzo[b,d]pyran-9(8H)-one is prepared from dl-5-hydroxy-3-hydroxymethylene-2-methyl-7-(1-methyl-4-phenylbutyl)-4-chromanone; m.p. 195°-197° C.

NMR: $\delta_{CDCl_3}^{TMS}$ 1.2 (D,3,α-methyl, J = 7 Hz), 1.4 (D,3,6-methyl, J = 7 Hz), 1.3-1.8 (M,6,7-methylene, allylic), 3.8 (M,1,methinyl ether, $J_{vicinal}$ = 11 Hz), 7.0-7.4 (M,5,aromatic), 7.9 (D,1,vinylic, J = 1 Hz), 9.6 (S,1,phenolic OH).

IR: (KBr) C = O 1639 $cm^{-1}$

Analysis: Calc'd for $C_{25}H_{28}O_3$: C, 79.75; H, 7.50%. Found, C, 79.76; H, 8.33%.

U.V.: $\lambda_{max}^{C_2H_5OH}$ = 226 (ε = 14,400), 324 (□ = 26,600)

MS: (mol.ion) 376 dl-6a,7-dihydro-1-hydroxy-6,6-dimethyl-3-(1-methyl-4-phenoxybutyl)-6H-dibenzo[b,d]pyran-9(8H)-one is prepared from the corresponding 3-hydroxymethylene derivative; m.p. 165°-175° C.

MS: (mol.ion) 406

$R_f$ = 0.31 (silica gel, 18-benzene:3-ethyl acetate)

Analysis: Calc'd for $C_{26}H_{30}O_4$: C, 76.82; H, 7.44%. Found: C, 76.80; H, 7.57%.

dl-6a,7-dihydro-1-hydroxy-6,6-dimethyl-3-[1-methyl-4-(4-pyridyl)butyl]-6H-dibenzo[b,d]pyran-9(8H)-one is prepared from the corresponding 3-hydroxymethylene derivative as a glassy solid.

MS: (mol.ion) 391

Analysis: Calc'd for $C_{25}H_{29}NO_3.H_2O$: C, 73.32; H, 7.62; N, 3.42%. Found: C, 73.22; H, 7.47; N, 3.25%.

dl-6a,7-Dihydro-1-hydroxy-6,6-dimethyl-3-[1-methyl-2-(2-phenylethoxy)ethyl]-6H-dibenzo-[b,d]pyran-9(8H)-one is prepared from dl-2,2-dimethyl-3-hydroxymethylene-5-hydroxy-7-[1-methyl-2-(2-phenylethoxy)ethyl]-4-chromanone, m.p. 185°-187° C.

IR: ($CHCl_3$) C = O 1613 $cm^{-1}$.

NMR: $\delta_{CDCl_3}^{TMS}$ 1.15 (s, one methyl of gem dimethyl), 1.20 (d, J=7Hz, methyl), 1.48 (s, one methyl of gem dimethyl), 2.0-3.1 (m), 2.85 (t, J=7Hz, $CH_2Ph$), 3.4-3.8 (m, —$CH_2OCH_2$—), 6.35 (bs, ArH), 6.63 (bs, ArH), 7.30 (s, Ph), 8.10 (d, J=2Hz, C-10 H) and 12.3 (s, phenol).

MS: m/e 406 (M ⊕), 391, 376, 363, 315, 302 (100%), 287, 285 and 272.

EXAMPLE 4 dl-6aβ,7,10,10aα-Tetrahydro-1-hydroxy-6,6-dimethyl-3-(1-methyl-4-phenylbutyl)-6H-dibenzo[b,d]pyran-9(8H)-one A solution of dl-6a,7-dihydro-1-hydroxy-6,6-dimethyl-3-(1-methyl-4-phenylbutyl)-6H-dibenzo[b,d]pyran-9(8H)-one (0.976 g.) in tetrahydrofuran (7 ml.) is added to a rapidly stirred solution of lithium (0.1 g.) in liquid ammonia (35 ml.) (distilled through potassium hydroxide pellets). The reaction is stirred for 15 minutes and then solid ammonia chloride is added to discharge the blue color. The excess ammonia is allowed to evaporate and the residue is diluted with water (35 ml.) and acidified with concentrated hydrochloric acid. The water solution is extracted with dichloromethane (3 × 25 ml.) and the dichloromethane extracts dried over sodium sulfate and evaporated to yield 0.98 g. of a mixture of trans- and cis-6a,10a-diastereomers as a crude oil which is purified via column chromatography on silica gel to yield the trans-diastereomer followed in later fractions by the cis-diastereomer. The following are thus obtained:

dl-6aβ,7,10,10aα-tetrahydro-1-hydroxy-6,6-dimethyl-3-(1-methyl-4-phenylbutyl)-6H-dibenzo[b,d]pyran-9(8H)-one, 0.393 g., m.p. 200°-205° C.

NMR:$\delta_{CDCl_3}^{TMS}$ 1-2.35 (M,11,α-methyl, ethylene, remaining protons), 1.55 (S,6,gem dimethyl), 2.35-3.0(M,7,α-methylenes, benzylic-methylene, methinyl), 6.2-6.45 (M,2,aromatic), 7-7.35 (M,5,aromatic), 7.8 (bd.S,1,hydroxyl-$D_2O$ overlay).

IR: ($CHCl_3$) C=O 1600 $cm^{-1}$.

and dl-6aβ,7,10,10aβ-tetrahydro-1-hydroxy-6,6-dimethyl-3-(1-methyl-4-phenylbutyl)-6H-dibenzo[b,d]-pyran-9(8H)-one as a solid foam.

IR: ($CHCl_3$) C=O 1690 $cm^{-1}$, OH 3275 $cm^{-1}$.

NMR: $\delta_{CDCl_3}^{TMS}$ 0.95-2.12 (M,11,α-methyl, ethylene, remaining protons), 1.35, 1.4 (2S,6,gem dimethyl), 2.25-2.95 (M,7,α-methylenes, benzylic-methylene, methinyl), 6.1-6.35 (M,2,aromatic), 7.1(bd.S.,1,hydroxyl), 7.25 (S,5,aromatic).

Repetition of the above procedure but using the products of Example 3 as reactants affords: dl-6aβ,, 7,10,10aα-tetrahydro-1-hydroxy-6,6-dimethyl-3-(1-methyl-5-phenylpentyl)-6H-dibenzo[b,d]pyran-9(8H)-one, m.p. 159°-163° C.:

NMR: $\delta_{CDCl3}^{TMS}$ 1.1, 1.5 (2S,6,gem dimethyl), 0.9-3.1 [M,19,α-methyl) Φ—$CH_2$—$(CH_2)_3$—$CH(CH_3)$—Ar, benzylics, remaining protons], 3.9-4.4 (bd.D,1,α-carbonyl), 6.2 (M,2,aromatic), 7.0-7.4 (M,5,aromatic), 7.8 (S,1,phenolic hydroxyl).

IR: (KBr) C=O 1695 $cm^{-1}$.

Analysis: Calc'd for $C_{27}H_{34}O_3$: C, 79.76; H, 8.43 %.

Found: C, 79.49; H, 8.43 %.

and the corresponding cis-diastereomerdl-6aα, 7,10,10aβ-tetrahydro-1-hydroxy-6,6-dimethyl-3-(1-methyl-5-phenylpentyl)-6H-dibenzo[b,d]pyran-9(8H)-one; m.p. 91°-130° C.

IR: (KBr) C=O 1709 $cm^{-1}$.

MS: Imol. ion) 406.

dl-6aβ, 7,10,10aα-tetrahydro-l-hydroxy-6,6-dimethyl-3-(2-phenylethyl)-6H-dibenzo[b,d]pyran-9-(8H)-one, m.p. 206°-209° C.:

IR: (KBr) OH 3260 $cm^{-1}$.

NMR: $\delta_{CDCl3}^{TMS}$ 1.05-1.45 (2S,6,gem dimethyl), 2.75 (bs,4,4-ethylene), 1.1-3.1 (M,7,remaining protons), 3.75, 4.0 (2d,1,10aαproton), 6.2 (d,2,aromatic), 7.15 (S,5,aromatic), 8.8 (S,1,hydroxyl-$D_2O$ overlay).

MS (mol.ion) 350. de-6aβ, 7.10,10aα-tetrahydro-1-hydroxy-6,6-dimethyl-3-(1-methyl-3-phenylpropyl)-6H-dibenzo[b,d]pyran-9(8H)-one, m.p. 165° C.:

IR (KBr) OH 3175 $cm^{-1}$, C=O 1695 $cm^{-1}$.

and dl-6aβ,7,10,10aβ-tetrahydro-1-hydroxy-6,6-dimethyl-3-(1-methyl-3-phenylpropyl)-6H-dibenzo[b,d](8H)-oen as a solid foam:

IR ($CHCl_3$) C=O 1685 $cm^{-1}$, $Oh^-$ 3250 $cm^{-1}$.

NMR: $\delta_{CDCl3}^{TMS}$ 1.35, 1.45 (2S,6,gem dimethyl), 2.8 (bd,s,4,ethylene), 1/75-3.6 (M,8,remaining protons), 6.3 (M,2,aromatic), 7.25 (M,6,aromatic, hydroxyl).

dl-6β,7,10,10aα-tetrahydro-1-hydroxy-6,6-dimethyl-3-(1-methyl-4-phenoxybutyl)6H-dibenzo[b,d]pyran-9(8H)-one;

M.P. 160°-175° C.

MS: (mol.ion) 408

$R_f$ =0.53 (silica gel, 8-benzene:2-ethyl acetate)

NMR: $\delta_{CDCl3}^{TMS}$ 7.41-6.67 (multiplet,6,phenolic OH, $C_6H_5$); 6.3 (S,2, aromatic $H_2$ +$H_4$); 4.33-1.50 (Ms, 15, remaining methylene and methine protons); 1.47 (S,3,$CH_3$); 1.27 and 1.17 (D,3Me); 1.12 (S,3,$CH_3$).

Ananlysis: Calc'd for $C_{26}H_{32}O_4$: C, 76.44; H, 7.89 %.

Found: C, 76.61; H, 7.90 %.

dl-6aβ,7,10,10aα-tetrahydro-1-hydroxy-6,6-dimethyl-3-[1-methyl-4-(4-pyridyl)butyl]-6H-dibenzo[b,d]pyran-9(8H)-one:

M.P. 60°-70° C.

$R_f$ +0.4 (silica gel, ethyl acetate)

MS: (mol.ion) 393

NMR: $\delta_{CDCl3}^{TMS}$ O.83-1.73 (M,15,methyl,methylene), 1.73-3.0 (M,8,1-methine, remaining proteons), 3.97-4.2 (bd.D,1,aliphatic), 6.27 (S,2,aromatic), 7.03, 7.13 (D,2,pyridine aromatic), 7.55 (S,1,hydroxyl), 8.42 (M,2,pyridine aromatic).

dl-6a, 7,10,10aα-tetrahydro-1-hydroxy-6α-methyl-3 (1-methyl-4-phenylbutyl)-6H-dibenzo[b,d]pyran-9(8H)-one, m.p. 163°-167° C. (pre-softening at 140° C.)

IR: (KBr) C=O 1709 $cm^{-1}$.

Analysis: Calc'd for $C_{25}H_{30}O_3$: C, 79.33; H, 7.99 %.

Found: C, 79.43; H, 8.03 %.

MS: (mol.ion) 378.

dl-6aβ, 7,10,10aα-tetrahydro-1-hydroxy-6,6-dimethyl-3-[1methyl-2-(2-phenylethoxy)ethyl]-6H-dibenzo[b,d,]pyran-9-(8H)-one (a solid glass:

NMR: $\delta_{CDCl3}^{TMS}$ 1.13 (s,one methyl of gem dimethyl), 1.24 (d,J=7Hz,methyl), 1.50 (s,one methyl of gem dimethyl), 1.6-3.2 (M), 3.2-3.8 (M),4.05 (M,one proton), 4.30 (M,one proton), 6.33 (s, two ArH), (s,Ph) and 7.70 (s,phenol).

MS: (mol.ion) 408 (M⊕, 100%), 392, 375, 304, 287, 286, 274 and 273.

$R_f$ =0.57 (silica gel, ether)

and the corresponding cis-isomer:

dl-6β,7,10,10aβ-tetrahydro-1-hydroxy-6,6-dimethyl-3-[1-methyl-2-2-phenylethoxy)ethyl[6H-dibenzo[b,d]-pyran-9(8H)-one, m.p. 127°-130° C.:

NMR: $\delta_{CDCl3}^{TMS}$ 1.20 (d,J=7Hz,methyl), 1.32 and 1.39 (s,gem dimethyl), 1.6-3.8 (M), 6.25 (s, two ArH), 7.07 (s, phenol) and 7.28 (s,Ph).

MS: (mol.ion) 408 (M⊕, 100%), 393, 391, 325, 316, 304, 287, 286, 274, 273 and 245.

$R_f$ =0.50 (silica gel, ether).

EXAMPLE 5 dl-6aβ, 7,8,9,10,10aα-Hexahydro-1-hydroxy-6,6-dimethyl-3-(1-methyl-4-phenylbutyl)-6-H-dibenzo[b,d]pyran-9β-ol To a solution of dl-62β,7,10,10aα-9(8H)-one (0.25 g.) in ethanol (200 ml.)stirred at room temperature under nitrogen is added sodium borohydride (0.5 g). The reaction is stirred for 30 minutes and acidified with 6N hydrochloric acid, then diluted with water (50 ml.) and extracted with ether 3 × 50 ml.).The combined ether extracts are dried over sodium sulfate and concentrated under vacuum to yield 0.25 g. of a mixture of 9-OH α- and β-isomers. Column chromatography (silica gel) yields 0.087 g. of dl-6aβ, 7,8,9,10,10aα-hexahydro-1hydroxy-6,6-dimethyl-3-(1-methyl-b 4-phenylbutyl)-6H-dibenzo[b,d]pyran-9β-ol, m.p. 156°-158° C. after crystallization from ether:hexane (1:2).

MS: (mol.ion) 394

Analysis: Calc'd for $C_{26}H_{34}O_3$: C, 79.15; H, 8.69 %.

Found: C, 78.94; H, 8.79 %.

The following compounds are prepared by means of the above procedure from appropriate reactants of Example 4:

dl-6aβ,7,8,9,10,10aα-hexahydro-1-hydroxy-6,6-dimethyl-3-(1-methyl-5-phenylpentyl)-6-H-dibenzo[b,d]pyran-9β-ol:

NMR: $\delta_{CDCl3}^{TMS}$ 1.0, 1.4 (2S, gem dimethyl), 1.2 (D,3,α-methyl, J=7cps), 0.8-4.0 (M,18, remaining protons), 4.1-4.7 (M,2,phenolic-OH and alcoholic OH), 6.1, 6.2 (2D,aromatic, J=3cps), 7.0-7.3 (M,5,aromatic).

Analysis: Calc'd for $C_{27}H_{36}O_3$: C, 79.37; H, 8.88 %.

Found: C, 79.58; H, 8.92 %.

dl-6α,7,8,9,10,10a -hexahydro-1-6,6-dimethyl-3-(2-phenylethyl)-6H-dibenzo[b,d]pyran-9 -ol; m.p. 213°-215° C.:

IR: (KBr) OH 3367 $cm^{-1}$, 3125 $cm^1$

NMR: $\delta CDCl_3^{TMS}$ 1.0, 1.35 (2S,6,gem dimethyl), 2.85 (S,4,ethylene), 3/85 (bs,1-hydroxyl-$D_2O$ overlay), 3.6 (M,1,10aαproton), 0.8-3.6 (M,8,remaining protons), 6.2 (2d, 2,aromatic), 7.2 (S,5,aromatic), 8.75 (S,1,hydroxyl-$D_2O$ overlay).

MS: (mol.ion) 352 dl-6aβ,7,8,9,10,10aβ-hexahydro-1-1-hydroxy-6,6-dimethyl-3-(1-methyl-3 -phenylpropyl)6H-dibenzo[b,d]pyran-9β-ol, m.p. 171°-172° C.:

NMR: $\delta_{CHCl3}^{TMS}$ 1.15, 1.25 (d,3,methyl), 1.35 (S,6, gem dimethyl), 1.0–3.8 (M,10, remaining protons and hydroxyl), 6.1, 6.25 (2d, 2,aromatic), 7.2 (S,5,aromatic).

Analysis: Calc'd for $C_{25}H_{32}O_3$: C, 78.91; H, 8.47 %. Found: C, 78.57; H, 8.50 %.

dl-6aα-7,8,9,10,10a-hexahydro-1-6α-methyl-3-(1-methyl-4-phenylbutyl)-6H-dibenzo[b,d]pyran-9β-ol.

This product is obtained as a mixture of the diastereomeric alcohols. The mixture, a foam, is separated into two components by preparative layer chromatography on silica gel plates using 5% methanol in chloroform as eluting solvent.

The diastereomeric mixture exhibits maxima in the infrared region (in chloroform) at 3827 and 3333 $cm^{-1}$ (OH).

From 60 mg. of the foam, 10 mg. of component A is isolated; $R_f$=0.65. Its NMR spectrum is provided below.

NMR: $\delta_{CHCl3}^{TMS}$ 7.0–7.5 (M,5,aromatic), 6.2, 6.3 (2D,2,aromatic), 1.2 (D,3,α-methyl, J = 7 Hz), 0.8–4.5 (M,22,remaining protons).

Component B, 42 mg., $R_f$=0.75, is similarly isolated. Its NMR spectrum is provided below.

NMR: $\delta CDCl_3^{TMS}$ 7.0–7.5 (M,5,aromatic), 6.1, 6.3 (2D,2,aromatic), 1.2 (D,3,α-methyl, J = 7 Hz), 0.8–4.5 (M,22,remaining protons).

dl-6aβ, 7,8,9,10,10aα-hexahydro-1-hydroxy-6,6-dimethyl-3(1-methyl-4-phenoxybutyl)6-H-dibenzo[b,d]-pyran-9β-ol, m.p. 144°–146° C.

$R_f$= 0.31 (silica gel, 9-ether:1-hexane)

Analysis: Calc'd for $C_{26}H_{34}O_4$: C, 76.06; H, 8.35 %. Found: C, 75.85; H, 8.22 %.

NMR: $\delta_{CHCl_3}^{TMS}$ 6.75 (M,6,phenolic OH + $C_6H_5$); 7.95 and 7.80 (BS,2, aromatic $H_2$ + $H_4$); 4.17–1.00 (M,26,non-aromatics including 1.42 [S,Me], 128 and 1.17 [D,Me], 1.10 [S,$CH_3$ ], methylene, methine and hydroxyl).

dl-6aβ, 7,8,9,10,10aα-hexahydro-1-6,6-dimethyl-3-methyl-4-phenoxybutyl)-6H-dibenzo[b,d]pyran-9α-ol, an oil.

$R_f$= 0.37 (silica gel, 9-ether:1-hexane)

MS: (mol.ion) 410 dl-6aβ, 7,8,9,10,10aα-hexahydro-1-hydroxy-6,6-dimethyl-3[1-methyl-4-(4-pyridyl)butyl]-6H-dibenzo[b,d]pyran-962 -ol:

M.P. 170°–190° C.

$R_f$= 0.19 (silica gel, 9-benzene:1-methanol)

NMR: $\delta_{CDCl_3}^{TMS}$ 8.50–8.45 (D,2,pyridine aromatic); 7.32 (S,1,phenolic hydroxyl); 7.12–7.07 (D,2,pyridine aromatic); 6.26 (Bs,1,benzene aromatic); 6.10 (BS,1,benzene aromatic); 4.60–3.30 (M,3,methine + OH [singlet 3.83]); 2.80–0.80 (M,26,alkyl, including singlet at 1.44 [Me], doublet 1.24–1.17 [$CH_3$], singlet 1.2 [$CH_3$]and remaining menthylene and methine absorptions).

dl-6aβ,7,10,10aα-tetrahydro-1-hydroxy-6,6-dimethyl-3-[1-methyl-2-phenylethoxy)ethyl]-6H-dibenzo[b,d]-pyran-9(8H)-one is converted to dl-6aβ,7,8,9,10,10aα-hexahydro-1-hydroxy-6,6-dimethyl-3-[1-methyl-2-(2-phenylethoxy)ethyl)-6H-dibenzo[b,d]pyran-9β-ol (a solid):

IR: ($CHCl_3$) OH 3597 and 3333 $cm^{-1}$.

NMR: $\delta CDCl_3^{TMS}$ 1.02 (s, one methyl of gem dimethyl), 1.20 (d,J=7Hz, methyl), 1.37 (s, one methyl of gem dimethyl), 1.6–4.2 (M), 6.19 (bs, ArH), 6.30 (bs, ArH) and 7.27 (s.Ph).

dl-6aβ,7,10,10aβ-tetrahydro-1-hydroxy-6,6-dimethyl-3-[1-methyl-2-(2-phenylethoxy)ethyl]-6H-dibenzo[b,d]pyran-9-(8H)-one is converted to dl-6aβ,7,8,9,10,10aβ-hexahydro-1-hydroxy-6,6-dimethyl-3-[1-methyl-2-(2-phenylethoxy)ethyl]-6H-dibenzo[b,d]pyran-9β-ol, m.p. 90°–105° C.

IR: ($CHCl_3$) OH 3534 and 3279 $cm^{-1}$.

NMR: $\delta_{CDCl_3}^{TMS}$ 1.12 (M,three methyls), 1.73 (M), 2.32 (M), 2.82 (t,J=7Hz, $CH_2Ph$), 3.0–4.1 (M), 6.13 (d,J=2Hz,ArH), 6.30 (d,J=2Hz,ArH), 6.90 (bs,phenol) and 7.25 (s,Ph).

MS: (mol.ion) 410 (M⊕) and 105.

EXAMPLE 6 dl-5-Hydroxy-2,2-dimethyl-7-(2-Heptyloxy)-4-chromanone

To a solution of 5,7-dihydroxy-2,2-dimethyl-4-chromanone (18.5 g., 87.1 mM) and potassium hhydroxide (2.44 g., 43.5 mM) in N,N-dimethylformamide (58 ml.) is added with stirring 2-bromoheptane (15.77 g., 88.0 mM). The mixture is heated for four days at 100° C., cooled to room temperature and then added to a mixture of aqueous sodium hydroxide (110 ml. of 1N), water (45 ml.) and chloroform (150 ml.). The mixture is agitated and the chloroform layer separated. The aqueous layer is extracted with more chloroform (150 ml.). The combined chloroform layers are washed with 1N sodium hydroxide (2 × 100 ml.) dried over sodium sulfate and concentrated to an oil. The unreacted 2-bromoheptane is removed by distillation and the residue purified by silica gel chromatography to give 5.90 g. (22.1%) of the title product as an oil.

NMR ($CDCl_3$) δ - 12.4 (one proton singlet, hydroxylic), 5.7 and 6.0 (two one proton doublets, J = 3 Hz., aromatic protons), 4.1–4.7 (one proton multiplet, ether methine), 2.7 (2 proton singlet, C-3 methylene), 0.7–2.0 (22 proton multiplet for the remaining protons, gem dimethyl appearing as a singlet at 1.5.).

In like manner, dl-5-hydroxy-2,2-dimethyl-7-[2-(5-phenyl)pentyloxy]-4-chromanone is prepared by substituting 2-bromo-5-phenylpentane for 2-bromoheptane; m.p. 83°–84° C.

IR (KBr) C = O 1639 $cm^{-1}$

NMR: $\delta_{CDCl_3}^{TMS}$ 1.3 (D,3,α-methyl, J = 7 Hz), 1.3–2.0 (M,4, ethylene), 1.5 (S,6,gem dimethyl), 2.7 (S,2,α-methylene), 2.5–2.9 (M,2, benzylic methylene), 4.1–4.7 (M,1,methine), 5.9–6.1 (M,2,aromatic), 7.1–7.5 (M,5,aromatic), 12.2 (S,1,phenolic).

MS: (mol.ion) 354

Analysis: Calc'd for $C_{22}H_{26}O_4$: C, 74.55; H, 7.39%. Found: C, 74.68; H, 7.46% dl-5-hydroxy-2,2-dimethyl-7-(1-methyl-3-phenylpropoxy)-4-chromanone is prepared from 2-bromo-4-phenylbutane as an oil:

NMR: $\delta_{CDCl_3}^{TMS}$ 1.25, 1.35 (d,3,methyl), 1.4 (S,6,gem dimethyl), 1.6–2.4 (M,2,methylene), 2.6 (S,2,benzylic methylene), 2.85 (S,2,3 α-methylene), 4.05–4.7 (M,1,methinyl), 5.9 (6d,2,aromatic), 7.25 (S,5,aromatic).

dl-5-hydroxy-2,2-dimethyl-7-cyclohexyloxy-4-chromanone is prepared from bromocyclohexane:

M.P. 72°–75° C.

IR (KBr) C=O 1626$cm^{-1}$; OH 3390 $cm^{31 1}$

MS: (mol.ion)290

NMR: $\delta_{CDCl_3}^{TMS}$ 1–2.1 (M,10,$C_5H_{10}$-cyclohexyl), 1.4 (S,6,gem dimethyl), 2.65 (S,2,α-methylene), 4.0–4.45 (M,1,cyclohexyl methinyl), 5.85–6.05 (M,2,aromatic), 11.9 (S, hydroxyl, $D_2O$ overlay).

EXAMPLE 7 dl-5-Hydroxy-3-Hydroxymethylene-2,2-Dimethyl-7-(2-Heptyloxy)-4-Chromanone

To the sodium hydride obtained by washing 9.23 g. (192 mM) of 50% sodium hydride in mineral oil dispersion with pentane is added dropwise, over a 30 minute period, a solution of dl-5-hydroxy-2,2-dimethyl-7-(2-heptyloxy)-4-chromanone (5.90 g., 19.2 mM) and ethyl formate (34.9 ml., 432 mM). After the addition is complete, ether (475 ml.) is added and the resulting mixture refluxed. After 18 hours, the reaction mixture is cooled to room temperature and acidified with 1N hydrochloric acid. The organic layer is separated and the aqueous layer is further extracted with ether (3 × 125 ml.). The combined ether extracts are dried over sodium sulfate and concentrated under vacuum to yield 6.41 g. (>100%) of dl-5-hydroxy-3-hydroxymethylene-2,2-dimethyl-7-(2-heptyloxy)-4-chromanone as an oil.

NMR $\delta_{CDCl_3}^{TMS}$ 13.4 (one broad singlet proton, hydroxylic), 11.8 (one proton singlet, phenolic hydroxylic, 7.4 (one broad proton singlet, vinyl), 6.1 6.0 (2 one proton doublets, J = 3Hz, aromatic), 4.8–4.2 (one proton multiplet, methine), 2.1–0.7 (20 proton multiplet for the remaining protons).

In like manner, appropriate reactants of Example 6 are converted to: dl-5-hydroxy-3-methylene-2,2-dimethyl-7-[2-(5-phenyl)pentyloxy]-4-chromanone, an oil.

NMR: $\delta_{CDCl_3}^{TMS}$ 1.3 (D,3,α-methyl, J = 7 Hz), 1.3–2.0 (M,4, ethylene), 1.4 (S,6,gem dimethyl), 2.3–2.8 (bd., T,2-benzylic methylene), 4.1–4.7 (M,1,methine), 5.8–6.0 (M,2,aromatic), 7.0–7.4 (M,6,aromatic and vinylic), 10.0 (S,1,phenolic), 13.3 (bd,S,1,hydroxylic);

dl-5-hydroxy-3-hydroxymethylene-2,2-dimethyl-7-[2-(4-phenyl)butyloxy]-4-chromanone, an oil;

dl-5-hydroxy-3-hydroxymethylene-2,2-dimethyl-7-cyclohexyloxy-4-chromanone;

IR (Kbr) C=O 1620 $cm^{-1}$; OH 3420 $cm^{-1}$

MS: (mol.ion) 318

NMR: $\delta_{CDCl_3}^{TMS}$ 1.1–2.3 (M,10,$C_5H_{10}$-cyclohexyl), 1.55 (S,6,gem dimethyl), 4.1–4.5 (M,1-cyclohexylmethinyl), 3.9–6.1 (M,2,aromatic), 7.1–7.5(d,l,methinyl), 11.6 (S,1,hydroxyl, $D_2O$ overlay).

dl-5-hydroxy-3-hydroxymethylene-2,2-dimethyl-7-(1-methyl-3-phenoxypropyl)-4-chromanone, an oil (from reactant of Example 1):

$R_f$ = 0.42 (silica gel, 18-benzene:1-ethyl acetate)

MS: (mol.ion) 368

EXAMPLE 8 dl-6a,7-Dihydro-1-Hydroxy-6,6-Dimethyl-3-(2-Heptyloxy)-6H-Dibenzo-[b,d]pyran-9(8H)-One To a solution of dl-5-hydroxy-3-hydroxymethylene-2,2-dimethyl-7-(2-heptyloxy)-4-chromanone (5.17 g., 15.4 mM) and methylvinyl ketone (2.27 ml., 27.9 mM) in methanol (23 ml.) is added triethylamine (0.54 ml.). The reaction is stirred for 16 hours at room temperature and then diluted with ether (250 ml.). The resulting ether solution is extracted with 10% sodium carbonate (6 × 30 ml.), dried over sodium sulfate, and concentrated under vacuum to yield 6.11 g. of an oil. The residue is refluxed with ethanol (45 ml.) and 2N potassium hydroxide (45 ml.) for 16 hours. Thereafter, the reaction solution is cooled, acidified with 6N hydrochloric acid and extracted with dichloromethane (3 × 100 ml.). The organic phase is dried over sodium sulfate and evaporated to yield 6.3 g. of a dark solid. The solid is triturated in hot ether to yield 1.00 g. of the title compound, m.p. 185°–189° C.; 1.26 g. of further material is obtained via silica gel chromatography of the mother liquor. The total yield is 42.3%.

NMR ($CDCl_3$) δ 11.2 (one broad proton singlet, phenolic OH), 7.9 (one broad proton singlet, vinyl), 6.2, 5.9 (two one proton doublets, J ≅ 3Hz, aromatic protons), 4.6–4.0 (one proton multiplet, methine ether), 3.0–0.6 (25 proton multiplet, remaining protons).

IR (KBr) C = O 1600 $cm^{-1}$.

Analysis: Calc'd for $C_{22}H_{30}O_4$: C, 73.71; H, 8.44%. Found: C, 73.41; H, 8.37%.

UV $\lambda_{max}^{CH_3CH_2OH}$ = 342 mμ(ε = 26,800).

The following compounds are similarly prepared from appropriate reactants of Example 7:

dl-6a,7-dihydro-1-hydroxy-6,6-dimethyl-3-(1-methyl-4-phenylbutoxy)-6H-dibenzo[b,d]pyran-9(8H)-one;

m.p. 140°–168° C;

NMR: $\delta_{CDCl_3}^{TMS}$ 1.3 (D,2,α-methyl, J = 7 Hz), 1.1–2.3 (M,15,remaining protons), 2.3–3.0 (bd,T,2,benzylic-methylene), 4.1–4.7 (M,1,methine), 5.95 (D,1,aromatic, J = 2 Hz), 6.3 (D,1,aromatic, J = 2 Hz), 7.2–7.4 (M,5,aromatic), 8.0 (D,1,vinylic, J = 2 Hz).

IR: (KBr) C = O 1563 $cm^{-1}$

Analysis: Calc'd for $C_{26}H_{30}O_4O$: C, 76.82; H, 7.44%. Found: C, 76.74; H, 7.48%.

MS: (mol.ion) 406 dl-6a,7-dihydro-1-hydroxy-6,6-dimethyl-3-(1-methyl-3-phenylbutoxy)-6H-dibenzo[b,d]pyran-9(8H)-one;

M.P. 163° C.

NMR: $\delta_{CDCl_3}^{TMS}$ 1.2, 1.3 (d,3,methyl), 1.45 (S,6,gem dimethyl), 1.65–2.2 (M,2,methylene), 2.3–2.95 (M,4,methylene,benzylic methylene), 4.1–4.6 (M,1, methinyl), 5.9, 6.15 (2d,2,aromatic), 7.15 (S,6,aromatic, hydroxyl-$D_2O$ overlay), 7.95 (6S,1,olefinic proton).

MS: (mol.ion) 392 dl-6a,7-dihydro-1-hydroxy-6,6-dimethyl-3-cyclohexyloxy-6H-dibenzo[b,d]pyran-9(8H)-one;

M.P. 259°–254° C.

IR (KBr) C=O 1590 $cm^{-1}$; OH 3390 $cm^{-1}$

NMR: $\delta_{DMSO}$ 1.05–3.0 (M,15,$C_5H_{10}$-cyclohexyl, 6a-methinyl, 7-methylene, 8-α-methylene), 1.45 (S,6,gem, dimethyl), 4.0–4.4 (M,1,methinyl), 5.8–6.1 (2d,2,aromatic), 7.1–7.25 (d,l,olefinic proton), 7.3 (S,1,hydroxyl-$D_2O$ overlay).

dl-6a,7-dihydro-1-hydroxy-6,6-dimethyl-3-(1-methyl-3-phenoxypropyl)-6H-dibenzo[b,d]pyran-9(8H)-one, a light yellow solid:

M.P. 203°–206° C.

MS: (mol.ion) 392

Analysis: Calc'd for $C_{25}H_{28}O_4$: C, 76.50; H, 7.19%. Found: C, 76.33; H, 7.12%.

EXAMPLE 9 dl-6aβ,7,10,10aα-Tetrahydro-1-Hydroxy6,6-Dimethyl-3-(2-Heptyloxy)-6H-Dibenzo[b,d]pyran-9(8H)-One A solution of dl-6aβ,7-dihydro-1-hydroxy-6,6-dimethyl-3-(2-heptyloxy)-6H-dibenzo[b,d]pyran-9(8H)-one (1.2 g., 3.3 mM) in tetrahydrofuran (9 ml.) is added dropwise to a rapidly stirred solution of lithium (25 mg.) in liquid ammonia (45 ml.) at −78° C. During the addition an additional 75 mg. of lithium is added to insure the blue color. After an additional 15 minutes of stirring solid ammonium chloride is added to discharge the blue color. The excess ammonia is allowed to evaporate and the residue was diluted with water (45 ml.) and acidified with 10% hydrochloric acid. The aqueous solution is extracted with dichloromethane (3 × 50 ml.) and the dichloromethane extracts dried over sodium sulfate and evaporated to yield 1.30 g. of a crude semi-solid which is purified via silica gel column chromatography to yield 0.614 g. (50.9%) of product, m.p. 155°-158° C. after recrystallization from chloroform-/hexane.

NMR ($CDCl_3$) δ - 8.2 (one proton singlet, phenolic OH), 5.8-6.3 (2 proton multiplet, aromatic), 3.9-4.6 (2 proton multiplet, methine ether and C-10 equatorial), 0.3-3.2 (26 proton multiplet, remaining protons).

IR (KBr) C = O 1737 $cm^{-1}$.

MS (m/e) 360 (M+), 261 (M-99).

Analysis: Calc'd for $C_{22}H_{32}O_4$: C, 73.30; H, 8.95%. Found: C, 73.05; H, 8.82%.

and the corresponding cis-isomer:

dl-6aβ,7,10,10aβ-tetrahydro-1-hydroxy-6,6-dimethyl-3-(2-heptyloxy)-6H-dibenzo[b,d]pyran-9(8H)-one, m.p. 141°-146° C. (from ether/hexane).

IR: (KBr) C=O 1718 $cm^{-1}$.

MS (m/e) 360 ($M^+$), 261 (M-99)

Similarly, the following compounds are prepared from products of Example 8:

dl-6aβ,7,10,10aα-tetrahydro-1-hydroxy-6,6-dimethyl-3-(1-methyl-4-phenylbutoxy)-6H-dibenzo[b,d]pyran-9(8H)-one; m.p. 122°-125° C.

NMR: $\delta_{CDCl_3}^{TMS}$ 1.3 (D,3α-methyl,J=7Hz), 1.1-3.0 (M,16, remaining protons), 2.3-3.0 (bd.T,2,benzylic methylene), 4.1 (bd.D,1,C-10 equatorial,J=14Hz), 4.1-4.7 (M,1,methine), 5.95 (D,1,aromatic,J=2Hz), 6.1 (D,1,aromatic,J=2Hz), 7.2-7.4 (M,5,aromatic), 7.9 (S,1,phenolic).

IR: (KBr) C=O 1709 $cm^{-1}$

Analysis: Calc'd for $C_{26}H_{32}O_4$: C, 76.44; H, 7.90%. Found: C, 76.22; H, 7.79%.

and the corresponding cis-isomer:

dl-6aβ,7,10,10aβ-tetrahydro-1-hydroxy-6,6-dimethyl-3-(1-methyl-4-phenylbutoxy)-6H-dibenzo[b,d]pyran-9(8H)-one, m.p. 141°-142° C.

IR: (KBr) C=O 1707 $cm^{-1}$

MS: (mol.ion) 408

Analysis: Calc'd for $C_{26}H_{32}O_4$: C, 76.44; H, 7.90%. Found: C, 76.58; H, 7.92%.

dl-6aβ,7,10,10aα-tetrahydro-1-hydroxy-6,6-dimethyl-3-(1-methyl-3-phenylpropoxy)-6H-dibenzo[b,d]pyran-9(8H)-one, m.p. 160° C.

NMR: $\delta_{CDCl_3}^{TMS}$ 1.2, 1.3 (d,2, -methyl), 1,4 (S,6,gem dimethyl), 1.65-2.9 (M,11,remaining protons), 3.9-4.5 (M,2,10aα-proton, methinyl), 5.9-6.1 (2d,2, aromatic), 7.2 (S,5,aromatic), 7.9 (S,1,hydroxyl-$D_2O$ overlay)

MS: (mol.ion) 394 dl-6aβ,7,10,10aα-tetrahydro-1-hydroxy-6,6-dimethyl-3-cyclohexyloxy-6H-dibenzo[b,d]pyran-9(8H)-one, m.p. 215°-218° C.

IR (KBr) C=O 1695 $cm^{-1}$; OH 3225 $cm^{-1}$

MS: (mol.ion) 344

NMR: $\delta_{CDCl_3}^{TMS}$ 1.0-3.2 (M,18,$C_5H_{10}$ -cyclohexyl, 6aβ,7,8,10,10aβ-protons), 1.5 (S,6,gem dimethyl), 3.9-4.3 (M,1,cyclohexyl-methinyl), 5.9, 6.05 (2d,2, aromatic), 8.9 (bs,1,hydroxyl-$D_2O$ overlay).

dl-6aβ,7,10,10aα-tetrahydro-1-hydroxy-6,6-dimethyl-3-(1-methyl-3-phenoxypropyl)-6H-dibenzo[b,d]pyran-9(8H)-one:

M.P. 167°-170° C.

MS: (mol.ion) 394

Analysis: Calc'd for $C_{25}H_{30}O_4$: C, 76.11 H, 7.66%. Found: C, 75.93; H, 7.63; %.

NMR $\delta_{CDCl_3}^{TMS}$ 7.87 (S,1,phenolic proton), 7.42-6.67 (M,5, $C_6H_5$), 6.33 (S,2,aromatic $H_2$ + $H_5$), 4.42-1.00 (M,22,non-aromatics—including triplet centered at 3.90 for —$CH_2$—O—, singlet at 1.48 for $CH_3$, doublet centered at 1.27 for $CH_3$, singlet at 1.13 for $CH_3$ and 11 other methylene, methine protons).

EXAMPLE 10 dl-6aβ,7,8,9,10,10aα-Hexahydro-1-6,6-Dimethyl-3-(2-Heptyloxy)-6H-Dibenzo[b,d]pyran-9β-ol To a solution dl-β6aβ,7,10,10aα-tetrahydr-1-hydroxy-6,6-dimethyl-3-(2-heptyloxy)-6-H-dibenzo[b,d]pyran-9(8H)-one (0.60 g., 1.66 mM) in ethanol (18 ml.), stirred at room temperature under nitrogen is added sodium borohydride (275 mg.). The reaction is stirred for 30 minutes and poured onto a mixture of ice (35 ml.), 10% hydrochloric acid (35 ml.) and ether (200 ml.). The ether layer is separated and the aqueous layer extracted with additional ether (2 × 100 ml.). The combined ether extracts are dried over sodium sulfate and evaporated to an oil. Crystallization from hexane yielded 305 mg. (50.3%) of product, m.p. 102°-104° C.

NMR $\delta_{CDCl_3}^{TMS}$ - 7.9-6.7 (one broad proton singlet, hydroxylic), 6.1-5.8 (two broad proton singlet, aromatic), 4.5-0.5 (31 proton multiplet, remaining protons).

IR (KBr) OH 3390 $cm^{-1}$.

Analysis: Calc'd for $C_{22}H_{34}O_4$: C, 72.89; H, 9.45%. Found: C, 72.52; H, 9.18%.

Similarly, the following are prepared from appropriate tetrahydro compounds:

dl-6aβ,7,8,9,10,10aα-hexahydro-1-hydroxy-6,6-dimethyl-3-(1-methyl-4-phenylbutoxy)-6H-dibenzo[b,d]pyran-9β-ol, an amorphous solid.

IR: (KBr) OH 3390 $cm^{-1}$

MS: (mol.ion) 410

(NMR: $\delta_{CDCl_3}^{TMS}$ 1.3 (P,3,α-methyl), 1.0-4.5 (M,24,remaining protons), 5.8-6.0 (M,2,aromatic), 6.8-7.3 (M,5,aromatic).

dl-6aβ,7,8,9,10,10aα-hexahydro-1-hydroxy-6,6-dimethyl-3-(1-methyl-3-phenylpropyloxy)-6H-dibenzo[b,d]pyran-9β-ol, an amorphous solid.

MS: (mol.ion) 396 dl-6aβ,7,8,9,10,10aα-1-hydroxy-6,6-dimethyl-3-cyclohexyloxy-6H-dibenzo[b,d]pyran-9β-ol:

M.P. 214°-216° C.

IR (KBr) OH 3365 $cm^{-1}$; 3125 $cm^{-1}$

MS: (mol.ion) 346

NMR: $\delta_{CDCl_3}^{TMS}$ [1.0-3.0 (M,23,$C_5H_{10}$-cyclohexyl,-gem dimethyl, 7,8,9α,10 protons), 3.5-4.15 (M,2,6aβ,-10aα protons), 4.35-4.7 (M,1,cyclohexyl-methinyl), 4.85-5.05 (bd,1,hydroxyl-$D_2O$ overlay), 6.1-6.45 (M,2,aromatic), 9.7 (S,1,hydroxyl-$D_2O$ overlay).

dl-6aβ,7,8,9,10,10aα-hexahydro-1-hydroxy-6,6-dimethyl-3-(1-methyl-3-phenoxypropyl)-6H-dibenzo[b,d]pyran-9β-ol:

M.P. 151°-152° C.

$R_f$ = 0.25 (silica gel, 9-ether:1hexane)

MS: (mol.ion) 396

Analysis: Calc'd for $C_{25}H_{32}O_4$: C, 75.72; H, 8.14%. Found: C, 75.79; H, 8.39%.

dl-6aβ,7,8,9,10,10aα-hexahydro-1-hydroxy-6,6-dimethyl-3-(1-methyl-3-phenoxypropyl)-6H-dibenzo[b,d]pyran-9α-ol; an oil.

$R_f$ = 0.35 (silica gel, 9-ether:1-hexane)

MS: (mol.ion) 396

EXAMPLE 11

The following compounds are prepared according to the procedures of Examples 1-5 from appropriate (3,5-dihydroxy)phenyl compounds of the formula 3,5-

$(HO)_2C_6H_3$—Z—W and the appropriate acid of formula $R_4R_5C{=}CH{-}COOH$.

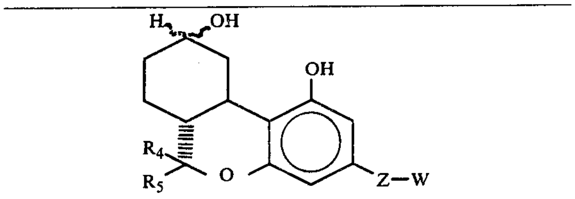

| $R_4$ | $R_5$ | Z | W |
|---|---|---|---|
| $CH_3$ | $CH_3$ | $-(CH_2)_6-$ | $C_6H_5$ |
| H | H | $-(CH_2)_7-$ | $C_6H_5$ |
| $CH_3$ | $CH_3$ | $-(CH_2)_8-$ | $C_6H_5$ |
| $CH_3$ | H | $-CH(CH_3)(CH_2)_5-$ | $C_6H_5$ |
| $C_2H_5$ | $C_2H_5$ | $-CH(CH_3)(CH_2)_6-$ | $C_6H_5$ |
| $CH_3$ | $CH_3$ | $-CH(CH_3)(CH_2)_7-$ | $C_6H_5$ |
| H | H | $-CH(CH_3)(CH_2)_3-$ | $4\text{-}FC_6H_4$ |
| $CH_3$ | $C_2H_5$ | $-C(CH_3)_2(CH_2)_3-$ | $C_6H_5$ |
| $CH_3$ | $CH_3$ | $-(CH_2)_3-CH(CH_3)-$ | $C_6H_5$ |
| $CH_3$ | H | $-CH(CH_3)(CH_2)_2CH(CH_3)-$ | $C_6H_5$ |
| $C_2H_5$ | H | $-CH(CH_3)(CH_2)_3-$ | $4\text{-}ClC_6H_4$ |
| $C_2H_5$ | $C_2H_5$ | $-CH(CH_3)(CH_2)_4-$ | $4\text{-}ClC_6H_4$ |
| $CH_3$ | $CH_3$ | $-CH(CH_3)(CH_2)_2-$ | $4\text{-}ClC_6H_4$ |
| H | H | $-CH(CH_3)(CH_2)-$ | $4\text{-}ClC_6H_4$ |
| $CH_3$ | $CH_3$ | $-CH(CH_3)(CH_2)-$ | $4\text{-}FC_6H_4$ |
| $CH_3$ | $CH_3$ | $-CH(CH_3)(CH_2)_2-$ | 4-pyridyl |
| H | H | $-(CH_2)_3$ | 2-pyridyl |
| $C_2H_5$ | H | $-(CH_2)_3$ | 3-pyridyl |
| $CH_3$ | $CH_3$ | $-(CH_2)_3$ | 4-pyridyl |
| H | $C_2H_5$ | $-(CH_2)_3$ | 2-piperidyl |
| H | H | $-(CH_2)_3$ | 4-piperidyl |
| $CH_3$ | H | $-(CH_2)_4$ | 2-pyridyl |
| $C_2H_5$ | H | $-(CH_2)_4$ | 4-pyridyl |
| $C_2H_5$ | $C_2H_5$ | $-(CH_2)_4$ | 3-piperidyl |
| $CH_3$ | $CH_3$ | $-(CH_2)_4$ | 4-piperidyl |
| H | H | $-(CH_2)_2$ | $C_6H_5$ |
| H | H | $-CH(CH_3)(CH_2)_2-$ | $4\text{-}FC_6H_4$ |
| $CH_3$ | H | $-CH(CH_3)(CH_2)_2-$ | $4\text{-}ClC_6H_4$ |
| $C_2H_5$ | $C_2H_5$ | $-CH(CH_3)(CH_2)_2-$ | $C_6H_5$ |
| H | H | $-CH(CH_3)(CH_2)_3-$ | $C_6H_5$ |
| $CH_3$ | $CH_3$ | $-CH_2CH(CH_3)CH_2-$ | 2-pyridyl |
| H | H | $-CH_2CH(CH_3)CH_2-$ | 4-piperidyl |
| $C_2H_5$ | H | $-CH(CH_3)CH(CH_3)CH_2-$ | 3-pyridyl |
| $C_2H_5$ | $C_2H_5$ | $-CH(CH_3)CH(CH_3)CH_2-$ | 4-pyridyl |
| H | H | $-CH(CH_3)CH(CH_3)CH_2-$ | 3-piperidyl |
| $CH_3$ | $C_2H_5$ | $-CH(CH_3)(CH_2)_2-$ | 2-pyridyl |
| $CH_3$ | $C_2H_5$ | $-CH(CH_3)(CH_2)_2-$ | 3-pyridyl |
| $CH_3$ | $CH_3$ | $-CH(CH_3)(CH_2)_2-$ | 4-piperidyl |
| H | H | $-CH(CH_3)(CH_2)_3-$ | 3-pyridyl |
| $CH_3$ | $CH_3$ | $-CH(CH_3)(CH_2)_3-$ | 4-piperidyl |
| $CH_3$ | $CH_3$ | $-CH(CH_3)CH(C_2H_5)CH_2-$ | 4-pyridyl |
| $C_2H_5$ | $CH_3$ | $-CH(C_2H_5)(CH_2)_2-$ | 4-pyridyl |
| $C_2H_5$ | H | $-CH(C_2H_5)(CH_2)_2-$ | 2-piperidyl |
| H | H | $-CH(C_2H_5)(CH_2)_2-$ | 4-piperidyl |
| $CH_3$ | H | $-CH_2CH(C_2H_5)CH_2-$ | 3-pyridyl |
| $CH_3$ | $CH_3$ | $-CH(C_2H_5)(CH_2)_3-$ | 3-pyridyl |
| $CH_3$ | $CH_3$ | $-CH(C_2H_5)(CH_2)_3-$ | 4-pyridyl |
| $C_2H_5$ | $C_2H_5$ | $-CH(C_2H_5)CH(CH_3)CH_2-$ | 2-pyridyl |
| H | H | $-CH(C_2H_5)CH(C_2H_5)CH_2-$ | 4-pyridyl |
| H | H | $-CH(C_2H_5)CH(C_2H_5)CH_2-$ | 2-piperidyl |
| $CH_3$ | $CH_3$ | $-(CH_2)_3CH(CH_3)-$ | $C_6H_5$ |
| $CH_3$ | $CH_3$ | $-(CH_2)_3CH(CH_3)-$ | $4\text{-}FC_6H_4$ |
| $CH_3$ | $CH_3$ | $-(CH_2)_3CH(CH_3)-$ | 4-pyridyl |
| H | H | $-(CH_2)_3CH(CH_3)-$ | $C_6H_{11}$ |
| $CH_3$ | $CH_3$ | $-(CH_2)_3CH(CH_3)-$ | $C_6H_{11}$ |
| $CH_3$ | $CH_3$ | $-CH(CH_3)(CH_2)_2CH(CH_3)-$ | $C_6H_5$ |
| $CH_3$ | H | $-CH(CH_3)(CH_2)_2CH(CH_3)-$ | $C_6H_{11}$ |
| $C_2H_5$ | $C_2H_5$ | $-CH(CH_3)(CH_2)_2CH(CH_3)-$ | 4-piperidyl |
| $CH_3$ | $CH_3$ | $-CH(CH_3)(CH_2)_3-$ | $C_6H_{11}$ |
| H | H | $-CH(CH_3)(CH_2)_2CH(CH_3)-$ | $C_6H_{11}$ |
| $C_2H_5$ | $C_2H_5$ | $-(CH_2)_3-$ | $C_6H_{11}$ |
| $CH_3$ | H | $-(CH_2)_4-$ | $C_6H_{11}$ |
| $CH_3$ | $C_2H_5$ | $-(CH_2)_8-$ | $C_6H_{11}$ |
| $CH_3$ | $CH_3$ | $-(CH_2)_2-$ | $C_4H_7$ |
| $CH_3$ | $CH_3$ | $-CH_2CH(CH_3)CH_2-$ | $C_5H_9$ |
| H | $CH_3$ | $-CH_2CH(CH_3)CH_2-$ | $C_5H_9$ |
| $CH_3$ | $CH_3$ | $-CH(CH_3)(CH_2)_2-$ | $C_7H_{13}$ |
| H | H | $-CH(CH_3)CH(CH_3)CH_2-$ | $C_6H_{11}$ |
| $CH_3$ | $CH_3$ | $-CH(CH_3)(CH_2)_3-$ | $C_5H_9$ |
| $CH_3$ | $CH_3$ | $-(CH_2)_4-$ | $C_6H_5$ |
| $CH_3$ | $CH_3$ | $-(CH_2)_2CH(C_2H_5)-$ | $C_6H_5$ |
| $CH_3$ | $CH_3$ | $-C(CH_3)_2-$ | $C_6H_5$ |
| H | $CH_3$ | $-CH(CH_3)CH_2CH(C_2H_5)-$ | $C_6H_5$ |
| H | $CH_3$ | $-CH(CH_3)CH_2-$ | $C_5H_9$ |
| H | $CH_3$ | $-CH(CH_3)CH_2-$ | $C_3H_5$ |
| $C_2H_5$ | H | $-CH(CH_3)CH(CH_3)-$ | $C_6H_{11}$ |
| $CH_3$ | $CH_3$ | $-CH(CH_3)(CH_2)_4-$ | $C_5H_9$ |

-continued

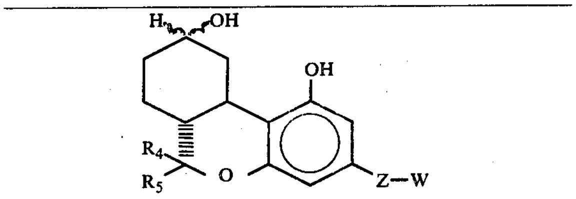

| $R_4$ | $R_5$ | Z | W |
|---|---|---|---|
| $CH_3$ | $CH_3$ | $-CH(C_2H_5)(CH_2)_2-$ | $C_6H_5$ |

EXAMPLE 12

Compounds of the following formula are obtained from appropriate reactants of Preparations K and Y and appropriate acids of formula $R_4R_5C{=}CH{-}COOH$ by the procedures of Examples 1-4 ($R_4$ and $R_5$ = H, $CH_3$ or $C_2H_5$):

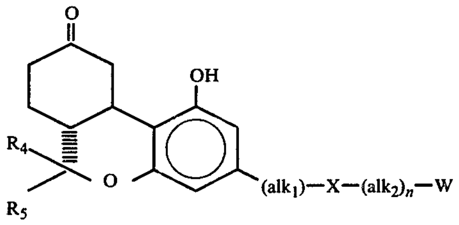

Reduction of the keto compounds with sodium borohydride according to the procedure of Example 5 affords the corresponding 9-hydroxy compounds (both isomers formed; the β-form predominates). The sulfoxide and sulfone compounds of Examples 15 and 16 are reduced in like manner to the corresponding 9-hydroxy compounds.

EXAMPLE 13 dl-5-Hydroxy-2,2-dimethy-7-(1-methyl-4-phenylbutoxy)-4-chromanone

A mixture of 5-phenyl-2-pentanol (16.4 g., 100 mM), triethylamine (28 ml., 200 mM) and dry tetrahydrofuran (80 ml.) under a nitrogen atmosphere is cooled in an ice/water bath. Methanesulfonyl chloride (8.5 ml., 110 mM) in dry tetrahydrofuran (20 ml.) is added dropwise at such a rate that the temperature holds essentially constant. The mixture is allowed to warm to room temperature and is then filtered to remove triethylamine hydrochloride. The filter cake is washed with dry tetrahydrofuran and the combined wash and filtrate evaporated under reduced pressure to give the product as an oil. The oil is dissolved in chloroform (100 ml.) and the solution washed with water (2 × 100 ml.) and then with saturated brine (1 × 20 ml.). Evaporation of the solvent affords 21.7 g. (89.7%) yield of 5-phenyl-2-pentanol mesylate which is used in the next step without further purification.

A mixture of 2,2-dimethyl-5,7-dihydroxy-4-chromanone (2.08 g., 10 mM), potassium carbonate (2.76 g., 20 mM), N,N-dimethylformamide (10 ml.) and 5-phenyl-2-pentanol mesylate (2.64 g., 11 mM), under a nitrogen atmosphere, is heated to 80°-82° C. in an oil bath for 1.75 hours. The mixture is cooled to room temperature and then poured into ice/water (100 ml.). The aqueous solution is extracted with ethyl acetate (2 × 25 ml.) and the combined extracts washed successively with water (3 × 25 ml.) and saturated brine (1 × 25 ml.). The extract is then dried ($MgSO_4$), decolorized with charcoal and evaporated to give the product as an oil which crystallizes upon seeding with pure product; m.p. 83°-84° C. Yield = quantitative.

In like manner, the following compounds are prepared from appropriate 2,2-$R_4R_5$-5,7-dihydroxy-4-chromanones and appropriate alkanols. The necessary alkanol reactants not previously described in the literature are prepared from appropriate aldehydes or ketones via the Wittig reaction of Preparation G.

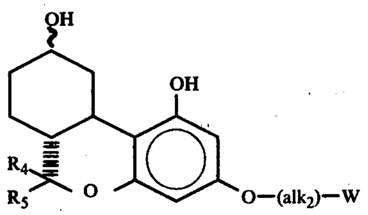

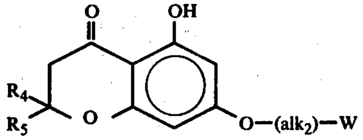

| $R_4$ | $R_5$ | $alk_2$ | W | $alk_2$ | W | $R_4$ | $R_5$ |
|---|---|---|---|---|---|---|---|
| $CH_3$ | $CH_3$ | $CH_2C(CH_3)_2(CH_2)_4$ | $CH_3$ | $(CH_2)_3$ | 3-pyridyl | $CH_3$ | $CH_3$ |
| $CH_3$ | $CH_3$ | $CH_2CH(CH_3)(CH_2)_2CH(CH_3)CH_2$ | $CH_3$ | $(CH_2)_3$ | 4-pyridyl | $CH_3$ | H |
| $CH_3$ | H | $CH(CH_3)CH_2CH(CH_3)CH_2CH(CH_3)$ | $CH_3$ | $(CH_2)_4$ | 2-pyridyl | $CH_3$ | $C_2H_5$ |
| $CH_3$ | H | $(CH_2)_2CH(CH_3)CH_2CH(CH_3)$ | $CH_3$ | $(CH_2)_3$ | 2-piperidyl | H | H |
| H | H | $CH(CH_3)(CH_2)_2C(CH_3)_2$ | $CH_3$ | $(CH_2)_3$ | 4-piperidyl | $CH_3$ | H |
| $C_2H_5$ | $C_2H_5$ | $CH_2CH(C_2H_5)$ | $C_6H_5$ | $(CH_2)_3$ | 4-$FC_6H_4$ | $CH_3$ | $CH_3$ |
| $CH_3$ | $C_2H_5$ | $CH_2CH_2CH(CH_3)$ | $C_6H_5$ | $(CH_2)_3$ | 4-$ClC_6H_4$ | H | H |
| $CH_3$ | $CH_3$ | $(CH_2)_4$ | $C_6H_5$ | $(CH_2)_4$ | $C_6H_5$ | $C_2H_5$ | H |
| H | H | $(CH_2)_4CH(C_2H_5)$ | $C_6H_5$ | $(CH_2)_4$ | 4-$FC_6H_4$ | $C_2H_5$ | H |
| H | $CH_3$ | $(CH_2)_7$ | $C_6H_5$ | $CH(CH_3)(CH_2)_2$ | 2-pyridyl | H | H |
| H | H | $CH(CH_3)(CH_2)_5$ | $C_6H_5$ | $CH(CH_3)(CH_2)_2$ | 3-pyridyl | $C_2H_5$ | $C_2H_5$ |
| $C_2H_5$ | H | $(CH_2)_9$ | $C_6H_5$ | $CH(CH_3)(CH_2)_3$ | 4-pyridyl | $CH_3$ | $CH_3$ |
| $CH_3$ | $CH_3$ | $(CH_2)_9$ | $CH_3$ | $CH(CH_3)(CH_2)_2$ | 4-piperidyl | $CH_3$ | $CH_3$ |
| H | $CH_3$ | $CH(CH_3)CH_2$ | 2-pyridyl | $CH(C_2H_5)(CH_2)_2$ | 2-pyridyl | H | $CH_3$ |
| H | $C_2H_5$ | $CH_2C(CH_3)_2$ | 2-pyridyl | $CH(C_2H_5)(CH_2)_2$ | 4-pyridyl | $CH_3$ | $CH_3$ |
| H | $CH_3$ | $(CH_2)_3$ | 2-pyridyl | $CH(C_2H_5)(CH_2)_2$ | 4-piperidyl | $C_2H_5$ | $CH_3$ |
| $C_2H_5$ | $CH_3$ | $(CH_2)_2$ | 2-pyridyl | $CH(CH_3)(CH_2)_2$ | 4-$FC_6H_4$ | H | $C_2H_5$ |
| H | H | $(CH_2)_2$ | 4-pyridyl | $CH(CH_3)(CH_2)_2$ | 4-$ClC_6H_4$ | $CH_3$ | H |

| $R_4$ | $R_5$ | $alk_2$ | W | $R_4$ | $R_5$ | $alk_2$ | W |
|---|---|---|---|---|---|---|---|
| $CH_3$ | $CH_3$ | $CH_2$ | $C_6H_5$ | $CH_3$ | $CH_3$ | — | 4-pyridyl |
| H | H | $CH_2$ | $C_6H_5$ | $CH_3$ | $CH_3$ | — | 4-piperidyl |
| $CH_3$ | $CH_3$ | $CH_2$ | 4-$FC_6H_4$ | $CH_3$ | H | — | 2-$(C_6H_5)C_6H_{10}$ |
| $CH_3$ | $CH_3$ | — | $C_6H_5$ | H | H | — | 4-$(C_6H_5)C_6H_{10}$ |
| $CH_3$ | $CH_3$ | — | 4-$FC_6H_4$ | $CH_3$ | $CH_3$ | — | 3-$(C_6H_5)C_7H_{12}$ |
| $C_2H_5$ | H | — | 4-$ClC_6H_4$ | $CH_3$ | $CH_3$ | $-CH_2-$ | $CH_3$ |
| $C_2H_5$ | $C_2H_5$ | — | $C_6H_5$ | $CH_3$ | $CH_3$ | $-(CH_2)_3-$ | $CH_3$ |
| H | H | — | 4-$FC_6H_4$ | $CH_3$ | $CH_3$ | $-(CH_2)_6-$ | $CH_3$ |
| $CH_3$ | $CH_3$ | — | $C_3H_5$ | $CH_3$ | $CH_3$ | $-(CH_2)_9-$ | $CH_3$ |
| H | H | — | $C_3H_5$ | $CH_3$ | H | $-(CH_2)_6-$ | $CH_3$ |
| $CH_3$ | $CH_3$ | — | $C_4H_7$ | $C_2H_5$ | $C_2H_5$ | $-(CH_2)_3-$ | $CH_3$ |
| $CH_3$ | H | — | $C_4H_7$ | $CH_3$ | $CH_3$ | $-C(CH_3)_2(CH_2)_5-$ | $CH_3$ |
| $C_2H_5$ | $C_2H_5$ | — | $C_5H_9$ | $CH_3$ | H | $-C(CH_3)_2(CH_2)_5-$ | $CH_3$ |
| $CH_3$ | $CH_3$ | — | $C_5H_9$ | $CH_3$ | $CH_3$ | $-CH(CH_3)CH(CH_3)-(CH_2)_4-$ | $CH_3$ |
| $CH_3$ | H | — | $C_6H_{11}$ | | | | |
| $CH_3$ | H | — | $C_7H_{13}$ | | | | |
| $CH_3$ | $CH_3$ | — | 2-$(C_6H_5)C_3H_4$ | | | | |
| $CH_3$ | $CH_3$ | — | 1-$(C_6H_5)C_4H_6$ | | | | |
| $CH_3$ | $CH_3$ | — | 2-$(C_6H_5)C_5H_8$ | | | | |
| $CH_3$ | H | — | 2-$(C_6H_5)C_5H_8$ | | | | |
| $CH_3$ | $CH_3$ | — | 4-$(C_6H_5)C_6H_{10}$ | | | | |
| $C_2H_5$ | $C_2H_5$ | — | 3-$(C_6H_5)C_6H_{10}$ | | | | |

EXAMPLE 14

The products of Example 13 are converted to compounds having the formula below by the procedures of Examples 1-5.

EXAMPLE 15 dl-6aβ,7,10,10aα-Tetrahydro-1-hydroxy-6,6-dimethyl-3-(1-methyl-3-phenylsulfinylpropyl)-6H-dibenzo[b,d]-pyran-9(8H)-one Equimolar amounts of m-chloroperbenzoic acid and dl-6aβ,7,10,10aα-tetrahydro-1-hydroxy-6,6-dimethyl-3-(1-methyl-3-phenylthiopropyl)-6H-dibenzo[b,d]pyran-9(8H)-one are reacted together in a mixture of chloroform and acetic acid (2:1) at room temperature for 1 hour. The organic phase is washed with water, dried ($MgSO_4$) and evaporated to dryness to give the product.

In like manner the thio others of Example 12 are oxidized to the corresponding sulfoxides of formula

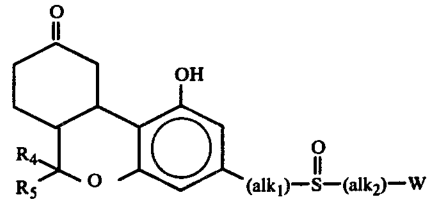

EXAMPLE 16 dl-6a$\beta$,7,10,10a$\alpha$-Tetrahydro-1-hydroxy-6,6-dimethyl-3-(1-methyl-3-phenylsulfonylpropyl)-6H-dibenzo[b,d]-pyran-9(8H)-one The procedure of Example 15 is repeated but using two equivalents of m-chloroperbenzoic acid as oxidizing agent per mole of thio ether reactant.

Similarly, the thio ethers of Example 12 are converted to their corresponding sulfonyl derivatives to give compounds of the formula:

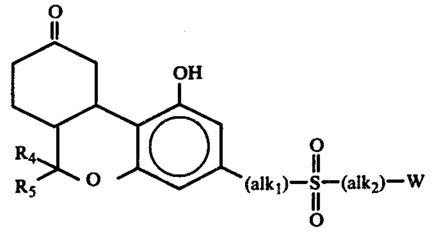

EXAMPLE 17

(−)-Trans 3-(1-methyl-4-phenylbutyl)-6a,7,8,10a-tetrahydro-6,6,9-trimethyl-6H-dibenzo[b,d]pyran-1-$\beta$-ol To a stirred solution of (+) p-mentha-2,8-dien-1-ol (4.9 g., 0.0322 mole) and 5-(1-methyl-4-phenylbutyl)-resorcinol (8.2 g., 0.032 mole) in dry methylene chloride (200 ml.) is added anhydrous magnesium sulfate (4 g., 0.332 mole). The mixture is stirred under a nitrogen atmosphere and cooled to 0° C. Freshly distilled boron trifluoride etherate (2 ml., 0.016 mole) is then added dropwise over a 5 minute period. The reaction mixture is stirred for 1.5 hours at 0° C. and anhydrous sodium bicarbonate (10 g., 0.119 mole) is added. Stirring is continued until the dark color fades. The reaction mixture is filtered and evaporated to give 11.7 g. (93.6%) of a resinous product. The product is purified via column chromatography on an activated magnesium silicate, available from M C & B Manufacturing Chemists, 2909 Highland Avenue, Cincinnati, Oh., under the trademark "Florisil", to give 3.4 g. (27%) of the desired product as a mixture of optically active diasteriomers.*

*$[\alpha]_d^{25}$ (C = 1.0, $CHCl_3$) = −100.8°.

NMR $\delta_{CDCl_3}^{TMS}$ 1.1 (S,3,$C_1$-methyl), 1.3, 1.45 (2S,6,gem dimethyls), 1.75 (S,3,$C_9$-methyl), 0.7–3.0 (M,12,remaining protons), 3.0–3.6 (M,1,$C_{10\alpha}$-proton), 5.05 (S,1,hydroxyl,$D_2O$ overlay), 6.1 (S,1,$C_4$-proton, aromatic), 6.4 (M,2,$C_2$-proton,aromatic,$C_{10}$-proton), 7.1–7.5 (M,5,aromatic protons).

MS: (mol.ion) 390

It is converted to the optically active 6a$\beta$,7,10,10a$\alpha$-tetrahydro-1-hydroxy-3-(1-methyl-4-phenylbutyl)-6,6-dimethyl-6H-dibenzo[b,d]pyran-9(8H)-one diasteriomers according to the procedure of Wildes et al., *J. Org. Chem.*, 36, 721-3 (1971)

EXAMPLE 18 dl-6a$\beta$,7,10,10a$\alpha$-tetrahydro-1-(4-morpholinobutyryloxy)-6,6-dimethyl-3-(1-methyl-4-phenylbutyl)-6H-dibenzo[b,d]pyran-9(8H)-one hydrochloride To a stirred solution of dl-6a$\beta$,7,10,10a$\alpha$-tetrahydro-1-hydroxy-6,6-dimethyl-3-(1-methyl-4-phenylbutyl)-6H-dibenzo[b,d]pyran-9(8H)-one (0.52 g., 1.28 mM) in dry methylene chloride (25 ml.) is added 4-morpholinobutyric acid hydrochloride (0.268 g., 1.28 mM). The mixture is stirred at room temperature under a nitrogen atmosphere. A 0.1 M solution of dicyclohexylcarbodiimide in methylene chloride (12.8 ml., 1.28 mM) is added dropwise and the mixture stirred for 24 hours. It is filtered and evaporated to give the title product, which is purified by column chromatography on silica gel.

EXAMPLE 19

The procedure of Example 18 is repeated but using the appropriate dl-6a$\beta$,7,10,10a$\alpha$-tetrahydro-6,6-$R_4R_5$-3-(Z-W)-6H-dibenzo[b,d]pyran-9(8H)-ones of Examples 4, 9 and those produced as penultimate products in the procedures of Examples 11, 12 and 14; and the appropriate alkanoic acid or acid of formula HOOC—$(CH_2)_p$—$NR_2R_3$.HCl to produce esters of the formula

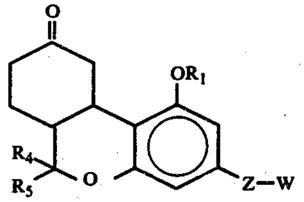

wherein $R_4$, $R_5$, Z and W are as defined in Examples 4, 9, 11, 12 and 14 and $R_1$ is

| $R_1$* | $R_1$* |
|---|---|
| —$COCH_3$ | —$CO(CH_2)_3NHC_4H_9$ |
| —$COCH_2CH_3$ | —$CO(CH_2)_2N(C_4H_9)_2$ |
| —$CO(CH_2)_3CH_3$ | —$COCH_2$-piperidino |
| —$COCH_2NH_2$ | —$COCH_2$-pyrrolo |
| —$CO(CH_2)_2NH_2$ | —$COCH_2$-(N-methyl)piperidino |
| —$CO(CH_2)_4NH_2$ | —$CO(CH_2)_2$-morpholino |
| —$COCH_2N(CH_3)_2$ | —$CO(CH_2)_2$-N-butyl)piperidino |
| —$CO(CH_2)_2N(C_2H_5)_2$ | —$CO(CH_2)_3$-pyrrolidino |
| —$CO(CH_2)_4NHCH_3$ | —$CO(C_2H_4)$-(N-ethyl)piperidino |
| —$CONH_2$ | —CO-piperidino |
| —$CON(CH_3)_2$ | —CO-(N-methyl)piperidino |
| —$CON(C_4H_9)_2$ | —CO-morpholino |
| —$CON(C_2H_5)_2$ | —CO-pyrrolo |

*Basic esters are obtained as their hydrochloride salts. Careful neutralization with sodium hydroxide affords the free ester.

EXAMPLE 20 dl-6a$\beta$,7,8,9,10,10a$\alpha$-Hexahydro-1-(4-morpholinobutyryloxy)-6,6-dimethyl-3-(1-methyl-4-phenylbutyl)-6H-dibenzo[b,d]pyran-9$\beta$-ol hydrochloride The title product of Example 5 is esterified according to the procedure of Example 18 to produce the above-named ester salt.

In like manner, the remaining products of Example 5 and those of Examples 10–12 and 14 are converted to esters having the formula shown below wherein $R_4$, $R_5$, Z and W are as defined in said Examples and $R_1$ has the values given below:

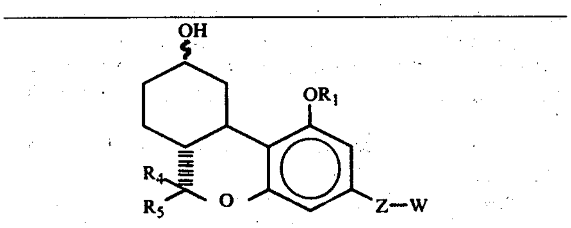

| $R_1$ | $R_1$ |
|---|---|
| $-COCH_3$ | $-COCH_2$-pyrrolo |
| $-CO(CH_2)_2CH_3$ | $-COCH_2$-pyrrolidino |
| $-CO(CH_2)_3CH_3$ | $-COCH_2$-morpholino |
| $-COCH_2NH_2$ | $-COCH_2$-(N-methyl)piperazino |
| $-COCH_2N(CH_3)_2$ | $-COCH_2$-(N-butyl)piperazino |
| $-CO(CH_2)_2NHCH_3$ | $-CO(CH_2)_2$-piperidino |
| $-CO(CH_2)_2N(i\text{-}C_3H_7)_2$ | $-CO(CH_2)_2$-(N-isopropyl)piperazino |
| $-COCH_2N(C_4H_9)_2$ | $-CO(CH_2)_3$-pyrrolidino |
| $-CO(CH_2)_4N(C_2H_5)_2$ | $-CO(CH_2)_4$-(N-ethyl)piperazino |
| $-CONH_2$ | —CO-piperidino |
| $-CON(CH_3)_2$ | —CO-(N-methyl)piperazino |
| $-CONHC_2H_5$ | —CO-morpholino |
| $-CON(C_4H_9)_2$ | —CO-pyrrolo |

EXAMPLE 21 dl-6a,7-Dihydro-1-hydroxy-6,6-diemthyl-3-(1-methyl-4-phenylbutyl)-6H-dibenzo[b,d]pyran-9(8H)-one

(A) dl-Ethyl 5-Hydroxy-4-methyl-7-(1-methyl-4-phenylbutyl)-coumarin-3-propionate A mixture of 2-(3,5-dihydroxphenyl)-5-phenylpentane (33 g., 0.13 M), (Preparation C) diethyl α-acetoglutarate (32.2 g., 0.14 M) and phosphorous oxychloride (20 g., 0.13 M), protected from atmospheric moisture, is stirred at room temperature. After 10 days, the mixture is dissolved in chloroform, washed three times with water, dried ($Na_2SO_4$), and evaporated. The residue is subjected to silica gel chromatography (eluents - 9 benzene:1 ether) to yield 22 g. of the desired ester, m.p. 58°-70° C. from hexane. Further recrystallization from ethyl acetate/hexane affords an analytical sample: m.p. 78°-85° C.

Analysis: Calc'd for $C_{26}H_{30}O_5$: C, 73.91; H, 7.16%. Found: C, 73.82; H, 7.13%.

MS: (mol.ion) 422

(B) dl-7,10-Dihydro-1-hydroxy-3-(1-methyl-4-phenylbutyl)-6H-dibenzo[b,d]pyran-6,9(8H)-dione To the sodium hydride powder obtained by washing 10.0 g. (0.21 mole) of 50% sodium hydride in mineral oil dispersion with dry hexane is added 20.6 g. (0.049 mole) of the ester of part A of this example and the two powders are mixed thoroughly. The reaction flask is cooled to 15°-17° C. and dimethyl sulfoxide (200 ml.) is added directly into the reaction flask. After stirring for an additional hour at 15°-17° C., the reaction is kept overnight in the refrigerator. After warming to room temperature the reaction mixture is poured into a rapidly stirred mixture of 600 ml. of ice and water and 40 ml. of concentrated hydrochloric acid, more ice being added as needed to keep the mixture cold. The slurry thus produced is stirred for an additional hour and is then decanted. The residual gum is heated on the steam bath with excess concentrated sodium bicarbonate solution and, while still warm, the resultant solid is filtered. The filter cake is washed with bicarbonate solution and water and recrystallized from ethyl acetate/hexane to give 4.5 g. of cyclized product, m.p. 163°-164° C. Further purification is achieved by recrystallization from methanol; m.p. 166°-167° C.

Analysis: Calc'd for $C_{24}H_{24}O_4$: C, 76.57; H, 6.43%. Found: C, 76.50; H, 6.56%.

MS: (mol.ion) 376

(C) dl-7,8,9,10-Tetrahydro-1-hydroxy-3-(1-methyl-4-phenylbutyl)spiro[6H-dibenzo[b,d]pyran-9,2'-[1',3']dioxolan]-6-one A solution of 0.031 mole of the cyclized product of part B of this example in benzene (500 ml.) containing ethylene glycol (10 ml.) and p-toluenesulfonic acid (10 mg.) is heated overnight under reflux (Dean-Stark trap). The solution is cooled, poured into water containing excess sodium bicarbonate and the organic phase separated, dried ($Na_2SO_4$) and evaporated to yield the desired ketal.

(D) dl-6a,7-Dihydro-1-hydroxy-6,6-dimethyl-3-(1-methyl-4-phenylbutyl)-6H-dibenzo[b,d]pyran-9(8H)-one A slurry of 0.175 mole of the above produced ketal in ether (1.5 liters) is added over 90 minutes to the Grignard reagent prepared from magnesium (44.6 g., 1.84 g-atoms) and methyl iodide (110 ml., 251 g., 1.77 moles) in ether (1.8 liters). After refluxing for 2 days the reaction is treated carefully with 1N hydrochloric acid (200 ml.), and then with 6N hydrochloric acid (740 ml.). The mixture is stirred vigorously for 1 hour and then the ether layer washed once with water and once with 5% sodium bicarbonate. The ether layer is dried ($Na_2SO_4$) and concentrated to yield the desired unsaturated ketone. If desired, it is purified by crystallization and/or column chromatography (see Examples 3 and 8).

In like manner, the remaining 1-(Z-W-substituted)-3,5-dihydroxybenzenes of Preparation C and those of Preparations D, E, K, M, Q, R and T are converted to the corresponding dl-6a,7-dihydro-1-hydroxy-6,6-dimethyl-3-(Z-W)-6H-dibenzo[b,d]-pyran-9(8H)-ones.

EXAMPLE 22 dl-6aβ,7,10,10aα-Tetrahydro-1-hydroxy-6,6-dimethyl-3-(1-methyl-4-phenylbutyloxy)-6H-dibenzo[b,d]pyran-9(8H)-one, Ethylene Ketal A solution of dl-6aβ,7,10,10aα-tetrahydro-1-hydroxy-6,6-dimethyl-3-(1-methyl-4-phenylbutyloxy)-6H-dibenzo[b,d]pyran-9(8H)-one (60 mg., 0.145 mM), ethylene glycol (0.5 ml.), benzene (10 ml.) and a crystal of p-toluenesulfonic acid is heated at reflux for three hours. The reaction mixture is then cooled and concentrated. The concentrate is shaken up in chloroform and the chloroform phase washed first with sodium bicarbonate and then with water. It is then dried ($MgSO_4$) and concentrated to give the ketal as a light brown oil (63 mg.).

Repetition of this procedure but using propylene glycol, trimethylene glycol and tetramethylene glycol, in place of ethylene glycol, affords the corresponding ketals.

By means of this procedure the ketone products of Examples 3, 4, 8, 9, 11, 12, 14-16, 18, 19 and 21 are converted to the corresponding ethylene, trimethylene and tetramethylene ketals.

EXAMPLE 23 dl-5-Hydroxy-2,2-dimethyl-7-(2-heptylmercapto)-4-chromanone

To a solution of 5-hydroxy-7-mercapto-2,2-dimethyl-4-chromanone (19.7 g., 87.1 mM) and potassium hydroxide (2.44 g., 43.5 mM) in N,N-dimethylformamide (58 ml.) is added with stirring 2-bromoheptane (15.77 g., 88.0 mM). The mixture is heated for four days at 100° C., cooled to room temperature and then added to a mixture of aqueous sodium hydroxide (110 ml. of 1N), water (45 ml.) and chloroform (150 ml.). The mixture is agitated, the phases separated and the aqueous layer extracted with more chloroform (150 ml.). The combined chloroform layers are washed with 1N sodium hydroxide (2 × 100 ml.) dried over sodium sulfate and concentrated to an oil. The unreacted 2-bromoheptane is removed by distillation and the residue purified by silica gel chromatography to give the title product.

The following compounds are similarly prepared from appropriate reactants of the formula Br-$(alk_2)_n$-W from the appropriate 5-hydroxy-7-mercapto-2,2-$R_4R_5$-substituted-4-chromanone:

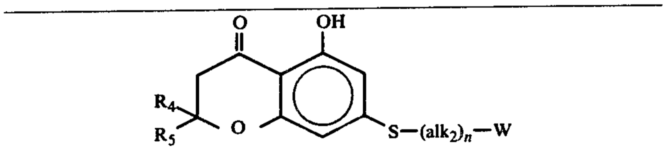

| $R_4$ | $R_5$ | n | $(alk_2)$ | W |
|---|---|---|---|---|
| H | $CH_3$ | 1 | $-CH(CH_3)(CH_2)_4-$ | $CH_3$ |
| $C_2H_5$ | $C_2H_5$ | 1 | $-CH(CH_3)(CH_2)_4-$ | $CH_3$ |
| $CH_3$ | $CH_3$ | 1 | $-CH(CH_3)(CH_2)_3-$ | $C_6H_5$ |
| H | $CH_3$ | 1 | $-CH(CH_3)(CH_2)_3-$ | $C_6H_5$ |
| $CH_3$ | $CH_3$ | 1 | $-CH(CH_3)(CH_2)_2-$ | $C_6H_5$ |
| $CH_3$ | $CH_3$ | 1 | $-CH(CH_3)(CH_2)_3-$ | 4-pyridyl |
| H | H | 1 | $-CH(CH_3)(CH_2)_3-$ | 4-pyridyl |
| $CH_3$ | $CH_3$ | 1 | $-CH_2-$ | $C_6H_5$ |
| $CH_3$ | $CH_3$ | 1 | $-(CH_2)_4-$ | $C_6H_5$ |
| $CH_3$ | $C_2H_5$ | 1 | $-(CH_2)_7-$ | $C_6H_5$ |
| $CH_3$ | $CH_3$ | 1 | $-C(CH_3)_2(CH_2)_5-$ | $CH_3$ |
| $CH_3$ | H | 1 | $-C(CH_3)_2(CH_2)_5-$ | $CH_3$ |
| $CH_3$ | $CH_3$ | 1 | $-CH(CH_3)CH(CH_3)(CH_2)_4-$ | $CH_3$ |
| H | $CH_3$ | 1 | $-CH(CH_3)CH(CH_3)(CH_2)_4-$ | $CH_3$ |
| $CH_3$ | $CH_3$ | 1 | $-(CH_2)_3-$ | 3-pyridyl |
| $CH_3$ | H | 1 | $-(CH_2)_3-$ | 4-pyridyl |
| H | $CH_3$ | 1 | $-CH(CH_3)CH_2-$ | 2-pyridyl |
| H | H | 1 | $-(CH_2)_2-$ | 4-pyridyl |
| $C_2H_5$ | $CH_3$ | 1 | $-CH(CH_3)(CH_2)_2-$ | 4-piperidyl |
| $CH_3$ | $CH_3$ | 0 | — | $C_6H_5$ |
| $CH_3$ | $CH_3$ | 0 | — | $C_6H_{11}$ |
| H | $CH_3$ | 0 | — | 4-$FC_6H_4$ |
| $C_2H_5$ | H | 0 | — | 4-$ClC_6H_4$ |
| $C_2H_5$ | $C_2H_5$ | 0 | — | $C_6H_5$ |
| $CH_3$ | $CH_3$ | 0 | — | $C_3H_5$ |
| H | H | 0 | — | $C_3H_5$ |
| $CH_3$ | H | 0 | — | $C_4H_7$ |
| $CH_3$ | $CH_3$ | 0 | — | $C_5H_9$ |
| $CH_3$ | H | 0 | — | $C_7H_{13}$ |
| $CH_3$ | $CH_3$ | 0 | — | 2-$(C_6H_5)C_3H_4$ |
| $CH_3$ | $CH_3$ | 0 | — | 2-$(C_6H_5)C_5H_8$ |
| $CH_3$ | $CH_3$ | 0 | — | 4-$(C_6H_5)C_6H_{10}$ |
| $CH_3$ | $CH_3$ | 0 | — | 3-$(C_6H_5)C_7H_{12}$ |
| H | H | 0 | — | 4-$(C_6H_5)C_6H_{10}$ |
| $CH_3$ | $CH_3$ | 0 | — | 4-pyridyl |
| $CH_3$ | $CH_3$ | 0 | — | 4-piperidyl |

EXAMPLE 24 dl-6aβ,7,10,10aα-Tetrahydro-1-acetoxy-6,6-dimethyl-3-(1-methyl-4-phenylbutoxy)-6H-dibenzo[b,d]pyran-9(8H)-one Pyridine (15 ml.), acetic anhydride (15 ml.) and dl-6aβ,7,10,10aα-tetrahydro-1-hydroxy-6,6-dimethyl-3-(1-methyl-4-phenylbutoxy)-6H-dibenzo[b,d]pyran-9(8H)-one (4.06 g.) are combined at 0° C. and the mixture stirred for ½ hour at 0° C. The reaction mixture is poured onto ice/water and acidified with dilute hydrochloric acid. The acidified mixture is extracted with ethyl acetate (2 × 100 ml.), the extracts combined and washed with brine. The extract is then dried ($MgSO_4$) and evaporated to give a colorless oil which is crystallized from ether-pentane. Yield = 1.69 g.; m.p. 95°-96° C.

Analysis: Calc'd for $C_{28}H_{34}O_5$: C, 74.64; H, 7.61%. Found: C, 74.55; H, 7.59%.

Evaporation of the mother liquor gives a second crystalline fraction which is digested in hexane. Yield = 1.74 g.; m.p. 94°-96° C.

By means of this procedure but using the appropriate alkanoic acid anhydride and the appropriate dl-6aβ,7,10,10aα-tetrahydro-6,6-$R_4$,$R_5$-3-(Z-W)-6H-dibenzo[b,d]pyran-9(8H)-ones of Examples 4, 9, 11, 12 and 14 as reactants, affords the propionyloxy, butyryloxy and valeryloxy esters thereof.

Reduction of the 9-keto group of the thus-produced mono esters according to the procedure of Example 5 affords the corresponding 9-hydroxy derivatives. A mixture of the 9α- and 9β-isomers is produced.

EXAMPLE 25 dl-6aβ,7,8,9,10,10aα-Hexahydro-1,9-diacetoxy-6,6-dimethyl-3-(1-methyl-4-phenylbutyl)-6H-dibenzo[b,d]pyran A solution of dl-6aβ,7,8,9,10,10aα-hexahydro-1-hydroxy-6,6-dimethyl-3-(1-methyl-4-phenylbutyl)-6H-dibenzo[b,d]pyran-9β-ol (2.0 g.) in pyridine (20 ml.) is treated at 10° C. with acetic anhydride (20 ml.) and the mixture stirred for 18 hours under nitrogen. The reaction mixture is worked up according to the procedure of Example 24.

In like manner, the 1,9-dihydroxy compounds of Examples 5, 10-12, 14 and 15 are converted to their diacetoxy, dipropionyloxy, dibutyryloxy and divaleryloxy esters.

EXAMPLE 26 dl-6aβ,7,10,10aα-Tetrahydro-1-(4-N-piperidyl-butyroxy)6,6-dimethyl-3-[2-(5-phenyl)pentyloxy]-6H-dibenzo[b,d]pyran-9(8H)-one hydrochloride A mixture of dl-6aβ,7,10,10aα-tetrahydro-1-hydroxy-6,6-dimethyl-3-[2-(5-phenyl)pentyloxy]-6H-dibenzo[b,d]pyran-9(8H)-one (1.26 g., 3.08 mmoles), 4-N-piperidyl butyric acid hydrochloride (0.639 g., 3.08 mmoles) and dicyclohexylcarbodiimide (0.698 g., 3.39 mmoles) in dry dichloromethane (3.5 ml.) is stirred at 20° C. for 18 hours. The reaction is cooled to 0° C., stirred for ½ hour and filtered. The filtrate is evaporated to an oil which is washed with ether (3 ×) and evaporated to yield 1.78 g. (97%) of dl-6aβ,7,10,10aα-tetrahydro-1-(4-N-piperidyl-butyroxy)-6,6-dimethyl-3-[2-(5-phenyl)pentyloxy]-6H-dibenzo[b,d]pyran-9(8H)-one hydrochloride as a solid, white foam.

IR; (KBr) NH ⊕ 2667, 2564, C = O 1779 and 1730 $cm^{-1}$.

MS (mol.ion): (M β -HCl), 407, 262, 247, 154, 98 and 91.

PREPARATION A

2-Bromo-5phenylpentane

To phosphorus pentabromide, prepared by addition of bromine (9.0 g.) in methylene chloride (10 ml.) to phosphorous tribromide (15.0 g.) in methylene chloride (15 ml.) at 0° C., is added 5-phenyl-2-pentanol (8.2 g.) in metnhylene chloride at 0° C. The mixture is stirred for 2.5 hours at 0° C. and is then allowed to warm to room temperature. Water (50 ml.) is added, the mixture stirred for 1 hour and the methylene chloride layer separated. The extraction is repeated and the combined extracts washed with water, saturated sodium bicarbonate solution, brine and then dried over magnesium sulfate. Concentration of the dried extracts gives 12.4 g. of title product as a light yellow oil.

NMR: $\delta_{CDCl_3}^{TMS}$ 1.6 (D, 3, methyl, J = 7Hz), 1.6–2.0 (M, 4, ethylene), 2.3–3.0 (bd, T, 2, benzylic-methylene), 3.7–4.2 (M, 1, methine), 6.9–7.4 (M, 5, aromatic).

PREPARATION B 2-(3,5-Dimethoxyphenyl)-5-phenylpentane

A solution of 1-bromopropylbenzene (51.7 g.) in ether (234 ml.) is added dropwise over a 2-hour period to a refluxing mixture of magnesium (7.32 g.) in ether (78 ml.). The reaction mixture is refluxed for 30 minutes longer and then a solution of 3,5-dimethoxy-acetophenone (50 g.) in ether (78 ml.) is added dropwise and heated to reflux for 1.5 hours. The reaction is quenched by addition of saturated ammonium chloride (234 ml.), the ether layer is separated and the aqueous phase extracted with ether (3 × 200 ml.). The combined ether extracts are dried over magnesium sulfate and concentrated under vacuum to yield 81 g. of an oil. Forty grams of the oil is hydrogenated in a mixture containing ethanol (300 ml.), concentrated hydrochloric acid (2 ml.) and 5% palladium-on-carbon (5 g.). The catalyst is filtered off and the ethanol removed under vacuum. The residue is distilled under vacuum yielding 28 g. of 2-(3,5-dimethoxyphenyl)-5-phenylpentane (b.p. 0.125 mm., 154°-159° C.).

NMR: $\delta_{CDCl_3}^{TMS}$ 1.25 (d,3,α-$CH_3$), 1.3-2.1 (M,4,ethylene), 2.2-2.9 (M, 3,benzylic-methylene, methinyl), 3.45 (S,6,methoxyl), 6.2-6.7 (M,3,aromatic), 7.2 (S,5,aromatic).

PREPARATION C 2-(3,5-Dihydroxyphenyl)-5-phenylpentane

A mixture of 2-(3,5-dimethoxyphenyl)-5-phenylpentane (22 g.) and pyridine hydrochloride (94 g.) under nitrogen is heated to 190° C. for 2 hours with vigourous stirring. The reaction mixture is cooled, dissolved in 6N hydrochloric acid (200 ml.) and diluted with water to 600 ml. The aqueous solution is extracted with ethyl acetate (4 × 100 ml.), the ethyl acetate extracts dried over sodium sulfate and concentrated under vacuum to yield 24 g. of crude product. The product is purified by silica gel chromatography to yield 19.2 g. of 2-(3,5-dihydroxyphenyl)-5-phenylpentane as an oil.

NMR: $\delta_{CDCl_3}^{TMS}$ 1.1 (d,3,α-methyl), 1.35-1.65 (M,4,ethylene), 2.2-2.8 (M,3,benzylic-methylene, methinyl), 6.1-6.5 (M,3,aromatic), 6.65 (bd.S.,2, hydroxyl), 7-7.4 (M,5,aromatic).

Following the procedures of Preparations B and C, the compounds listed below are prepared by substituting the appropriate 1-bromoalkylbenzene for 1-bromopropylbenzene:

2-(3,5-(dihydroxyphenyl)-6-phenylhexane

NMR: $\delta_{CDCl_3}^{TMS}$ 1.1 (D,3,α-methyl, J-7 cps), 1.0-1.9 [M,6,$\Phi CH_2CH_2)_3$—$CH(CH_3)$—Ar], 2.2-2.8 (M,3,benzylic methylene, methinyl), 6.0 (bd.S.,2,phenolic OH), 6.2-6.4(M,3,aromatic), 7.1-7.4(M,5,aromatic).

1-(3,5-dihydroxyphenyl)-2-phenylethane m.p.: 76°-77° C.

2-(3,5-dihydroxyphenyl-4-phenylbutane (an oil)

NMR: $\delta_{CDCl_3}^{TMS}$ 1.1, 1.25 (d,2,methyl), 1.45-2.0 (M,2,methylene), 2.15-2.7 (M,3,benzylic-methylene, methinyl), 6.3 (S,3,aromatic), 6.85 (S,2,hydroxyl-$D_2O$ overlay), 7.1 (S,5, aromatic).

The following compounds are prepared in like manner from the appropriate alcohol and 3,5-dimethoxybenzaldehyde or 3,5-dimethoxyacetophenone by the methods of Preparations A, B and C:

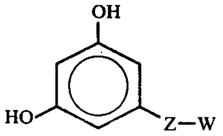

| Z | W |
|---|---|
| $CH(CH_3)CH_2$ | $C_5H_9$ |
| $CH(CH_3)(CH_2)_2$ | $C_5H_9$ |
| $CH(CH_3)CH_2$ | $C_3H_5$ |
| $CH(CH_3)CH(CH_3)$ | $C_6H_{11}$ |
| $CH(CH_3)(CH_2)_3$ | $C_6H_{11}$ |
| $CH(CH_3)(CH_2)_4$ | $C_5H_9$ |
| $CH(CH_3)(CH_2)_5$ | $C_6H_{11}$ |
| $CH(C_2H_5)(CH_2)_2$ | $C_6H_{11}$ |
| $(CH_2)_3$ | $C_5H_9$ |
| $CH(C_2H_5)(CH_2)_3$ | $C_6H_5$ |
| $C(CH_3)_2$ | $C_6H_5$ |
| $(CH_2)_4$ | $C_6H_5$ |
| $(CH_2)_2CH(C_2H_5)$ | $C_6H_5$ |
| $CH(CH_3)CH_2CH(C_2H_5)$ | $C_6H_5$ |

PREPARATION D 1-(3,5-Dihydroxyphenyl)-2-methyl-4-phenylbutane

A solution of n-butyl lithium (29 ml. of 2.2M) is added dropwise to 3,5-dimethoxybenzyl triphenylphosphonium bromide (31.5 g.) in tetrahydrofuran (200 ml.) with stirring and the resulting deep red solution is stirred for one-half hour. Benzyl acetone (9.4 g.) is added dropwise and the reaction mixture stirred for 12 hours. It is then adjusted to pH 7 by addition of acetic acid and concentrated under reduced pressure. The residue is extracted with methylene chloride and the extract evaporated to give crude 1-(3,5-dimethoxyphenyl)-2-methyl-4-phenyl-1-butene as an oil. It is purified by chromatography on silica gel (400 g.) and elution with benzene. Yield: 10 g. as an oil.

NMR: $\delta_{CDCl_3}^{TMS}$ 1.95 (S,3), 2.3–3.1 (M,4), 3.8 (S,6), 6.15–6.6 (M,3), 7.1–7.5 δ(M,6).

The 1-(3,5-dimethoxyphenyl)-2-methyl-4-phenyl-1-butene (9.4 g.) thus prepared is dissolved in ethanol (250 ml.) and catalytically hydrogenated at 45 p.s.i. in the presence of palladium-on-charcoal (1 g. of 10%) and concentrated hydrochloric acid (1 ml.). Yield: 9.4 g. of 1-(3,5-dimethoxyphenyl)-2-methyl-4-phenylbutane as an oil.

NMR: $\delta_{CDCl_3}^{TMS}$ 0.9 (d,3), 1.35–1.95 (M,3), 2.2–2.9 (M,4), 3.75 (S,6), 6.35 (S,3), 7.25 δ(S,5).

It is demethylated according to the procedure of Preparation C to give 1-(3,5-dihydroxyphenyl)-2-methyl-4-phenylbutane.

The 3,5-dimethoxybenzyl triphenylphosphonium bromide is prepared by refluxing a mixture of 3,5-dimethoxybenzyl bromide (12 g.) and triphenylphosphine (14.2 g.) in acetonitrile (200 ml.) for 1 hour. The reaction mixture is then cooled and the crystalline product recovered by filtration, washed with ether and dried (20 g.); m.p. 269°-270° C.

PREPARATION E

2-Methyl-2-(3,5-dihydroxyphenyl)-5-phenylpentane

To a solution of the Grignard reagent prepared from 2-phenylbromoethane (5.5 g.), magnesium (0.8 g.) and dry ether (60 ml.) is added a solution of 2-methyl-2-(3,5-dimethoxyphenyl)propionitrile (2.75 g.) in dry ether (20 ml.). The ether is distilled off and replaced by dry benzene (50 ml.) and the mixture refluxed for 48 hours. It is then decomposed by careful treatment with dilute sulfuric acid and heated on a steam bath for 1 hour. The mixture is then extracted with ether, the extract dried ($MgSO_4$) and concentrated to an oil. Distillation of the oil in vacuo affords 2-methyl-2-(3,5-dimethoxyphenyl)-5-phenyl-3-pentanone; b.p. 168° C./0.2 mm. (Yield: 2.32 g., 60%)

The thus-produced pentanone (58 g.) is dissolved in ethanol (400 ml.) and treated with sodium borohydride (10 g.) at room temperature. The reaction mixture is stirred for 12 hours and is then cooled and neutralized with 6N hydrochloric acid. The ethanol is removed under reduced pressure and the residue extracted with ether. The extract is dried ($MgSO_4$) and concentrated to give 2-methyl-2-(3,5-dimethoxyphenyl)-5-phenyl-3-pentanol as an oil (52 g., 88% yield).

The pentanol (16 g.) is taken up in ether (100 ml.) and reacted with powdered potassium (2.5 g.) in ether (200 ml.). Carbon disulfide (equimolar to the potassium) is added and the mixture stirred for a half hour. Methyl iodide (9.0 g.) is then added and the reaction mixture stirred for 6 hours. The resulting suspension is filtered and the filtrate concentrated under reduced pressure. The residue is taken up in ethanol (150 ml.), Raney nickel added (25 g.) and the mixture refluxed for 18 hours. Evaporation of the alcohol and distillation of the residue gives 2-methyl-2-(3,5-dimethoxyphenyl)-5-phenyl-3-pentene.

The pentene derivative is catalytically hydrogenated according to the procedure of Preparation D and the resulting 2-methyl-2-(3,5-dimethoxyphenyl)-5-phenyl-3-pentane dimethylated via the procedure of Preparation C to give the product.

PREPARATION F 3,5-Dibenzyloxyacetophenone

Over a period of 1.5 hours, methyl lithium (531 ml. of a 2 molar solution, 1.06 M) is added under a nitrogen atmosphere to a rapidly stirring solution of 3,5-dibenzyloxybenzoic acid (175 g., 0.532 M) in ether (250 ml.) - tetrahydrofuran (1400 ml.) maintained at 15°-20° C. After stirring an additional 0.75 hour at 10°-15° C., water (600 ml.) is slowly added keeping the reaction temperature below 20° C. The aqueous layer is separated and extracted with ether (3 × 250 ml.). The organic phases are combined, washed with saturated sodium chloride solution (4 × 300 ml.), dried over sodium sulfate, and concentrated under vacuum to give an oil which slowly crystallized from isopropylether. The crude product is recrystallized from ether-hexane to yield 104.7 g. (59%) of product; m.p. 59°-61° C.

PREPARATION G

Ethyl 3-(3,5-Dibenzyloxyphenyl)crotonate (Wittig Reaction)

A mixture of 3,5-dibenzyloxyacetophenone (43.2 g., 0.13 mole) and carbethoxymethylenetriphenylphosphorane (90.5 g., 0.26 mole) is heated under a nitrogen atmosphere at 170° C. for 4 hours. The clear melt is cooled to room temperature, triturated with ether and the precipitate of triphenyl phosphine oxide removed by filtration. The filtrate is concentrated under vacuum to an oily residue which is chromatographed over silica gel (1500 g.) and eluted with benzene:hexane solutions of increasing benzene concentration beginning with 40:60 and ending with 100% benzene. Concentration of appropriate fractions gives an oily residue which is crystallized from hexane. Yield: 40.2 g. (77%); m.p. 73°-75° C.

Analysis: Calc'd for $C_{26}H_{26}O_4$: C, 77.58; H, 6.51%. Found: C, 77.72; H, 6.60%.

In like manner, ethyl 3-(3,5-dimethoxyphenyl)crotonate is prepared from 3,5-dimethoxyacetophenone (51.7 g.) and carbethoxymethylene triphenylphosphorane (200 g.). Yield = 61.8 g., 86%, b.p. 146°-162° C. at 0.3 mm.

PREPARATION H 3-(3,5-Dibenzyloxyphenyl)-1-butanol

A solution of ethyl 3-(3,5-dibenzyloxyphenyl)crotonate (24.1 g., 60 mM) in ether (250 ml.) is added to a mixture of lithium aluminum hydride (3.42 g., 90 mM) and ether (250 ml.). Aluminum chloride (0.18 g., 1.35 mM) is added and the mixture refluxed for 12 hours and then cooled. Water (3.4 ml.), sodium hydroxide (3.4 ml. of 6N) and water (10 ml.) are then added successively to the reaction mixture. The inorganic salts which precipitate are filtered off and the filtrate is then concentrated -continued

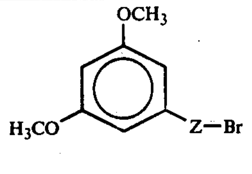

| Z |
|---|
| $C(C_2H_5)CH_2$ |

PREPARATION M

4-(3,5-Dihydroxypenyl)-1-(4-pyridyl)pentane

A mixture of 3-(3,5-dimethoxyphenyl)butyl triphenylphosphonium bromide (19.0 g., 35.4 mmoles) in dimethylsulfoxide (50 ml.) is added to 4-pyridinecarboxaldehyde (3.79 g., 35.4 mmoles) in tetrahydrofuran (40 ml.). The resulting mixture is then added dropwise to a slurry of 50% sodium hydride (1.87 g., 39 mmoles) in tetrahydrofuran (20 ml.) under a nitrogen atmosphere at 0°-5° C. Following completion of addition, the mixture is stirred for one hour at 0°-5° and then concentrated under reduced pressure. The concentrate is diluted with water (200 ml.) and then acidified with 6N HCl. The aqueous acid solution is extracted with benzene (4 × 50 ml.). It is then made basic and extracted with ethyl acetate (3 × 50 ml.). Evaporation of the combined extracts after drying ($MgSO_4$) affords 4-(3,5-dimethoxyphenyl)-1-(4-pyridyl)-1-pentene (7.1 g., 70%) as an oil.

Catalytic hydrogenation of the thus-produced pentene derivative according to the procedure given in Preparation D gives 4-(3,5-dimethoxyphenyl)-1-(4-pyridyl)pentane in quantitative yield; m.p. 131°-133° C.

The pentane derivative thus obtained is demethylated by heating a mixture of the compound (7.15 g., 25 mmoles) and pyridine hydrochloride (35 g.) under a nitrogen atmosphere at 210° C. for 8 hours. The hot mixture is poured into water (40 ml.) and the resulting solution made basic with 6N sodium hydroxide. Water and pyridine are removed by distillation in vacuo. Ethanol (50 ml.) is added to the residue and the inorganic salts which precipitate are filtered off. The filtrate is concentrated in vacuo and the residue chromatographed on silica gel (150 g.) using as eluting agents 5% ethanol/benzene (4 liters), 10% ethanol/benzene (1 liter), 13% ethanol/benzene (1 liter) and 16% ethanol/benzene (5 liters). The product is isolated as a glassy solid by concentration of appropriate fractions of the eluate. Yield = 5.0 g. (78%).

The 3-(3,5-dimethoxyphenyl)butyltriphenylphosphonium bromide is prepared by refluxing a mixture of 1-bromo-3-(3,5-dimethoxyphenyl)butane (21.5 g., 78.5 mmoles) and triphenyl phosphine (20.5 g., 78.5 mmoles) in xylene (60 ml.) for 18 hours. The reaction mixture is then cooled to room temperature and filtered. The filter cake is washed with ether and dried in a vacuum desicator to give 36.4 g. (86%) yield of product; m.p. 190°-200° C.

Repetition of this procedure but using the appropriate bromo-(3,5-dimethoxyphenyl)alkane and the appropriate aldehyde or ketone affords the following compounds.

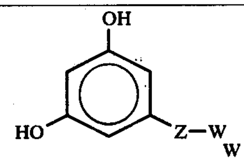

| Z | W |
|---|---|
| $(CH_2)_3$ | 2-pyridyl |
| $(CH_2)_3$ | 3-pyridyl |
| $(CH_2)_3$ | 4-pyridyl |
| $(CH_2)_3$ | 2-piperidyl |
| $(CH_2)_3$ | 4-piperidyl |
| $(CH_2)_4$ | 2-pyridyl |
| $(CH_2)_4$ | 4-pyridyl |
| $(CH_2)_4$ | 3-piperidyl |
| $(CH_2)_4$ | 4-piperidyl |
| $CH_2CH(CH_3)CH_2$ | 2-pyridyl |
| $CH_2CH(CH_3)CH_2$ | 4-piperidyl |
| $CH(CH_3)CH(CH_3)CH_2$ | 3-pyridyl |
| $CH(CH_3)CH(CH_3)CH_2$ | 4-pyridyl |
| $CH(CH_3)CH(CH_3)CH_2$ | 3-piperidyl |
| $CH(CH_3)(CH_2)_2$ | 2-pyridyl |
| $CH(CH_3)(CH_2)_2$ | 3-pyridyl |
| $CH(CH_3)(CH_2)_2$ | 4-piperidyl |
| $CH(CH_3)(CH_2)_3$ | 3-pyridyl |
| $CH(CH_3)(CH_2)_3$ | 4-piperidyl |
| $CH(CH_3)CH(C_2H_5)CH_2$ | 4-pyridyl |
| $CH(C_2H_5)(CH_2)_2$ | 4-pyridyl |
| $CH(C_2H_5)(CH_2)_2$ | 2-piperidyl |
| $CH(C_2H_5)(CH_2)_2$ | 4-piperidyl |
| $CH_2CH(C_2H_5)CH_2$ | 3-pyridyl |
| $CH(C_2H_5)(CH_2)_3$ | 3-pyridyl |
| $CH(C_2H_5)(CH_2)_3$ | 4-piperidyl |
| $CH(C_2H_5)CH(CH_3)CH_2$ | 2-pyridyl |
| $CH(C_2H_5)CH(C_2H_5)CH_2$ | 4-pyridyl |
| $CH(C_2H_5)CH(C_2H_5)CH_2$ | 2-piperidyl |
| $(CH_2)_3$ | $C_6H_{11}$ |
| $CH(CH_3)(CH_2)_3$ | $C_6H_{11}$ |
| $(CH_2)_4$ | $C_3H_5$ |
| $(CH_2)_2$ | $C_4H_7$ |
| $CH_2CH(CH_3)CH_2$ | $C_5H_9$ |
| $CH(CH_3)(CH_2)_2$ | $C_7H_{13}$ |
| $CH(CH_3)CH(CH_3)CH_2$ | $C_6H_{11}$ |
| $(CH_2)_6$ | $C_6H_5$ |
| $(CH_2)_7$ | $C_6H_5$ |
| $(CH_2)_8$ | $C_6H_5$ |
| $CH(CH_3(CH_2)_6$ | $C_6H_5$ |
| $CH(CH_3)(CH_2)_7$ | $C_6H_5$ |
| $CH(CH_3)(CH_2)_3$ | $4-FC_6H_4$ |
| $C(CH_3)_2(CH_2)_3$ | $C_6H_5$ |
| $CH(CH_3)(CH_2)_3$ | $4-ClC_6H_4$ |
| $CH(CH_3)(CH_2)_4$ | $4-ClC_6H_4$ |
| $CH(CH_3)(CH_2)$ | $4-ClC_6H_4$ |
| $CH(CH_3)(CH_2)$ | $4-FC_6H_4$ |
| $CH(CH_3)(CH_2)_2$ | $4-FC_6H_4$ |
| $CH(CH_3)(CH_2)_2$ | $4-ClC_6H_4$ |
| $(CH_2)_3CH(CH_3)$ | $C_6H_{11}$ |
| $CH(CH_3)(CH_2)_2CH(CH_3)$ | $C_6H_5$ |
| $CH(CH_3)(CH_2)_2CH(CH_3)$ | $C_6H_{11}$ |
| $CH(CH_3)(CH_2)_2CH(CH_3)$ | 4-piperidyl |
| $CH(CH_3)(CH_2)_3$ | $C_6H_{11}$ |
| $CH(CH_3)(CH_2CH(CH_3)$ | $C_6H_{11}$ |
| $(CH_2)_3$ | $C_6H_{11}$ |
| $(CH_2)_4$ | $C_6H_{11}$ |
| $(CH_2)_8$ | $C_6H_{11}$ |

PREPARATION N

3,5-Dimethoxy-α-methylstyrene Oxide

To a solution of dimethylsulfoxonium methylide (69.4 mM) in dimethyl sulfoxide (65 ml.) at room temperature is added solid 3,5-dimethoxyacetophenone (10 g., 55.5 mM). The reaction mixture is stirred for 1 hour at 25° C., for ½ hour at 50° C. and is then cooled. The mixture is diluted with water (50 ml.) and added to a mixture of ice water (200 ml.) — ether (250 ml.) — low boiling petroleum ether (25 ml.) The organic extract is washed twice with water (250 ml.), dried ($MgSO_4$) and evaporated to an oil. Fractional distillation of the oil yields 8.0 g. (75%) of 3,5-dimethoxy-α-methylstyrene oxide, b.p. 93°-97° C., 0.2 mm.

IR ($CCL_4$): 2780, 1595, 1196, 1151, 1058 $cm^{-1}$.

UV (95% ethanol): $\lambda_{max}$ = 279 nm ($\epsilon$= 2068)

MS (mol.ion): 194

PMR ($CDCl_3$) (60 MHz): δ (1.70 (S, $CH_3$—), 2.76 (d, J = 6 Hz,

H), 2.95 (d, J = 6 Hz,

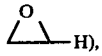

H), 3.81 (S, $CH_3O$—), 6.41 (t, J = 2 Hz, ArH) and 6.58 (d, J = 2 Hz, ArH).

Analysis: Calc'd for $C_{11}H_{14}O_3$: C, 68.02; H, 7.27%. Found: C, 67.96; H, 7.28%.

PREPARATION O

2-(3,5-Dimethoxyphenyl)-2-hydroxypropyl-2-phenylethyl Ether

A mixture of dry 2-phenylethanol (30 ml. 251 mM) and sodium metal (690 mg., 30 mM) is heated at 110° C. for 30 minutes. The resulting 1M solution of sodium 2-phenylethoxide is cooled to 60° C., 3,5-dimethoxy-α-methylstyrene oxide (2 g., 10.3 mM) added and the reaction heated 15 hours at 60° C. The reaction mixture is cooled and added to a mixture of ether and water. The ether extract is dried over magnesium sulfate and evaporated. Excess 2-phenylethanol is removed by vacuum distillation (b.p. ~65° C., 0.1 mm.) leaving a 3.5 g. residue. The residue is purified via column chromatography on Merck silica gel 60 (300 g.) and eluted in 15 ml. fractions with 60% ether-pentane. Fractions 52-88 yielded 2.9 g. (89%) of 2-(3,5-dimethoxyphenyl)-2-hydroxypropyl 2-phenylethyl ether.

IR ($CCl_4$): 3534, 1595, 1202, 1153 $cm^{-1}$.

UV (95% ethanol): $\lambda_{max}$ = 278 (ε = 1830), 273 (ε + 1860).

MS: (mol.ion) 316

PMR ($CDCl_3$, 60 MHz): δ 1.46 (S, $CH_3$—), 2.86 (S, OH), 2.86 (t, J = 7 Hz, —$CH_2$—Ph), 3.53 (S, —$CH_2O$), 3.71 (t, J = 7 Hz, —$CH_2O$), 3.80 (S, $OCH_3$), 6.38 (t, J = 2 Hz, Arh), 6.61 (d, J = 2 Hz, ArH) and 7.23 (S, PhH).

Analysis: Calc'd for $C_{19}H_{24}O_4$: C, 72.12; H, 7.65%. Found: C, 71.92; H, 7.63%.

PREPARATION P

2-(3,5-Dimethoxyphenyl)propyl 2-Phenylethyl Ether

To a 0° C. solution of 2-(3,5-dimethoxyphenyl)-2-hydroxypropyl 2-phenylethyl ether (550 mg., 1.74 mM) in pyridine (2 ml.) is added dropwise phosphorous oxychloride (4.77 ml., 5.22 mM). The reaction is allowed to warm to 20° C. over a 1.5 hour period. It is then stirred for 1.5 hours at 20° C. and then added to ether (150 ml.) and 15% sodium carbonate (100 ml.). The organic phase is separated and washed with 15% sodium carbonate (3 × 50 ml.), dried over magnesium sulfate and evaporated to an oil. The oil is dissolved in absolute ethanol (15 ml.), 10% palladium-on-carbon (100 mg.) added and the mixture stirred under one atmosphere of hydrogen gas. When hydrogen uptake ceases (26.5 ml., 20 min.), the reaction is filtered through diatomaceous earth and the filtrate evaporated to an oil. The oil is purified via preparative layer chromatography on silica gel plates, eluted twice with 6:1 pentane:ether to yield 211 mg. 840%) of 2-(3,5-dimethoxyphenyl)propyl 2-phenylethyl ether.

IR ($CCl_4$): 1600, 1205, 1155, 1109 $cm^{-1}$.

MS: (mol.ion) 300

PMR ($CDCl_3$, 60 MHz) δ 1.22 (d, J = 7 Hz, $CH_3$—), 2.82 (t, J = 7 Hz, $CH_2Ph$), ~2.8 (H—C—Me), ~3.6 (—$CH_2$—O—$CH_2$—), 3.75 (S, $OCH_3$), 6.35 (m, ArH) and 7.18 (S, PhH).

PREPARATION Q

2-(3,5-Dihydroxyphenyl)propyl 2-Phenylethyl Ether

A mixture of 2-(3,5-dimethoxyphenyl)propyl 2-phenylethyl ether (195 mg., 0.65 mM), pyridine (0.4 ml., 4.96 mM) and dry pyridine hydrochloride (4 g., 34.6 mM) is heated at 190° C. for 6 hours. The reaction mixture is cooled and added to a mixture of water (100 ml.) and ether (150 ml.). The ether extract is washed once with water (50 ml.) and, along with a second ether extract (50 ml.) of the aqueous phase, is dried over magnesium sulfate and evaporated to an oil. The oil is purified via preparative layer chromatography on silica gel plates, eluted six times with 30% ether-pentane to yield 65.8 mg. (37%) of 2-(3,5-dihydroxyphenyl)propyl 2-phenylethyl ether.

IR ($CHCl_3$): 3559, 3279, 1605, 1147, 1105 $cm^{-1}$.

MS: (mol.ion) 272

PMR ($CDCl_3$, 60 MHz) δ 1.18 (d, J = 7 Hz, $CH_3$—), 2.80 (t, J = 7 Hz, —$CH_2Ph$), 2.80 (H—C—Me), 3.4-3.8 (—$CH_2OCH_2$—), 6.08 (t, J = 2 Hz, ArH), 6.21 (d, J = 2 Hz, ArH) and 7.16 (S, PhH).

The following compounds are prepared from appropriate alkanols by the methods of Procedures O and P.

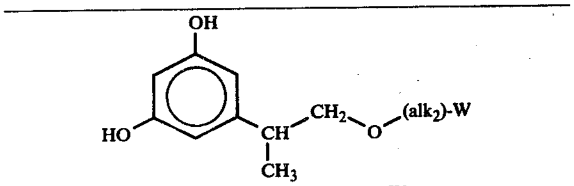

| ($alk_2$) | W |
|---|---|
| $-(CH_2)_6-$ | $CH_3$ |
| $-(CH_2)_6$ | $C_6H_5$ |
| $-(CH_2)_4$ | $CH_3$ |
| $-CH(CH_3)CH_2$ | $CH_3$ |
| $-CH(CH_3)(CH_2)_4$ | $CH_3$ |
| $-(CH_2)-$ | 4-$FC_6H_4$ |
| $-(CH_2)_2-$ | 4-pyridyl |
| $-(CH_2)_2-$ | 2-piperidyl |
| $-CH(CH_3)CH_2-$ | 4-piperidyl |
| $-(CH_2)_2CH(CH_3)(CH_2)_2-$ | $CH_3$ |
| $-CH(CH_3)-$ | $CH_3$ |
| $-C(CH_3)_2-$ | $CH_3$ |

PREPARATION R

4-(3,5-Dihydroxyphenyl)-1-phenoxypentane

Under a nitrogen atmosphere a mixture of 3,5-dibenzyloxyacetophenone (50.0 g., 0.15 M) in tetrahydrofuran (175 ml.) and 3-phenoxypropyltriphenylphosphonium bromide (7.18 g., 0.15 M) in dimethylsulfoxide (450 ml.) is added dropwise over 1.75 hours to a suspension of 50% sodium hydride (7.89 g., 0.165 M) (previously washed with pentane) in tetrahydrofuran (75 ml.) maintained at 0°-5° C. After stirring for 4 hours at 0°-5° C. the reaction is allowed to warm to room temperature and is then carefully stirred into ice water (2000 ml.), acidified with concentrated hydrochloric acid, and extracted with ethyl acetate (5 × 400 ml.). The combined organic phases are washed with saturated sodium chloride solution (3 × 300 ml.), dried over sodium sulfate -continued

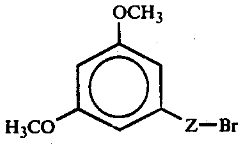

| Z |
| --- |
| $C(C_2H_5)CH_2$ |

PREPARATION M

4-(3,5-Dihydroxypenyl)-1-(4-pyridyl)pentane

A mixture of 3-(3,5-dimethoxyphenyl)butyl triphenylphosphonium bromide (19.0 g., 35.4 mmoles) in dimethylsulfoxide (50 ml.) is added to 4-pyridinecarboxaldehyde (3.79 g., 35.4 mmoles) in tetrahydrofuran (40 ml.). The resulting mixture is then added dropwise to a slurry of 50% sodium hydride (1.87 g., 39 mmoles) in tetrahydrofuran (20 ml.) under a nitrogen atmosphere at 0°-5° C. Following completion of addition, the mixture is stirred for one hour at 0°-5° and then concentrated under reduced pressure. The concentrate is diluted with water (200 ml.) and then acidified with 6N HCl. The aqueous acid solution is extracted with benzene (4 × 50 ml.). It is then made basic and extracted with ethyl acetate (3 × 50 ml.). Evaporation of the combined extracts after drying ($MgSO_4$) affords 4-(3,5-dimethoxyphenyl)-1-(4-pyridyl)-1-pentene (7.1 g., 70%) as an oil.

Catalytic hydrogenation of the thus-produced pentene derivative according to the procedure given in Preparation D gives 4-(3,5-dimethoxyphenyl)-1-(4-pyridyl)pentane in quantitative yield; m.p. 131°-133° C.

The pentane derivative thus obtained is demethylated by heating a mixture of the compound (7.15 g., 25 mmoles) and pyridine hydrochloride (35 g.) under a nitrogen atmosphere at 210° C. for 8 hours. The hot mixture is poured into water (40 ml.) and the resulting solution made basic with 6N sodium hydroxide. Water and pyridine are removed by distillation in vacuo. Ethanol (50 ml.) is added to the residue and the inorganic salts which precipitate are filtered off. The filtrate is concentrated in vacuo and the residue chromatographed on silica gel (150 g.) using as eluting agents 5% ethanol/benzene (4 liters), 10% ethanol/benzene (1 liter), 13% ethanol/benzene (1 liter) and 16% ethanol/benzene (5 liters). The product is isolated as a glassy solid by concentration of appropriate fractions of the eluate. Yield = 5.0 g. (78%).

The 3-(3,5-dimethoxyphenyl)butyltriphenylphosphonium bromide is prepared by refluxing a mixture of 1-bromo-3-(3,5-dimethoxyphenyl)butane (21.5 g., 78.5 mmoles) and triphenyl phosphine (20.5 g., 78.5 mmoles) in xylene (60 ml.) for 18 hours. The reaction mixture is then cooled to room temperature and filtered. The filter cake is washed with ether and dried in a vacuum desicator to give 36.4 g. (86%) yield of product; m.p. 190°-200° C.

Repetition of this procedure but using the appropriate bromo-(3,5-dimethoxyphenyl)alkane and the appropriate aldehyde or ketone affords the following compounds.

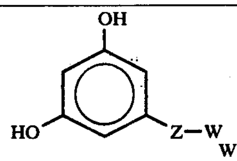

| Z | W |
| --- | --- |
| $(CH_2)_3$ | 2-pyridyl |
| $(CH_2)_3$ | 3-pyridyl |
| $(CH_2)_3$ | 4-pyridyl |
| $(CH_2)_3$ | 2-piperidyl |
| $(CH_2)_3$ | 4-piperidyl |
| $(CH_2)_4$ | 2-pyridyl |
| $(CH_2)_4$ | 4-pyridyl |
| $(CH_2)_4$ | 3-piperidyl |
| $(CH_2)_4$ | 4-piperidyl |
| $CH_2CH(CH_3)CH_2$ | 2-pyridyl |
| $CH_2CH(CH_3)CH_2$ | 4-piperidyl |
| $CH(CH_3)CH(CH_3)CH_2$ | 3-pyridyl |
| $CH(CH_3)CH(CH_3)CH_2$ | 4-pyridyl |
| $CH(CH_3)CH(CH_3)CH_2$ | 3-piperidyl |
| $CH(CH_3)(CH_2)_2$ | 2-pyridyl |
| $CH(CH_3)(CH_2)_2$ | 3-pyridyl |
| $CH(CH_3)(CH_2)_2$ | 4-piperidyl |
| $CH(CH_3)(CH_2)_3$ | 3-pyridyl |
| $CH(CH_3)(CH_2)_3$ | 4-piperidyl |
| $CH(CH_3)CH(C_2H_5)CH_2$ | 4-pyridyl |
| $CH(C_2H_5)(CH_2)_2$ | 4-pyridyl |
| $CH(C_2H_5)(CH_2)_2$ | 2-piperidyl |
| $CH(C_2H_5)(CH_2)_2$ | 4-piperidyl |
| $CH_2CH(C_2H_5)CH_2$ | 3-pyridyl |
| $CH(C_2H_5)(CH_2)_3$ | 3-pyridyl |
| $CH(C_2H_5)(CH_2)_3$ | 4-piperidyl |
| $CH(C_2H_5)CH(CH_3)CH_2$ | 2-pyridyl |
| $CH(C_2H_5)CH(C_2H_5)CH_2$ | 4-pyridyl |
| $CH(C_2H_5)CH(C_2H_5)CH_2$ | 2-piperidyl |
| $(CH_2)_3$ | $C_6H_{11}$ |
| $CH(CH_3)(CH_2)_3$ | $C_6H_{11}$ |
| $(CH_2)_4$ | $C_3H_5$ |
| $(CH_2)_2$ | $C_4H_7$ |
| $CH_2CH(CH_3)CH_2$ | $C_5H_9$ |
| $CH(CH_3)(CH_2)_2$ | $C_7H_{13}$ |
| $CH(CH_3)CH(CH_3)CH_2$ | $C_6H_{11}$ |
| $(CH_2)_6$ | $C_6H_5$ |
| $(CH_2)_7$ | $C_6H_5$ |
| $(CH_2)_8$ | $C_6H_5$ |
| $CH(CH_3(CH_2)_6$ | $C_6H_5$ |
| $CH(CH_3)(CH_2)_7$ | $C_6H_5$ |
| $CH(CH_3)(CH_2)_3$ | $4-FC_6H_4$ |
| $C(CH_3)_2(CH_2)_3$ | $C_6H_5$ |
| $CH(CH_3)(CH_2)_3$ | $4-ClC_6H_4$ |
| $CH(CH_3)(CH_2)_4$ | $4-ClC_6H_4$ |
| $CH(CH_3)(CH_2)$ | $4-ClC_6H_4$ |
| $CH(CH_3)(CH_2)$ | $4-FC_6H_4$ |
| $CH(CH_3)(CH_2)_2$ | $4-FC_6H_4$ |
| $CH(CH_3)(CH_2)_2$ | $4-ClC_6H_4$ |
| $(CH_2)_3CH(CH_3)$ | $C_6H_{11}$ |
| $CH(CH_3)(CH_2)_2CH(CH_3)$ | $C_6H_5$ |
| $CH(CH_3)(CH_2)_2CH(CH_3)$ | $C_6H_{11}$ |
| $CH(CH_3)(CH_2)_2CH(CH_3)$ | 4-piperidyl |
| $CH(CH_3)(CH_2)_3$ | $C_6H_{11}$ |
| $CH(CH_3)(CH_2CH(CH_3)$ | $C_6H_{11}$ |
| $(CH_2)_3$ | $C_6H_{11}$ |
| $(CH_2)_4$ | $C_6H_{11}$ |
| $(CH_2)_8$ | $C_6H_{11}$ |

PREPARATION N

3,5-Dimethoxy-α-methylstyrene Oxide

To a solution of dimethylsulfoxonium methylide (69.4 mM) in dimethyl sulfoxide (65 ml.) at room temperature is added solid 3,5-dimethoxyacetophenone (10 g., 55.5 mM). The reaction mixture is stirred for 1 hour at 25° C., for ½ hour at 50° C. and is then cooled. The mixture is diluted with water (50 ml.) and added to a mixture of ice water (200 ml.) — ether (250 ml.) — low boiling petroleum ether (25 ml.) The organic extract is washed twice with water (250 ml.), dried ($MgSO_4$) and evaporated to an oil. Fractional distillation of the oil yields 8.0 g. (75%) of 3,5-dimethoxy-α-methylstyrene oxide, b.p. 93°-97° C., 0.2 mm.

IR ($CCL_4$): 2780, 1595, 1196, 1151, 1058 $cm^{-1}$.

UV (95% ethanol): $\lambda_{max} = 279$ nm ($\epsilon = 2068$)

MS (mol.ion): 194

PMR ($CDCl_3$) (60 MHz): δ (1.70 (S, $CH_3$—), 2.76 (d, J = 6 Hz,

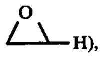

2.95 (d, J = 6 Hz,

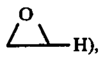

3.81 (S, $CH_3O$—), 6.41 (t, J = 2 Hz, ArH) and 6.58 (d, J = 2 Hz, ArH).

Analysis: Calc'd for $C_{11}H_{14}O_3$: C, 68.02; H, 7.27%. Found: C, 67.96; H, 7.28%.

PREPARATION O

2-(3,5-Dimethoxyphenyl)-2-hydroxypropyl-2-phenylethyl Ether

A mixture of dry 2-phenylethanol (30 ml. 251 mM) and sodium metal (690 mg., 30 mM) is heated at 110° C. for 30 minutes. The resulting 1M solution of sodium 2-phenylethoxide is cooled to 60° C., 3,5-dimethoxy-α-methylstyrene oxide (2 g., 10.3 mM) added and the reaction heated 15 hours at 60° C. The reaction mixture is cooled and added to a mixture of ether and water. The ether extract is dried over magnesium sulfate and evaporated. Excess 2-phenylethanol is removed by vacuum distillation (b.p. ~65° C., 0.1 mm.) leaving a 3.5 g. residue. The residue is purified via column chromatography on Merck silica gel 60 (300 g.) and eluted in 15 ml. fractions with 60% ether-pentane. Fractions 52–88 yielded 2.9 g. (89%) of 2-(3,5-dimethoxyphenyl)-2-hydroxypropyl 2-phenylethyl ether.

IR ($CCl_4$): 3534, 1595, 1202, 1153 $cm^{-1}$.

UV (95% ethanol): $\lambda_{max}$ = 278 (ε = 1830), 273 (ε + 1860).

MS: (mol.ion) 316

PMR ($CDCl_3$, 60 MHz): δ 1.46 (S, $CH_3$—), 2.86 (S, OH), 2.86 (t, J = 7 Hz, —$CH_2$—Ph), 3.53 (S, —$CH_2$O), 3.71 (t, J = 7 Hz, —$CH_2$O), 3.80 (S, $OCH_3$), 6.38 (t, J = 2 Hz, Arh), 6.61 (d, J = 2 Hz, ArH) and 7.23 (S, PhH).

Analysis: Calc'd for $C_{19}H_{24}O_4$: C, 72.12; H, 7.65%. Found: C, 71.92; H, 7.63%.

PREPARATION P

2-(3,5-Dimethoxyphenyl)propyl 2-Phenylethyl Ether

To a 0° C. solution of 2-(3,5-dimethoxyphenyl)-2-hydroxypropyl 2-phenylethyl ether (550 mg., 1.74 mM) in pyridine (2 ml.) is added dropwise phosphorous oxychloride (4.77 ml., 5.22 mM). The reaction is allowed to warm to 20° C. over a 1.5 hour period. It is then stirred for 1.5 hours at 20° C. and then added to ether (150 ml.) and 15% sodium carbonate (100 ml.). The organic phase is separated and washed with 15% sodium carbonate (3 × 50 ml.), dried over magnesium sulfate and evaporated to an oil. The oil is dissolved in absolute ethanol (15 ml.), 10% palladium-on-carbon (100 mg.) added and the mixture stirred under one atmosphere of hydrogen gas. When hydrogen uptake ceases (26.5 ml., 20 min.), the reaction is filtered through diatomaceous earth and the filtrate evaporated to an oil. The oil is purified via preparative layer chromatography on silica gel plates, eluted twice with 6:1 pentane:ether to yield 211 mg. 840%) of 2-(3,5-dimethoxyphenyl)propyl 2-phenylethyl ether.

IR ($CCl_4$): 1600, 1205, 1155, 1109 $cm^{-1}$.

MS: (mol.ion) 300

PMR ($CDCl_3$, 60 MHz) δ 1.22 (d, J = 7 Hz, $CH_3$—), 2.82 (t, J = 7 Hz, $CH_2$Ph), ~2.8 (H—C—Me), ~3.6 (—$CH_2$—O—$CH_2$—), 3.75 (S, $OCH_3$), 6.35 (m, ArH) and 7.18 (S, PhH).

PREPARATION Q

2-(3,5-Dihydroxyphenyl)propyl 2-Phenylethyl Ether

A mixture of 2-(3,5-dimethoxyphenyl)propyl 2-phenylethyl ether (195 mg., 0.65 mM), pyridine (0.4 ml., 4.96 mM) and dry pyridine hydrochloride (4 g., 34.6 mM) is heated at 190° C. for 6 hours. The reaction mixture is cooled and added to a mixture of water (100 ml.) and ether (150 ml.). The ether extract is washed once with water (50 ml.) and, along with a second ether extract (50 ml.) of the aqueous phase, is dried over magnesium sulfate and evaporated to an oil. The oil is purified via preparative layer chromatography on silica gel plates, eluted six times with 30% ether-pentane to yield 65.8 mg. (37%) of 2-(3,5-dihydroxyphenyl)propyl 2-phenylethyl ether.

IR ($CHCl_3$): 3559, 3279, 1605, 1147, 1105 $cm^{-1}$.

MS: (mol.ion) 272

PMR ($CDCl_3$, 60 MHz) δ 1.18 (d, J = 7 Hz, $CH_3$—), 2.80 (t, J = 7 Hz, —$CH_2$Ph), 2.80 (H—C—Me), 3.4–3.8 (—$CH_2OCH_2$—), 6.08 (t, J = 2 Hz, ArH), 6.21 (d, J = 2 Hz, ArH) and 7.16 (S, PhH).

The following compounds are prepared from appropriate alkanols by the methods of Procedures O and P.

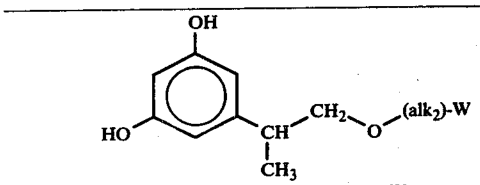

| ($alk_2$) | W |
|---|---|
| —$(CH_2)_6$— | $CH_3$ |
| —$(CH_2)_6$ | $C_6H_5$ |
| —$(CH_2)_4$ | $CH_3$ |
| —$CH(CH_3)CH_2$ | $CH_3$ |
| —$CH(CH_3)(CH_2)_4$ | $CH_3$ |
| —$(CH_2)$— | 4-$FC_6H_4$ |
| —$(CH_2)_2$— | 4-pyridyl |
| —$(CH_2)_2$— | 2-piperidyl |
| —$CH(CH_3)CH_2$— | 4-piperidyl |
| —$(CH_2)_2CH(CH_3)(CH_2)_2$— | $CH_3$ |
| —$CH(CH_3)$— | $CH_3$ |
| —$C(CH_3)_2$— | $CH_3$ |

PREPARATION R

4-(3,5-Dihydroxyphenyl)-1-phenoxypentane

Under a nitrogen atmosphere a mixture of 3,5-dibenzyloxyacetophenone (50.0 g., 0.15 M) in tetrahydrofuran (175 ml.) and 3-phenoxypropyltriphenylphosphonium bromide (7.18 g., 0.15 M) in dimethylsulfoxide (450 ml.) is added dropwise over 1.75 hours to a suspension of 50% sodium hydride (7.89 g., 0.165 M) (previously washed with pentane) in tetrahydrofuran (75 ml.) maintained at 0°-5° C. After stirring for 4 hours at 0°-5° C. the reaction is allowed to warm to room temperature and is then carefully stirred into ice water (2000 ml.), acidified with concentrated hydrochloric acid, and extracted with ethyl acetate (5 × 400 ml.). The combined organic phases are washed with saturated sodium chloride solution (3 × 300 ml.), dried over sodium sulfate and concentrated under vacuum to yield an oil which is triturated with ether to precipitate triphenylphosphine oxide. Filtration, followed by concentration of the filtrate, gives an oily residue which is chromatographed over silica gel (1300 g.) eluting with benzene-hexane consisting of 30% to 100% benzene. From the middle fractions 51 g. (75%) of 4-(3,5-dibenzyloxyphenyl)-1-phenoxypent-3-ene is isolated as an oil; $R_f = 0.8$ (silica gel, 2-benzene:1-hexane); MS (mol.ion): 450.

Analysis: Calc'd for $C_{31}H_{30}O_3$: C, 82.63; H, 6.71%. Found: C, 82.90; H, 6.69%.

A solution of 4-(3,5-dibenzyloxyphenyl)-1-phenoxypent-3-ene (51 g., 0.113 M) in a mixture of absolute ethanol (160 ml.), ethyl acetate (160 ml.) and concentrated hydrochloric acid (0.2 ml.) is hydrogenated for 12 hours under 55 lbs. hydrogen in the presence of 10% Pd/C. Removal of the catalyst by filtration and concentration of the filtrate under vacuum yields 30.8 g. (100%) of product as a viscous oil.

Analysis: Calc'd for $C_{17}H_{20}O_3$: C, 74.97; H, 7.40%. Found: C, 75.54; H, 7.45%.

PREPARATION S

3,5-Dimethoxy-β-methylstyrene oxide

To a −78° C. solution of diphenylsulfonium ethylide (1.0 mole) in tetrahydrofuran (one liter) is slowly added 3,5-dimethoxybenzaldehyde (1.0 mole). The reaction mixture is stirred at −78° C. for 3 hours and then allowed to warm to room temperature. It is then added to ether-water and the ether phase separated. The ether phase is washed with water, dried ($MgSO_4$) and evaporated. Fractional distillation of the residue gives the title product.

PREPARATION T

3-(3,5-Dihydroxyphenyl)-2-propylbutyl Ether

To a solution of sodium butoxide in butanol (0.5 liters of 1M) is added 3,5-dimethoxy-β-methylstyrene oxide (6.33 M). The mixture is heated for 18 hours at 70° C. and is then cooled and added to a mixture of ether-water. The ether solution is separated, dried ($MgSO_4$) and evaporated to give 3-(3,5-dimethoxyphenyl)-3-hydroxy-2-propylbutyl ether. It is purified by column chromatography on silica gel with ether-pentane elution.

By means of the procedure of Preparation P the title product is produced.

Similarly, the following are prepared from appropriate alcohols:

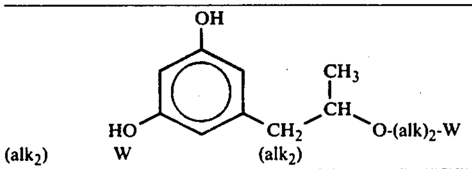

| $(alk_2)$ | W | $(alk_2)$ | W |
|---|---|---|---|
| $CH_2$ | $CH_3$ | $CH(CH_3)CH_2$ | $CH_3$ |
| $(CH_2)_6$ | $CH_3$ | $CH(C_2H_5)-(CH_2)_2$ | $CH_3$ |
| $(CH_2)_3$ | $C_6H_5$ | $CH(CH_3)CH_2$ | $C_6H_5$ |
| $(CH_2)_2$ | $4\text{-}FC_6H_4$ | | |
| $(CH_2)_2$ | 4-pyridyl | | |

PREPARATION U

2-$R_4R_5$-5,7-Dihydroxy-4-chromanones

The procedure of British Patent No. 1,077,066 is employed to produce the compounds tabulated below. It comprises reacting the appropriate $R_4R_5C{=}CH{-}COOH$ with an excess (50%) of 1,3,5-trihydroxybenzene and of polyphosphoric acid (10 to 20 grams per gram of trihydroxybenzene) on a steam bath for three hours. The mixture is then cooled and poured into water. The precipitate is extracted with ether, the ethereal extract washed with sodium hydroxide solution, dried and evaporated to afford the product. Purification is accomplished by distillation of the residue. The following are thus prepared:

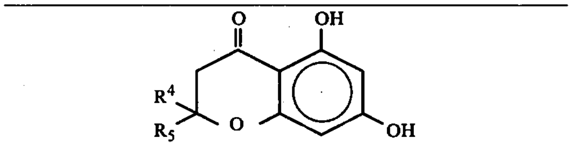

| $R_4$ | $R_5$ |
|---|---|
| $CH_3$ | H |
| H | H |
| $C_2H_5$ | $C_2H_5$ |
| $C_2H_5$ | H |
| $CH_3$ | $C_2H_5$ |

PREPARATION V

(4-Halophenyl)cyclohexanols

A. 3- and 4-(4-Fluorophenyl)cyclohexanols

A benzene solution containing equimolar amounts of 4-fluorostyrene and 2-methoxybutadiene and hydroquinone (1% by weight based on diene) is heated in a sealed tube at 150° C. for 10 hours. The reaction vessel is cooled, the contents removed and concentrated to give 1-methoxy-4(and 5)-4-(fluorophenyl)cycloheptene which are separated by distillation in vacuo. Hydrolysis of the ether with 3% hydrochloric acid affords 3- and 4-(4-fluorophenyl)cyclohexanones.

Sodium borohydride reduction of the ketones according to the procedure of Example 5 affords the keto compounds.

In like manner, the corresponding 3- and 4-(4-chlorophenyl)cyclohexanols are prepared from 4-chlorostyrene.

B. 2-(4-Fluorophenyl)cyclohexanol

This compound is prepared from cyclohexane oxide and p-fluorophenyl lithium according to the procedure of Huitric et al., *J. Org. Chem.*, 27, 715-9 (1962), for preparing 2-(4-chlorophenyl)cyclohexanol.

PREPARATION W

(2-Halophenyl)cycloalkanols

The procedure of Huitric et al., *J. Org. Chem.*, 27, 715-9 (1962) is employed but using the appropriate cycloalkylene oxide and p-halo (Cl or F) phenyl lithium reactants to produce the following compounds:

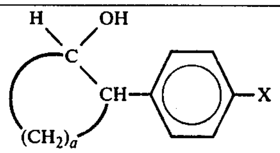

| a | X | a | X |
|---|---|---|---|
| 2 | Cl | 2 | F |
| 3 | Cl | 3 | F |
| 5 | Cl | 5 | F |

PREPARATION X

5-Hydroxy-7-mercapto-2,2-dimethyl-4-chromanone

A mixture of 3,5-dihydroxyphenyl methyl sulfide (5.85 g.) and 3-methylcrotonic acid (4.5 g.) is heated to 125° C. under nitrogen and boron trifluoride etherate (8.7 ml.) added. The mixture is refluxed for one hour and is then cooled. Water (10 ml.) is added, followed by 6N sodium hydroxide (40 ml.). The mixture is heated on a steam bath for 5 minutes, then cooled and acidified with 6N hydrochloric acid. It is extracted with ether (3 × 100 ml.) and the combined extracts washed with 10% sodium bicarbonate (1 × 25 ml.) and water (1 × 25 ml.) and then dried ($Na_2SO_4$). Concentration of the extract under vacuum affords dl-5-hydroxy-2,2-dimethyl-7-methylmercapto-4-chromanone. It is purified by silica gel chromatograhy.

The methyl mercapto compound thus produced is hydrolyzed by refluxing overnight with excess 48% hydrobromic acid. Concentration of the reaction mixture affords the title compound. It is purified by silica gel chromatography.

The following compounds are similarly prepared but replacing 3-methylcrotonic acid with the appropriate acid of the formula $R_4R_5C{=}CH{-}COOH$:

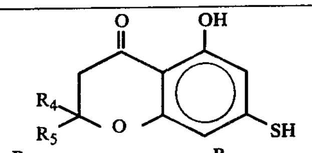

| $R_4$ | $R_5$ |
|---|---|
| H | $CH_3$ |
| H | H |
| $C_2H_5$ | $C_2H_5$ |
| H | $C_2H_5$ |
| $CH_3$ | $C_2H_5$ |

PREPARATION Y

Alkylation of 3,5-Dihydroxyphenylmercaptan

A solution of 3,5-dihydroxyphenylmercaptan (3.5 g., 0.01 mole) in absolute ethanol (50 ml.) is made just alkaline with sodium ethoxide. The appropriate bromide of formula $Br{-}(alk_2)_n{-}W$ (0.01 mole) is added and the mixture refluxed for 3 hours. It is then concentrated under reduced pressure and the residue extracted with ether. Evaporation of the ether affords the product.

The following compounds are thus prepared:

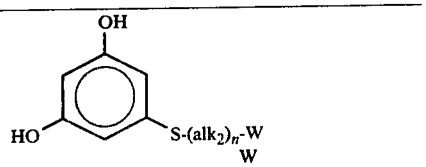

| n | $(alk_2)$ | W |
|---|---|---|
| 1 | $-CH(CH_3)(CH_2)_5-$ | $CH_3$ |
| 1 | $-CH(CH_3)CH(CH_3)(CH_2)_4-$ | $CH_3$ |
| 1 | $-C(CH_3)_2(CH_2)_5-$ | $CH_3$ |
| 1 | $-(CH_2)_8-$ | $CH_3$ |
| 1 | $-(CH_2)_4-$ | $CH_3$ |
| 1 | $-CH_2-$ | $C_6H_5$ |
| 1 | $-(CH_2)-$ | $C_6H_5$ |
| 1 | $-CH(CH_3)(CH_2)_3-$ | $C_6H_5$ |
| 1 | $-CH_2-$ | $C_3H_5$ |
| 1 | $-CH_2-$ | $C_5H_9$ |
| 1 | $-CH_2-$ | $C_6H_{11}$ |
| 1 | $-(CH_2)_2-$ | $C_5H_9$ |
| 1 | $-(CH_2)_3-$ | $C_5H_9$ |

-continued

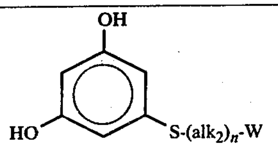

| n | $(alk_2)$ | W |
|---|---|---|
| 1 | $-(CH_2)_5-$ | $C_6H_{11}$ |
| 1 | $-(CH_2)_4-$ | $C_5H_9$ |
| 1 | $-(CH_2)_3CH(C_2H_5)-$ | $C_6H_{11}$ |
| 1 | $-(CH_2)_7-$ | $C_5H_9$ |
| 1 | $-(CH_2)_4-$ | $C_7H_{13}$ |
| 1 | $-(CH_2)_2-$ | $C_7H_{13}$ |
| 1 | $-(CH_2)_5-$ | $C_4H_7$ |
| 1 | $-(CH_2)_5-$ | $C_3H_5$ |
| 1 | $-(CH_2)-$ | 2-piperidyl |
| 1 | $-(CH_2)_3-$ | 4-piperidyl |
| 1 | $-(CH_2)-$ | 2-pyridyl |
| 1 | $-(CH_2)_3-$ | 3-pyridyl |
| 1 | $-(CH_2)_4-$ | 2-pyridyl |
| 1 | $-CH(CH_3)(CH_2)_2-$ | 2-pyridyl |
| 1 | $-CH(CH_3)(CH_2)_3-$ | 4-pyridyl |
| 1 | $-CH(C_2H_5)(CH_2)_2-$ | 4-piperidyl |
| 1 | $-(CH_2)_4-$ | $4\text{-}FC_6H_4$ |
| 1 | $-CH(CH_3)(CH_2)_2-$ | $4\text{-}ClC_6H_4$ |
| 1 | $-CH(CH_3)(CH_2)_3-$ | $4\text{-}FC_6H_4$ |
| 0 | — | $C_6H_5$ |
| 0 | — | $4\text{-}FC_6H_4$ |
| 0 | — | $4\text{-}ClC_6H_4$ |
| 0 | — | $C_3H_5$ |
| 0 | — | $C_5H_9$ |
| 0 | — | $C_6H_{11}$ |
| 0 | — | $C_7H_{13}$ |
| 0 | — | 4-pyridyl |
| 0 | — | 2-piperidyl |
| 0 | — | 2-pyridyl |
| 0 | — | $2\text{-}(C_6H_5)C_3H_4$ |
| 0 | — | $4\text{-}(C_6H_5)C_6H_{10}$ |
| 0 | — | $3\text{-}(C_6H_5)C_7H_{12}$ |
| 0 | — | $CH_3$ |

PREPARATION Z dl-2-(3,5-Dibenzyloxyphenyl)-2-hydroxy-1-(2-phenylethoxy)-propane

To a 20° C. a solution of dimethylsulfoxonium methylide (0.184 mole) in dimethylsulfoxide (185 ml.) is added 3,5-dibenzyloxyacetophenone (51.0 g., 0.153 mole). After stirring 1.5 hours at 20° C., the reaction is diluted with 200 ml. of ice water and added to 500 ml. ether and 200 ml. ice water. The organic phase is washed with cold water (2 × 200 ml.), dried over magnesium sulfate and evaporated to an oil. A solution of the thus produced crude 1-(3,5-dibenzyloxyphenyl)-1-methyloxirane (0.153 mole) in dimethylsulfoxide (100 ml.) is rapidly added to a 20° C. solution of sodium phenethoxide (0.306 mole) in dimethylsulfoxide (150 ml., made by the slow addition of 36.5 ml. [0.306 mole] of penethanol to a slurry of 7.34 g. [0.306 mole] sodium hydride in 150 ml. dimethylsulfoxide). The reaction is slowly heated over a ½-hour period to 70° C., stirred 30 minutes and cooled to 20° C. The reaction is diluted with 200 ml. ice water and added to ether (2 l.) and ice water (1 liter). The organic phase is washed with cold water (2 × 1 l.), dried over magnesium sulfate and evaporated to an oil. This crude oil is purified via column chromatography on 1.5 kg. of silica gel, and eluted with 60% ether-pentane to yield 30.0 g. (42%) of dl-2-(3,5-dibenzyloxyphenyl)-2-hydroxy-1-(2-phenylethoxy)propane, as an oil.

IR: ($CHCl_3$) OH 3534 $cm^{-1}$.

NMR: $\delta_{CDCl_3}^{TMS}$ 1.46 (s, methyl), 2.85 (t, J=7Hz, $-CH_2Ph$), 2.81 (s, hydroxyl), 3.55 (s, $-CH_2O-$), 3.68 (+, J=7Hz, $-OCH_2-$), 5.06 (s, $PhCH_2O-$), 6.56 (t, J=2Hz, C-4ArH), 6.76 (d, J=2Hz, C-2,6 ArH), 7.25 (s, ArH) and 7.43 (s,ArH).

MS:m/e 468 (M $\oplus$), 453, 377 and 335 (100%).

PREPARATION AA dl-2-(3,5-Dihydroxyphenyl)-1-(2-phenylethoxy)propane

To a 0° C. solution of dl-2-(3,5-dibenzyloxyphenyl)-2-hydroxy-1-(2-phenylethoxy)propane (29.0 g., 61.9 mmole) in pyridine (50 ml., 0.619 mole) is slowly added phosphorousoxy chloride (5.65 ml., 61.9 mmoles). The reaction is allowed to warm to 20° C. and is stirred at 20° C. for 20 hours. The reaction is added to a 0° C. solution of 3.3N NaOH (300 ml.) and the resultant mixture extracted with ether (3 × 500 ml.). Each extract is washed with saturated potassium carbonate (1 × 500 ml.) and water (3 × 500 ml.). The combined organic extract is dried over magnesium sulfate, silica gel and then decolorized (carbon) and evaporated to an oil. This oil is purified via column chromatography on silica gel (200 g.) eluted with 60% ether-pentane to yield 17 g. (61%) of an oil (mixture of olefins). To a solution of this mixture of olefins (3.62 g.) in ethanol (10 ml.) and ethyl acetate (10 ml.) is added solid sodium bicarbonate (300 mg.) and 10% Pd/C (1.2 g.) This mixture is stirred 6 hours under one atmosphere of hydrogen. The reaction is diluted with ethyl acetate and filtered through diatomaceous earth. The evaporated filtrate is purified via column chromatography on silica gel (200 g.) eluted with 80% ether-pentane to yield 2.0 g. (92%) of dl-2-(3,5-dihydroxyphenyl)-1-(2-phenylethoxy)propane as an oil.

IR: ($CHCl_3$) OH 3571, 3279 $cm^{-1}$.

NMR: $\delta_{CDCl_3}^{TMS}$ 1.10 (d, J=7Hz, methyl), 2.80 (t, J=7Hz, —$CH_2$Ph), 2.90 (M, methine), 3.5 (m, —$CH_2$O—$CH_2$—), 6.10 (t, J=2Hz, C-4 ArH), 6.20 (d, J=2Hz, C-2,6 ArH), 6.5 (broad m, hydroxyl) and 7.19 (s, ArH).

MS: m/e 272 (M$\oplus$), 181, 168, 151, 138, 137, 123, 105 (100%) and 91.

What is claimed is:

1. A compound having the formula

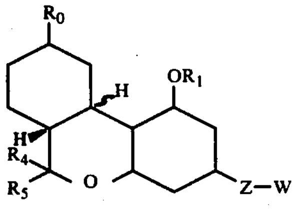

wherein $R_1$ is selected from the group consisting of hydrogen, alkanoyl having from one to five carbon atoms and —CO—$(CH_2)_p$—$NR_2R_3$ wherein p is 0 or an integer from 1 to 4; each of $R_2$ and $R_3$ when taken individually is selected from the group consisting of hydrogen and alkyl having from one to four carbon atoms; $R_2$ and $R_3$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

each of $R_4$ and $R_5$ is selected from the group consisting of hydrogen, methyl and ethyl;

$R_0$ is selected from the group consisting of oxo and alkylenedioxy having from two to four carbon atoms;

Z is —$(alk_1)_m$—X—$(alk_2)_n$— wherein each of ($alk_1$) and ($alk_2$) has from 1 to 9 carbon atoms, with the proviso that the summation of carbon atoms in ($alk_1$) plus ($alk_2$) is not greater than 9;

each of m and n is 0 or 1;

X is selected from the group consisting of O, S, SO and $SO_2$; and

W is selected from the group consisting of methyl, pyridyl, piperidyl,

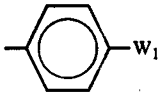

wherein $W_1$ is selected from the group consisting of hydrogen, fluoro and chloro; and

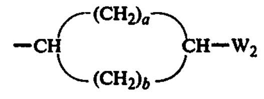

wherein W is selected from the grup consisting of hydrogen and

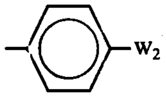

and a is an integer from 1 to 5 and b is 0 or an integer from 1 to 5; with the proviso that the sum of a and b is not greater than 5.

2. A compound according to claim 1 wherein $R_0$ is oxo.

3. A compound according to claim 2 wherein each of $R_4$ and $R_5$ is methyl and W is

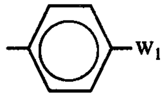

wherein $W_1$ is hydrogen.

4. A compound according to claim 3 wherein Z is —$(alk_1)_m$—O—$(alk_2)_n$—.

5. A compound according to claim 4 wherein m is 0 and n is 1.

6. A compound according to claim 4 wherein m is 1 and n is 0.

7. The compound according to claim 4 wherein each of m and n is 0.

8. The compound according to claim 5 wherein —($alk_2$)— is —$CH(CH_3)$—$(CH_2)_3$—.

9. The compound according to claim 5 wherein —($alk_2$)— is —$CH(CH_3)$—$(CH_2)_2$—.

10. The compound according to claim 6 wherein —($alk_1$)— is —$CH(CH_3)$—$(CH_2)_3$—.

11. The compound according to claim 6 wherein —($alk_1$)— is —$CH(CH_3)$—$(CH_2)_2$—.

12. A compound according to claim 2 wherein each of $R_4$ and $R_5$ is methyl and W is methyl.

13. A compound according to claim 12 wherein Z is —$(alk_1)_m$—O—$(alk_2)_n$—.

14. A compound according to claim 13 wherein m is 0 and n is 1.

15. The compound according to claim 14 wherein ($alk_2$) is $—CH(CH_3)—(CH_2)_4—$.

16. A process for producing an anti-hypertensive effectn in a mammal which comprises administering to the mammal an antihypertensive producing quantity of a compound of claim 1.

17. The process of claim 16 wherein $R_0$ is oxo.

18. The process of claim 17 wherein each of $R_4$ and $R_5$ is methyl and W is

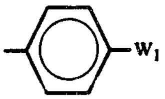

wherein $W_1$ is hydrogen.

19. The process of claim 18 wherein Z is $—(alk_1)_m—O—(alk_2)_n—$.

20. The process of claim 19 wherein m is 0 and n is 1.

21. The process of claim 20 wherein $—(alk_2)—$ is $—CH(CH_3)—(CH_2)_3—$.

* * * * *

UNITED STATES PATENT AND TRADEMARK OFFICE

CERTIFICATE OF CORRECTION

PATENT NO. : 4,143,139
DATED : March 6, 1979
INVENTOR(S) : Jasjit S. Bindra

It is certified that error appears in the above-identified patent and that said Letters Patent are hereby corrected as shown below:

Claim 1, line 2, that portion of the formula reading

" 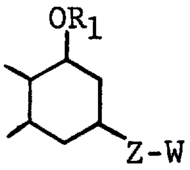 " should read -- 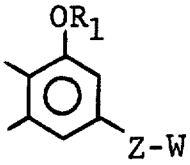 --.

Signed and Sealed this

*Twenty-sixth* Day of *June 1979*

[SEAL]

*Attest:*

RUTH C. MASON
*Attesting Officer*

DONALD W. BANNER
*Commissioner of Patents and Trademarks*